(12) United States Patent
Yonehara

(10) Patent No.: US 8,093,409 B2
(45) Date of Patent: Jan. 10, 2012

(54) METHOD FOR PRODUCING CYCLIC UNSATURATED COMPOUND

(75) Inventor: Koji Yonehara, Nagaokakyo (JP)

(73) Assignee: Nippon Shokubai Co., Ltd., Osaka-Shi, Osaka (JP)

( * ) Notice: Subject to any disclaimer, the term of this patent is extended or adjusted under 35 U.S.C. 154(b) by 0 days.

(21) Appl. No.: 12/438,183

(22) PCT Filed: Aug. 22, 2007

(86) PCT No.: PCT/JP2007/066695
§ 371 (c)(1),
(2), (4) Date: Mar. 13, 2009

(87) PCT Pub. No.: WO2008/023823
PCT Pub. Date: Feb. 28, 2008

(65) Prior Publication Data
US 2009/0299009 A1 Dec. 3, 2009

(30) Foreign Application Priority Data

Aug. 22, 2006 (JP) ................................ 2006-225756
Apr. 6, 2007 (JP) ................................ 2007-100962

(51) Int. Cl.
*C07D 307/00* (2006.01)
*C07D 309/38* (2006.01)
(52) U.S. Cl. ........................................ 549/326; 549/294
(58) Field of Classification Search ................. 549/326, 549/294
See application file for complete search history.

(56) References Cited

U.S. PATENT DOCUMENTS

| | | | |
|---|---|---|---|
| 3,755,423 A | 8/1973 | Onoda et al. | |
| 5,576,460 A * | 11/1996 | Buchwald et al. | 564/386 |
| 6,232,474 B1 | 5/2001 | Brandenburg et al. | |
| 6,479,693 B2 * | 11/2002 | Seayad et al. | 560/100 |
| 6,531,607 B2 * | 3/2003 | Goossen et al. | 548/103 |

FOREIGN PATENT DOCUMENTS

| | | |
|---|---|---|
| EP | 0551019 | 7/1993 |
| JP | 51-63119 | 6/1976 |
| JP | 52-12171 | 4/1977 |
| JP | 52-12685 | 4/1977 |
| JP | 52-29726 | 8/1977 |
| JP | 52-29727 | 8/1977 |
| JP | 5-186455 | 7/1993 |
| JP | 10-120672 | 5/1998 |
| JP | 2005-013800 | 1/2005 |
| JP | 2005-034720 | 2/2005 |
| JP | 2005-105336 | 4/2005 |

OTHER PUBLICATIONS

Ferret, N. et al, Acryloxy and methacryloxy palladation of alkenes, Journal of the Chemical Society, Chemical Communications, 1994, No. 22, p. 2589-2590.*

Tsuji et al. Organic Syntheses, Coll. vol. 7, p. 137 (1990); vol. 62, p. 9 (1984).*
Ferret, et al., "Acryloxy and Methacryloxy Palladation of Alkenes", Journal of the Chemical Society, Chemical Communications, 1994, No. 22, pp. 2589-2590.
Gagnier et al., "Palladium-Catalyzed Heteroannulation of 1,3-Dienes to form α-alkylidene-γ-butyrolactones", Journal of Organic Chemistry, vol. 65, No. 5, 2000, pp. 1525-1529.
Iyer et al., "The Pd Catalyzed Reactions of α-Bromo Acrylic acids with 1,3-Dienes to form γ-Lactones", Tetrahedron Letters, vol. 40, No. 25, 1999, pp. 4719-4720.
Rossi et al., "Studies on the Transition Metal-Catalyzed Synthesis of Variously Substituted (E)-3-[1-(aryl)methylidene]- and (E)-3-(1-alkylidene)-3H-furan-2-ones", Tetrahedron, vol. 54, No. 1/2, 1998, pp. 135-156.
Heumann et al., "Palladium Complex Catalyzed Oxidation Reactions", Progress in Inorganic Chemistry, 42, 1994, pp. 483.
Hoffmann et al., "Synthesis and Biological Activity of α-Methylene-γ-butyrolactones", Angew. Chem. Int. Ed. Engl. vol. 24, No. 2, 1985, pp. 94-110.
Murray et al., "Palladium-Catalyzed Cyclocarbonylation of Acetylenic Alcohols to Methylene Lactones. Scope and Synthesis of Appropriate Substrates", Journal of the American Chemical Society, vol. 103, 1981, pp. 7520-7528.
Semmelhack et al., "Nickel-Promoted Cyclization/Carbonylation in the Preparation of α-Methylene γ-Lactones: Stereospecific Synthesis of (±) Frullanolide", Journal of the American Chemical Soceity, vol. 103, 1981, pp. 3945-3947.
Jabre-Truffert et al., "Intramolecular Acryloxypalladation, Stereospecific Synthesis of Ring Fused Unsaturated α-Methylene-γ-Butyrolactones", Tetrahedron Letters, vol. 38, 1997, pp. 835-836.
Takehira et al., "Liquid Phase Diacetoxylation of 1,3-Butadiene with Pd-Te-C Catalyst", Journal of Catalysis, Journal of Catalysis, vol. 58, 1979, pp. 155-169.
Fujita et al., "Reaction of 3,4-unsaturated carboxylic acids with epoxides", Chemical and Industry, 1983, pp. 897.
Bando et al., "Efficient Synthesis of 2-Vinyl-γ-butyrolactones and 2-Vinyl-γ-butyrolactams by Palladium-Catalyzed Decarboxylative Carbonylation", The Chemical Society of Japan, vol. 65, 1992, pp. 97-110.
Tezuka et al., "Cationic palladium complex-catalyzed cyclocarbonylation of 3-butyn-1-ols", Journal of Molecular Catalysis A: Chemical (1989), 129(2-3), 199-206.
Extended European Search Report, European May 13, 2009.
Larock, et al., "Synthesis of Unsaturated Lactones via Palladium-Catalyzed Cyclization of Alkenoic Acids", Journal of Organic Chemistry, 1993, vol. 58(20), pp. 5298-5300.

* cited by examiner

*Primary Examiner* — Nizal Chandrakumar
(74) *Attorney, Agent, or Firm* — Connolly Bove Lodge & Hutz LLP

(57) ABSTRACT

The present invention provides a method for producing a cyclic unsaturated compound, which sufficiently suppresses generation of acyclic unsaturated compounds and permits excellent yield and reaction rate. Such a method for producing a cyclic unsaturated compound is a method for producing a cyclic unsaturated compound by reacting an α,β-unsaturated carboxylic acid with an unsaturated organic compound, wherein the method comprises a step of reacting the α,β-unsaturated carboxylic acid with the unsaturated organic compound in the presence of a catalyst.

20 Claims, 2 Drawing Sheets

Reaction active species

METHOD FOR PRODUCING CYCLIC UNSATURATED COMPOUND

CROSS REFERENCE TO RELATED APPLICATIONS

This application is a National Stage of PCT/JP2007/066695 filed Aug. 22, 2007 which in turn claims priority from Japanese Application 2006-225756 filed Aug. 22, 2006 and Japanese Application 2007-100962 filed Apr. 6, 2007, the entire contents of which are incorporated herein by reference.

TECHNICAL FIELD

The present invention relates to a method for producing cyclic unsaturated compounds. More specifically, the present invention relates to a method for producing a cyclic unsaturated compound from an α,β-unsaturated carboxylic acid and an unsaturated organic compound.

BACKGROUND ART

Cyclic unsaturated compounds have been known as a skeleton which shows physiological activity, and have been expected to be used as a monomer for producing polymers having characteristics such as heat resistance, optical property, UV curability, and adherence, as well as an intermediate for pharmaceuticals and agrichemicals such as an antitumor agent and an antivirotic. Polymers obtained from such monomers can be used as raw materials for various chemical products such as an electronic and informational material, an optical material, a photosensitive material, a coating material, an adhesive, a detergent builder, or raw materials for pharmaceuticals and agrichemicals. Thus, the cyclic unsaturated compounds are useful in chemical, pharmaceutical, and agrichemical fields.

As a conventional production method of such a cyclic unsaturated compound, a method for producing α-methylene-γ(gamma)-butyrolactones using cyclic reaction of 4-hydroxy-2-methylenebutanoic acid and cyclic reaction of 2-methylene-4-pentanoic acid was disclosed (for example, refer to Hoffmann, H. M. R.), and 1 other, "Angewandte Chemie International Edition in English", (Germany), VCH, 1985, vol. 24, No. 2, p. 94 to 110). Further, a method for producing α-methylene-γ-butyrolactone from γ-butyrolactone and formaldehyde using a basic compound was disclosed (for example, refer to U.S. Pat. No. 6,232,474 and Japanese Kokai Publication No. Hei-10-120672). However, these methods have room for improvement in order to be applied to industrial production because expensive organic reagents are used; reactions are performed in multiple stages; reaction conditions such as temperature are severe in the reaction steps; deterioration of the catalyst is easily caused; and such methods are inferior in terms of cost.

A method for producing α-methylene-γ-butyrolactones from a triple bond-containing alcohol and carbon monoxide using palladium as a catalyst was disclosed (for example, refer to Murray, T. F., and three others "Journal of the American Chemical Society" (U.S.) American Chemical Society, 1981, vol. 103, p. 7520 to 7528). However, such a method has room for improvement in order to be applied to industrial production because expensive raw materials and carbon monoxide with high toxicity are used and therefore such a method is inferior in terms of cost and safety.

Further, a method for producing α-methylene-γ-butyrolactones from an unsaturated alcohol in which halogen is bonded to a double bond and carbon monoxide using nickel was disclosed (for example, refer to Semmelhack, M. F., and one other, "Journal of the American Chemical Society", (U.S.) American Chemical Society, 1981, vol. 103, p. 3945 to 3947). However, such a method has room for improvement in order to be applied to industrial production because expensive raw materials and carbon monoxide with high toxicity are used and therefore such a method is inferior in cost and safety.

With respect to reactions utilizing acryloxy palladation or methacryloxy palladation of alkene, methods for producing unsaturated chain esters typified by acrylic esters and methacrylic esters or unsaturated cyclic esters typified by α-methylene-γ-butyrolactones using palladium acetate/benzoquinone/manganese dioxide catalytic system were disclosed (for example, refer to Ferret, N., and three others, "Journal of Chemical Society Chemical Communication", (Britain), Royal Society of Chemistry, 1994, No. 22, p. 2589 to 2590). Table 1 in the document of Ferret et al. discloses a reaction utilizing typical acryloxy palladation of alkene by acrylic acid or methacrylic acid using this catalytic system. For example, Example 7 shows a reaction using acrylic acid and norbornene. However, the reaction rate is insufficient and therefore the productivity is low. Further, it is found that if a reaction is performed by this known art using acrylic acid and ethylene as starting materials, vinyl acrylate is overwhelmingly generated more than α-methylene-γ-butyrolactone and therefore the selectivity of the desired α-methylene-γ-butyrolactone is extremely low. Therefore, such a reaction has room for improvement in order to be a method for producing cyclic unsaturated compounds, which has high versatility not depending on the kind of substrates and high productivity.

With respect to reactions using intramolecular acryloxy palladation of alkene, a method for producing unsaturated cyclic esters typified by α-methylene-γ-butyrolactones using palladium acetate/benzoquinone/manganese dioxide catalytic system or palladium acetate/sodium acetate/oxygen catalytic system was disclosed (for example, refer to Jabre-Truffert, S., and one other, "Tetrahedron Letters", (Britain), Elsevier Science, 1997, vol. 38, p. 835 to 836). However, it is found that if a reaction is performed under conditions of this known art using acrylic acid and ethylene as starting materials, vinyl acrylate is overwhelmingly generated more than α-methylene-γ-butyrolactone and the reaction hardly proceeds. In addition, there was not disclosure about the intermolecular reaction and starting materials produced through multiple steps must be used for the intramolecular cyclic reaction and therefore such a method is inferior in cost. Therefore, such a method has room for improvement in order to be applied to industrial production.

Further, a solid catalyst containing palladium and tellurium, its production method, and a method for producing an oxidation reaction product by performing diacetoxylation of butadiene using the catalyst was disclosed (for example, refer to Japanese Kokoku Publication No. Sho-52-29726, Japanese Kokoku Publication No. Sho-52-29727, Japanese Kokoku Publication No. Sho-52-12685, Japanese Kokoku Publication No. Sho-52-12171, Japanese Kokai Publication No. Sho-51-63119, Japanese Kokai Publication No. 2005-34720, Japanese Kokai Publication No. 2005-13800, Japanese Kokai Publication No. 2005-105336, Takehira, K., and two others, "Journal of Catalysis" (U.S.), Elsevier Science, 1979, vol. 58, p. 155 to 169). For example, butadiene is coordinated to palladium, and one acetic acid (acetate) attacks an end of a double bond and is bonded thereto, followed by formation of a π(pi)-allyl palladium species, and successively, another acetic acid (acetate) attacks an end of the π-allyl site, thereby generating 1,4-diacetoxy-2-butene. However, such methods are not preferably applied to methods for producing cyclic unsaturated compounds because of the reaction mechanisms and the like. Therefore, methods for producing cyclic unsaturated compounds, which permit excellent yield and reaction rate have been desired.

Further, a method for producing lactone compounds containing a vinyl group at the α position from a β,γ-unsaturated carboxylic acid and an epoxy compound was disclosed (for example, refer to Fujita, T., and four others, Chemistry & Industry, (Britain), 1983, p. 897). Further, a method for producing lactone compounds containing a vinyl group at the α position from 4-vinyl-1,3-dioxane-2-one using palladium as a catalyst was disclosed (for example, refer to Bando, T., and four others, "Bulletin of the Chemical Society of Japan", (Japan), the Chemical Society of Japan, 1992, vol. 65, p. 97 to 110). However, these methods have room for improvement in order to be applied to industrial production because expensive organic reagents such as lithium naphthalenide are needed and expensive starting material substrates and carbon monoxide with high toxicity must be used and therefore such methods are inferior in cost and safety.

DISCLOSURE OF THE INVENTION

Problem to be Solved by the Invention

The present invention has been made in view of the above-mentioned state of the art. The present invention has an object to provide a simple and efficient method for producing a cyclic unsaturated compound, which sufficiently suppresses generation of acyclic unsaturated compounds and permits excellent yield and reaction rate.

Means for Solving the Problem

The present inventors made various investigations on efficient production methods of a cyclic unsaturated compounds, and noted a method for producing a cyclic unsaturated compound by reacting an α,β-unsaturated carboxylic acid with an unsaturated organic compound. The inventors found that if the production method includes a step of reacting the α,β-unsaturated carboxylic acid with the unsaturated organic compound in the presence of a catalyst, a reaction rate, and a yield or a selectivity of the cyclic unsaturated compound can be sufficiently excellent and generation of byproducts can be sufficiently suppressed. In addition, the inventors found that if the above-mentioned catalyst essentially includes a compound including at least one element selected from the group consisting of elements of the Groups 8 to 12, the reaction rate and the yield or the selectivity of the cyclic unsaturated compound can be more sufficiently excellent and generation of byproducts can be sufficiently suppressed. Further, the inventors found that if the above-mentioned production method includes a method of reoxidizing the catalyst using a reoxidant agent, generation of acyclic unsaturated compounds can be sufficiently suppressed and the yield or the selectivity of the cyclic unsaturated compound can be sufficiently improved, and also found that if molecular oxygen is used as one reoxidant agent in the above-mentioned step of reoxidizing the catalyst, the reaction can more efficiently proceed.

The present inventors also found that if the production method of the present invention includes a step of reacting the α,β-unsaturated carboxylic acid with the unsaturated organic compound in the presence of a promoter(cocatalyst), the step of reoxidizing the catalyst can be smoothly performed and therefore the production method of the cyclic unsaturated compound of the present invention can be more efficient. Further, the present inventors found that if the production method of the present invention includes a step of reacting the α,β-unsaturated carboxylic acid with the unsaturated organic compound in the presence of a nitrile solvent, the cyclic unsaturated compound can be efficiently produced at a smaller amount of the catalyst without using an organic reoxidant agent and the like, and such a method has advantages in terms of reduction in costs, and environment. Further, the inventors found that if the production method of the present invention includes a step of reacting the α,β-unsaturated carboxylic acid with the unsaturated organic compound in the presence of a hydrocarbon solvent coordinated weakly to a catalyst, the cyclic unsaturated compound can be efficiently produced at a smaller amount of the catalyst without using the above-mentioned organic reoxidant agent. The inventors also found that if the above-mentioned production method of the present invention includes a step of inserting an unsaturated bond of the α,β-unsaturated carboxylic acid into a metal-carbon bond, the yield or the selectivity of the cyclic unsaturated compound can be more sufficiently improved. Further, the inventors found that according to the above-mentioned production method of the present invention, if in the above-mentioned α,β-unsaturated carboxylic acid, at least one hydrogen atom is bonded to carbon at the γ position, preferable effects of the present invention, in which the reaction rate and the yield or the selectivity of the cyclic unsaturated compound can be improved, are exhibited.

Further, the inventors found that if the above-mentioned unsaturated organic compound is a double bond-containing compound having 2 to 20 carbon atoms in the above-mentioned production method of the present invention, preferable effects of the present invention, in which generation of acyclic unsaturated compounds can be sufficiently suppressed and the reaction rate, and the yield or the selectivity of the cyclic unsaturated compound can be improved, are exhibited. The inventors also found that if the above-mentioned cyclic unsaturated compound is a compound containing a double bond, and the double bond exists at the exo position and/or the endo position, the reaction rate, and the yield or the selectivity of the cyclic unsaturated compound can be sufficiently excellent. Further, the inventors found that if the above-mentioned cyclic unsaturated compound is a compound containing a double bond and the double bond exists in the side chain of the ring structure, the reaction rate, and the yield or the selectivity of the cyclic unsaturated compound can be sufficiently excellent. Further, the inventors found that if the above-mentioned double bond is a double bond of a vinyl group, the reaction rate, and the yield or the selectivity of the cyclic unsaturated compound can be sufficiently excellent. The inventors also found that generation of acyclic unsaturated compounds can be sufficiently suppressed and the yield or the selectivity of the cyclic unsaturated compound can be sufficiently improved by a catalyst for producing a cyclic unsaturated compound by reacting an α,β-unsaturated carboxylic acid with an unsaturated organic compound, wherein the catalyst is supported on a carrier and includes a compound including at least one element selected from the group consisting of elements of the Groups 8 to 12 and an element other than the elements of the Groups 8 to 12. Further, the inventors found that an α-methylene-γ-butyrolactone composition including a cyclic unsaturated compound containing a double bond at the endo position is a characteristic product of the production method of the present invention, and that an α-methylene-γ-butyrolactone composition including a six-membered unsaturated compound is also a characteristic product of the production method of the present invention. As a result, the above-mentioned problems had been admirably solved, leading to completion of the present invention.

With respect to oxidation catalysts used for such reactions as in the present invention, if a catalyst reduced in a reaction system is reoxidized to efficiently progress the reaction, a method in which a substrate is used as a solvent and an organic reoxidant agent or a halogen compound is coexistent in the system is generally used. However, a new method for reoxidizing the catalyst, which is different from the above-mentioned method, was found. That is, with respect to methods for reoxidizing a reduced catalyst by selecting the solvent, (1) a method for reoxidizing a catalyst in the presence of a nitrile solvent and (2) a method for reoxidizing a catalyst in the presence of a hydrocarbon solvent coordinated weakly to the catalyst were newly found. (1) If the reoxidation is performed in the presence of a nitrile solvent, a nitrile site of the solvent is coordinated to the catalyst and thereby aggregation of the catalysts is suppressed. As a result, the step of reoxidizing the catalyst smoothly proceeds. Therefore, the reoxidation can proceed efficiently. In addition, an oxidation-reduction potential of the catalyst is influenced, and thereby the reoxidation of the catalyst may efficiently proceed even in the absence of organic reoxidant agents or halogen compounds. (2) If the reoxidation is performed in the presence of a hydrocarbon solvent coordinated weakly to the catalyst, solvent molecules are hardly coordinated to the catalyst, and therefore a function in which a reoxidant agent or a promoter component oxidizes the catalyst is improved without being disturbed by the solvent molecules and thereby the reoxidation easily proceeds and the catalyst forms a multi-nuclear complex, for example. As a result, the active catalyst maintains the high oxidation state (the catalyst does not undergo a reduction state during the reaction). By the above-mentioned (1) or (2) reoxidation method, the reduced catalyst can be sufficiently suppressed from aggregating and being deactivated. The above-mentioned hydrocarbon solvent means at least one compound selected from the group consisting of hydrocarbon compounds and aromatic hydrocarbon compounds in the present description. In reaction systems using such methods, advantageous effects in which the use amount of the catalyst can be reduced in the presence of molecular oxygen and the catalyst can be efficiently reoxidized substantially without using organic reoxidant agents are exhibited.

The present invention is mentioned below in more detail.

The present invention is a method for producing a cyclic unsaturated compound by reacting an $\alpha,\beta$-unsaturated carboxylic acid with an unsaturated organic compound, wherein the method comprises a step of reacting the $\alpha,\beta$-unsaturated carboxylic acid with the unsaturated organic compound in the presence of a catalyst.

The present invention is also a catalyst for producing a cyclic unsaturated compound by reacting an $\alpha,\beta$-unsaturated carboxylic acid with an unsaturated organic compound, wherein the catalyst is supported on a carrier and comprises a compound including at least one element selected from the group consisting of elements of the Groups 8 to 12 and an element other than the elements of the Groups 8 to 12.

The present invention is also an $\alpha$-methylene-$\gamma$-butyrolactone composition including a cyclic unsaturated compound containing a double bond at an endo position.

Further, the present invention is also an $\alpha$-methylene-$\gamma$-butyrolactone composition including a six-membered unsaturated compound.

The production method of the present invention may include other steps as long as it is a method for producing a cyclic unsaturated compound by reacting an $\alpha,\beta$-unsaturated carboxylic acid with an unsaturated organic compound, wherein the method includes a step of reacting the $\alpha,\beta$-unsaturated carboxylic acid with the unsaturated organic compound in the presence of a catalyst. One or two or more species may be used as the $\alpha,\beta$-unsaturated carboxylic acid, the unsaturated organic compound, and the catalyst, respectively.

The presence of the above-mentioned catalyst improves reactivity of the $\alpha,\beta$-unsaturated carboxylic acid with the unsaturated organic compound, and thereby the reaction rate of the production method of the present invention and the yield of the cyclic unsaturated compound can be improved and a catalytic active species effective for this reaction can be formed.

The catalyst used in the production method of the present invention is not especially limited and catalysts commonly used for production of the cyclic unsaturated compound from the $\alpha,\beta$-unsaturated carboxylic acid and the unsaturated organic compound may be used.

The above-mentioned catalyst is a substance which has a function of lowering activation energy in a reaction and permits a new reaction pathway by forming a short-lived intermediate with a substrate, thereby increasing a reaction rate. It is preferable that a relatively smaller amount of the catalyst is used in comparison to an amount of the substrate. However, the term catalyst as used herein includes a promoter and a catalyst which is recovered after a reaction using a substrate and a catalyst at an amount equivalent to or more than an amount of the substrate and which can be used also for reactions after the first reaction. In this case, a treatment for reactivating the catalyst may or may not be performed after completion of the first reaction. The catalyst may contain a promoter component which assists catalytic functions at a reactive site.

It is preferable in the production method of the present invention that the catalyst comprises a compound including at least one element selected from the group consisting of elements of the Groups 8 to 12. One or two or more different elements among the above-mentioned elements may be used.

If such a catalyst is used as the above-mentioned catalyst, the reaction rate of the production method of the present invention and the yield of the cyclic unsaturated compound can be more improved, and generation of byproducts can be suppressed.

It is more preferable that the above-mentioned catalyst essentially includes a compound including at least one element selected from the group consisting of elements of the Group 10.

The above-mentioned compound including at least one element selected from the group consisting of elements of the Group 10 is not especially limited, and nickel-containing compounds, palladium-containing compounds, and platinum-containing compounds may be mentioned, for example. Among them, the palladium-containing compounds are particularly preferably used in the present invention. That is, it is particularly preferable that the above-mentioned at least one element selected from the group consisting of elements of the Groups 8 to 12 is palladium.

Examples of the above-mentioned palladium-containing compounds include divalent palladiums typified by palladium carboxylates such as palladium acetate and palladium trifluoroacetate, palladium nitrate, palladium sulfate, palladium chloride, palladium bromide, palladium iodide, palladium hydroxide, tetrakis(acetonitrile)palladium tetrafluoroborate, palladiums containing an organic ligand coordinated to the palladium via oxygen such as bis(acetylacetonato)palladium, bis(acetonitrile)palladium chloride, bis(benzonitrile)palladium chloride, palladiums containing an organic ligand coordinated to the palladium by unsaturated bond such as dichloro (octadiene) palladium, sodium tetrachloropalladium, potassium tetrachloropalladium, palladiums containing an organic ligand coordinated to the palladium by nitrogen atom, nitrogen atom-containing organic compound-coordinated palladium, nitro group and/or nitroso group-coordinated palladium, and palladium oxide; monovalent palladiums typified by [Pd$_4$(CO)$_4$(OAc)$_4$].2AcOH; and zero-valent palladiums typified by tris(dibenzylideneacetone)dipalladium, tetrakis(triphenylphosphine)palladium, and palladium black. The above-mentioned palladium may be trivalent or tetravalent palladiums. As the above-mentioned palladium-containing compounds, particularly preferable are palladium carboxylates such as palladium acetate and palladium trifluoroacetate, palladium chloride, palladium nitrate, palladiums containing an organic ligand coordinated to the palladium via oxygen such as bis(acetylacetonate)palladium, palladiums containing an organic ligand coordinated to the palladium by unsaturated bond such as dichloro(octadiene)palladium, sodium tetrachloropalladium, potassium tetrachloropalladium, and [Pd$_4$(CO)$_4$(OAc)$_4$].2AcOH. Selection of a ligand permits arbitrary adjustment of an oxidation-reduction potential or an electron state and an electron orbital energy level of palladium, and therefore a catalyst suitable for the reaction can be designed. Therefore, a catalyst with a high activity, which needs no promoter, can be produced. If palladium has a ligand, the ligand may be a monodentate ligand or may be a multidentate ligand such as bidentate or higher ligands. If palladium having an chiral ligand is used as a catalyst, α-methylene-γ-butyrolactones having an chirality at the β position and/or γ position may be produced.

One or two or more species of the above-mentioned catalysts may be used and may be added in one portion at the start of the reaction or may be successively added during the reaction.

The above-mentioned compound including at least one element selected from the group consisting of elements of the Groups 8 to 12 may be supported on a porous carrier, and one or two or more different supported elements may be used. Examples of the porous carrier include organic compounds typified by activated carbon, activated carbon subjected to oxidation treatment by concentrated nitric acid and the like, carbon black, carbon black subjected to oxidation treatment by concentrated nitric acid and the like, graphite, fullerene, carbon nanotube, carbon nanohorn, carbon nanocoil, carbon molecular sieves, ion-exchange resin, ion-exchange resin which support carboxylic acid, ion-exchange resin which support carboxylic acid containing electron-withdrawing group, and dendrimer; oxides or sulfides typified by silica, porous silica, aluminum oxide, magnesium oxide, barium oxide, titanium oxide, zirconium oxide, vanadium oxide, chrome oxide, manganese oxide, iron oxide, copper oxide, zinc oxide, zinc sulfide, tin oxide, and cerium oxide; composite oxides typified by polyoxometalate, polyoxometalate-containing compound, montmorillonite, apatite, hydrotalcite, kieselguhr, clay compound, zeolite, mesoporous body, silica-alumina, silica-titanium oxide, titanium oxide-zirconium oxide, and aluminum phosphate; and organic-inorganic composite compounds typified by silica which surface is organically modified and organic-inorganic hybrid compound. The carrier may be in fine particle, powder, grain, granule, pellet, extruded, or ring form. A surface treatment by an organic group may be performed using silicon-containing compounds and the like. An oxidization treatment and/or a reduction treatment may be performed for the above-mentioned compound including at least one element selected from the group consisting of elements of the Groups 8 to 12 during, before, and/or after being supported. The above-mentioned compound including at least one element selected from the group consisting of elements of the Groups 8 to 12 may be supported on a carrier in any of forms of uniform, egg shell, egg white, and egg yolk.

It is preferable in the above-mentioned embodiment in which the catalyst is supported on a carrier that the above-mentioned catalyst comprises a compound including at least one element selected from the group consisting of elements of the Groups 8 to 12 and an element other than the elements of the Groups 8 to 12.

If such a catalyst is used as the above-mentioned catalyst, generation of acyclic unsaturated compounds can be more sufficiently suppressed and the yield of the desired cyclic unsaturated compound can be improved.

Examples of the method of supporting the above-mentioned compound including at least one element selected from the group consisting of elements of the Groups 8 to 12 on the above-mentioned carrier include a precipitation method, a coprecipitation method, a kneading method, a gelation method, a deposition method, an impregnation method (an equilibrium adsorption method, an evaporation to dryness method, a dry impregnation method), an ion exchange method, a fusion method, an eluted method, a hydrothermal synthesis method, and a vacuum deposition method. If the catalyst is supported on the carrier in liquid phase, the pH or the temperature of the liquid may be appropriately determined depending on the carrier or the supporting method to be used. The pH is preferably 0.05 or more and 13.9 or less. The temperature is preferably −20° C. or more and 200 ° C. or less. Two or more different elements among the elements of the Groups 8 to 12 maybe used, or one or more elements other than the elements of the Groups 8 to 12 may be supported on the carrier to be coexistent with the element of the Groups 8 to 12. The supported elements may exist at the same site or may separately exist. Alternatively, such elements may be alloyed. The element other than the elements of the Groups 8 to 12 may be supported on the carrier before or after supporting the above-mentioned compound including at least one element selected from the elements of the Groups 8 to 12, or these elements may be simultaneously supported. When the elements are supported, compounds, for example, acid, base, coordinating compounds such as ethylenediaminetetraacetic acid, surfactants, buffers, other additives which are needed for or advantageously acts on the support, and the like may be coexist. Operations such as filtration, rinsing, dryness, heat treatment, calcination, oxidation treatment, and reduction treatment may be performed and such operations may be performed in combination, before, after, or while the above-mentioned compound including at least one element selected from the group consisting of element of the Groups 8 to 12 is supported. It is preferable that one or two or more species of iron, ruthenium, rhodium, iridium, nickel, palladium, platinum, copper, silver, gold, and zinc are used as the above-mentioned elements of the Groups 8 to 12. More preferably, at least palladium is used, and most preferably, substantially only palladium is used. Iron, ruthenium, rhodium, iridium, copper, silver, gold, and zinc may be coexistent with palladium. The amount of the supported element of the Groups 8 to 12 is preferably 0.00001% by weight or more and 900% by weight or less relative to 100% by weight of the carrier, and more preferably 0.0001% by weight or more and 800% by weight or less, and still more preferably 0.001% by weight or more and 600% by weight or less.

The above-mentioned element other than the elements of the Groups 8 to 12 is not especially limited, and one or two or more species may be used. Preferable are lithium, sodium, potassium, rubidium, cesium, magnesium, calcium, barium, scandium, yttrium, lanthanoid, titanium, zirconium, hafnium, vanadium, niobium, chromium, molybdenum, tungsten, manganese, rhenium, boron, aluminum, gallium, indium, thallium, silicon, germanium, tin, lead, nitrogen, phosphorus, arsenic, antimony, bismuth, sulfur, selenium, tellurium, chlorine, bromine, and iodine. More preferable are lithium, sodium, potassium, magnesium, calcium, barium, lanthanoid, titanium, zirconium, vanadium, niobium, molybdenum, tungsten, manganese, boron, aluminum, gallium, indium, thallium, germanium, tin, lead, phosphorus, arsenic, antimony, bismuth, sulfur, selenium, tellurium, and iodine are preferable. The amount of the supported element is preferably 0.000001% by weight or more and 1000000% by weight or less, and more preferably 0.00001% by weight or more and 100000% by weight or less, and still more preferably 0.0001% by weight or more and 90000% by weight or less, relative to 100% by weight of the element of the Groups 8 to 12. If the element other than the elements of the Groups 8 to 12 coexists with the element of the Groups 8 to 12, effects such as granulation, crystallization, alloying, change in valence, change in state, change in contact with the carrier of the supported elements, sintering suppression and the like, are exhibited. As a result, effects such as improvement in catalyst activity or lifetime, suppression of leaching of the supported elements are exhibited, and such effects preferable as a catalyst are exhibited.

It is further preferable that the above-mentioned element other than the elements of the Groups 8 to 12 is at least one element selected from the group consisting of alkali metal elements, alkali earth metal elements, and elements of the Groups 13 to 17.

The temperature in the above-mentioned dryness, heat treatment, and calcination is preferably 60° C. or more and 1000° C. or less, and more preferably 80° C. or more and 800° C. or less, and still more preferably 100° C. or more and 600° C. or less. The time for such treatment is preferably 10 minutes or more and 60 hours or less, and more preferably 30 minutes or more and 50 hours or less, and still more preferably 1 hour or more and 48 hours or less. The dryness, heat treatment, and calcination may be performed under any atmosphere of air, nitrogen, oxygen-containing nitrogen, argon, hydrogen, hydrogen-containing nitrogen, and water-containing gas. Due to such dryness, heat treatment, and calcination operations, effects such as granulation, crystallization, alloying, change in valence, change in state, change in contact with the carrier of the supported elements, sintering suppression and the like, are exhibited. As a result, effects such as improvement in catalytic activity or lifetime, suppression of leaching of the supported elements are exhibited, and such effects preferable as a catalyst are exhibited. The same dryness, heat treatment, and calcination operations are performed for the deteriorated catalyst, and thereby the catalyst can be reactivated. If a palladium-supported catalyst is used, the dryness, the heat treatment, and the calcination method are appropriately selected and thereby the form, the valence, the crystal system, or the particle diameter (maximum distribution diameter) of the palladium multi-nuclear compound can be adjusted. As a result, the catalytic activity is improved. The change in valence can be identified by X-ray Photoelectron Spectroscopy (XPS); the change in the crystal system by X-ray diffraction analysis such as XRD; and the change in particle diameter (maximum distribution diameter) by Scanning Electron Microscope (SEM), Transmission Electron Microscope (TEM), and the like.

The above-mentioned oxidation treatment may be vapor phase oxidation and/or liquid phase oxidation. Preferably used are air, molecular oxygen, molecular oxygen diluted with nitrogen, argon, or the like, ozone, organic peroxide such as peracetic acid, and t-butyl hydroperoxide, peroxides such as hydrogen peroxide and oxone, organic oxides such as benzoquinone, metal oxides such as manganese dioxide, and mineral acids such as nitric acid and sulfuric acid. One or two or more species of them may be used. More preferable are air, molecular oxygen, molecular oxygen diluted with nitrogen, argon, and the like, hydrogen peroxide, and mineral acids such as nitric acid and sulfuric acid. The oxidation treatment temperature is preferably 0° C. or more and 1000° C. or less, and more preferably 20° C. or more and 800° C. or less, and still more preferably 30° C. or more and 600° C. or less. The oxidation treatment time is preferably 10 minutes or more and 60 hours or less, and more preferably 30 minutes or more and 50 hours or less, and still more preferably 1 hour or more and 48 hours or less. Due to such oxidation treatment operation, effects such as granulation, crystallization, alloying, change in valence, change in state, change in contact with the carrier of the supported elements, sintering suppression, are exhibited. As a result, effects such as improvement in catalytic activity or lifetime, suppression of by product generation, suppression of leaching of the supported elements are exhibited, and such effects preferable as a catalyst are exhibited. The same oxidation treatment operation is performed for the deteriorated catalyst, and thereby the catalyst can be reactivated. If a palladium-supported catalyst is used, for example, the oxidation treatment gets the palladium supported on the carrier to be in a monovalent to tetravalent state and/or a positively charged state rather than a zero-valent state, and the change in valence, particle diameter (maximum distribution diameter), or the like improves the catalytic activity, and thereby generation of byproducts can be suppressed without leaching of the catalyst components.

The above-mentioned reduction treatment may be gas phase reduction and/or liquid phase reduction. Hydrogen, hydrogen diluted with nitrogen, argon, or the like, formaldehyde, formalin, hydrazine, methanol, ethanol, propanol, butanol, pentanol, hexanol, organic substances such as hydrocarbon, inorganic substances such as lithium borohydride, sodium borohydride, and lithium aluminum hydride are preferably used. One or two or more species of them may be used. The reduction may be performed only through the heat treatment. More preferable are hydrogen, hydrogen diluted with nitrogen, argon, or the like, hydrazine, methanol, ethanol, propanol, sodium borohydride, and lithium aluminum hydride. The reduction treatment temperature is preferably 0° C. or more and 1000° C. or less, and more preferably 20° C. or more and 800° C. or less, and still more preferably 30° C. or more and 600° C. or less. The reduction treatment time is preferably 10 minutes or more and 60 hours or less, and more preferably 30 minutes or more and 50 hours or less, and still more preferably 1 hour or more and 48 hours or less. Due to such reduction treatment operation, effects such as granulation, crystallization, alloying, change in valence, change in state, change in contact with the carrier of the carried elements, and sintering suppression, are exhibited. As a result, effects such as improvement in catalytic activity or lifetime, suppression of byproduct generation, and suppression of leaching of the supported elements are exhibited, and such effects preferable as a catalyst are exhibited. The same reduction treatment operation is performed for the deteriorated catalyst, and thereby the catalyst can be reactivated. If a palladium-supported catalyst is used, for example, the form or the particle diameter (maximum distribution diameter) of the palladium multi-nuclear compound can be adjusted due to the reduction treatment method, and thereby the catalytic activity is improved and generation of byproducts can be suppressed without leaching of the catalyst components.

The above-mentioned catalyst in the production method of the present invention may be a mononuclear or multi-nuclear compound regardless of a homogeneous or heterogeneous catalyst. A mononuclear compound or a multi-nuclear compound previously prepared may be used as the catalyst. Alternatively, a catalyst not containing a mononuclear compound or a multi-nuclear compound at the start of the reaction generates a mononuclear compound or a multi-nuclear compound during the reaction and such a generated mononuclear or multi-nuclear compound may function as the catalyst. As mentioned above, in the present description, the above-mentioned catalyst means not only a substance which exists in the same state as the state at the start of the reaction even after completion of the reaction, but also a substance which exists in a state different from that at the start of the reaction after the completion of the reaction, as long as the substance has a function of increasing a reaction rate. In the multi-nuclear compound, regardless of a homogeneous or heterogeneous catalyst, the metal elements maybe bonded to each other, and the metal elements may be cross-linked and bonded through an oxygen atom, an oxygen-containing compound such as carboxylate, a chalcogen-containing compound, a halogen-containing compound, aluminum, boron, water. Alternatively, the metal elements may be alloyed. Examples of particularly preferable combinations in the multi-nuclear compound include palladium-copper, palladium-platinum, palladium-silver, palladium-gold, palladium-boron, palladium-aluminum, palladium-tin, palladium-lead, palladium-arsenic, palladium-antimony, palladium-bismuth, palladium-selenium, and palladium-tellurium such as $Pd_{20}Te_6$ and $Pd_{20}Te_4$, rhodium-copper, rhodium-palladium, rhodium-platinum, rhodium-silver, rhodium-gold, rhodium-boron, rhodium-aluminum, rhodium-tin, rhodium-lead, rhodium-arsenic, rhodium-antimony, rhodium-bismuth, rhodium-selenium, rhodium-tellurium, ruthenium-copper, ruthenium palladium, ruthenium-platinum, ruthenium-silver, ruthenium-gold, ruthenium-boron, ruthenium-aluminum, ruthenium-tin, ruthenium-lead, ruthenium-arsenic, ruthenium-antimony, ruthenium-bismuth, ruthenium-selenium, ruthenium-tellurium, nickel-copper, nickel-palladium, nickel-platinum, nickel-silver, nickel-gold, nickel-boron, nickel-aluminum, nickel-tin, nickel-lead, nickel-arsenic, nickel-antimony, nickel-bismuth, nickel-selenium, and nickel-tellurium. The nuclei of the multi-nuclear compound may be the same or different. If the nuclei are different, three or more species may exist. Formation of such multi-nuclear compounds improves the reoxidation efficiency of the catalyst and the catalyst can be easily maintained to be in a high oxidation state, and thereby the reaction activity is considered to be improved.

One or two or more species of the above-mentioned catalysts may be used and such catalysts as well as a promoter may be added in one portion before the reaction or may be successively added during the reaction.

The above-mentioned multi-nuclear compound exists in the reaction system, and the compound itself may exhibit the catalyst function, or may exhibit a function as a promoter, or a function as a site or surface where the reaction proceeds. Compounds leaching from the multi-nuclear compound may serve as a substantial catalyst. Substantially every catalyst may be a multi-nuclear compound.

It is preferable that the above-mentioned multi-nuclear compound in the production method of the present invention has a maximum distribution diameter of 10 nm or less, and particularly preferably 6 nm or less if the reaction system is a homogeneous and/or pseudo-homogeneous system. It is particularly preferable that the above-mentioned multi-nuclear compound has a maximum distribution diameter of 5 nm or less.

In order for the above-mentioned multi-nuclear compound to have a maximum distribution diameter of 5 nm or less, a species of the solvent or a concentration of the catalyst in the solvent is adjusted, or amide solvents such as N-methylpyrrolidone, N-ethylpyrrolidone, N-cyclohexylpyrrolidone, N,N-dimethylformamide, and N,N-dimethylacetamide, carbonate solvents, ionic liquid, solvents containing polyvinylpyrrolidone, surfactant, and the like, are particularly preferably used, for example. These solvents can stabilize the multi-nuclear compound and suppress aggregation, and suppress the multi-nuclear compound from precipitating as palladium black as much as possible. Therefore, the multi-nuclear compound can have a maximum distribution diameter of 5 nm or less. Simultaneously, these solvents are not strongly coordinated to the multi-nuclear compound and therefore the catalytic active site can be maintained. As a result, high catalytic activity is exhibited and the yield of the cyclic unsaturated compound is increased.

The multi-nuclear compound means a compound including two or more elements of the Groups 8 to 12 in a unit structure or in a comparable structure. The maximum distribution diameter of the multi-nuclear compound is a particle diameter corresponding to the peak of a particle diameter distribution of a multi-nuclear compound when a reaction mixture during and/or after the reaction is analyzed by Small Angle X-ray Scattering (SAXS) method. Palladium black which obviously precipitates on a wall surface or bottom of a reaction container is not taken into account. The multi-nuclear compound having a particle diameter of 20 nm or more can be identified with a Scanning Electron Microscope (SEM), a Transmission Electron Microscope (TEM), and the like. The multi-nuclear compound having a particle diameter of 1 nm or less can be identified by X-ray crystal structure analysis and the like. In the multi-nuclear compound, the metal elements are bonded to each other or may be cross-linked and bonded through an oxygen atom, an oxygen-containing compound such as carboxylate, a chalcogen-containing compound, a halogen-containing compound, and water.

In the above-mentioned production method of the present invention, the catalyst may be supported on a carrier.

If the above-mentioned catalyst is supported on a carrier, the reaction system can be not a homogeneous system but a heterogeneous or suspension system. That is, the reaction according to the production method of the present invention can be performed not in a homogeneous system but in a heterogeneous or suspension system.

The above-mentioned carrier is not especially limited, but the above-mentioned porous carriers can be preferably used. Among them, carriers containing carbon, silica, and the like, are particularly preferable.

The above-mentioned supported catalyst is not especially limited, and supported catalysts in accordance with the above-mentioned preferable embodiments can be preferably used. For example, an embodiment in which the above-mentioned supported catalyst is a multi-nuclear compound is preferable.

The above-mentioned "supported" is not especially limited, and includes an embodiment in which the above-mentioned catalyst contacts with the carrier surface, an embodiment in which the above-mentioned catalyst contacts with a pore of the carrier, and an embodiment in which these embodiments are combined.

According to the above-mentioned embodiment in which the catalyst is supported on the carrier, advantageous effects of the present invention, in which sufficient excellent reaction rate and yield of the cyclic unsaturated compound can be permitted and generation of byproducts can be suppressed, can be sufficiently exhibited. Recovery of the catalyst after completion of the reaction, and recycling and reprocessing operations can be simply performed. If the catalyst activity is reduced, recalcination, or a step of once dissolving the catalyst component into a solvent such as water, an acid aqueous solution, a basic aqueous solution, and an organic solvent and then supporting the catalyst component on the carrier again through the same operations, is performed. It is preferable that substantially every catalyst is supported on the carrier. The leaching component of catalyst can be recovered by an ion-exchange resin and the like.

According to the above-mentioned embodiment in which the catalyst is supported on the carrier in the production method of the present invention, it is preferable that the above-mentioned catalyst has an embodiment in which the above-mentioned compound including at least one element selected from the group consisting of elements of the Groups 8 to 12 is supported on the carrier. It is more preferable that the above-mentioned catalyst has an embodiment in which the multi-nuclear compound containing above-mentioned element is supported. The maximum distribution diameter of the multi-nuclear compound is preferably 0.1 to 200 nm. That is, if the catalyst is supported on the carrier, it is preferable that the maximum distribution diameter of the above-mentioned catalyst is 0.1 to 200 nm. The above-mentioned lower limit is preferably 0.2 nm and more preferably 0.5 nm. The above-mentioned upper limit is more preferably 180 nm and still more preferably 150 nm. The maximum distribution diameter of the multi-nuclear compound (catalyst) is a particle diameter corresponding to the peak of a particle distribution when 100 multi-nuclear compounds (catalyst) observed through analysis with a scanning electron microscope (SEM) are randomly extracted and measured for particle diameter. In the multi-nuclear compound, the metal elements may be bonded to each other or may be cross-linked and bonded through an oxygen atom, an oxygen-containing compound such as carboxylate, a chalcogen-containing compound, a halogen-containing compound, aluminum, boron, water, and the like. Some and/or all of the elements forming the multi-nuclear compound may be oxides and have different valences. Some of the elements forming the multi-nuclear compound may be positively and/or negatively charged. The above-mentioned SEM analysis is preferably performed before the reaction, for example.

According to the production method of the present invention, it is preferable that the method comprises a step of reacting the $\alpha,\beta$-unsaturated carboxylic acid with the unsaturated organic compound in the presence of a basic compound. Particularly, it is preferable that the production method of the present invention includes a step of reacting the $\alpha,\beta$-unsaturated carboxylic acid with the unsaturated organic compound in the presence of a basic compound, in the embodiment in which the above-mentioned cyclic unsaturated compound is a compound containing a double bond and the double bond exists at the exo position and/or the endo position.

Due to the presence of the above-mentioned basic compound, a carboxyl group of the $\alpha,\beta$-unsaturated carboxylic acid forms a carboxylate anion, and the reactivity with the unsaturated organic compound can be increased. As a result, it may be possible that the reaction rate of the production method of the present invention and the yield of the cyclic unsaturated compound can be increased, or a catalytic active species effective for this reaction or an intermediate for generating the active species can be generated (for example, a trimer structure of palladium acetate is decomposed into a dimer structure or a monomer structure). Such a production method of the present invention can be usefully applied to industrial production.

The above-mentioned basic compound is a Broensted base and Lewis base. The above-mentioned basic compound is not especially limited as long as it has no harmful effects on the reaction. Compounds containing an alkali metal and/or an alkali earth metal, oxides, hydroxides, ammonia, amino group-containing organic compounds, imino group-containing organic compounds and the like, are preferable. One or two or more species of them may be used. Preferable examples thereof include alkali metal and/or alkali earth metal-containing compounds typified by lithium carbonate, lithium hydroxide, lithium acetate, lithium acrylate, sodium carbonate, sodium hydrogencarbonate, sodium hydroxide, sodium acetate, sodium acrylate, potassium carbonate, potassium hydrogencarbonate, potassium hydroxide, potassium acetate, potassium acrylate, cesium carbonate, cesium hydroxide, cesium acetate, cesium acrylate, magnesium carbonate, magnesium hydroxide, magnesium acetate, magnesium acrylate, calcium carbonate, calcium hydroxide, calcium acetate, calcium acrylate, barium carbonate, barium hydroxide, barium acetate, barium acrylate, lithium oxide, sodium oxide, potassium oxide, cesium oxide, magnesium oxide, calcium oxide, and barium oxide, titanium hydroxide, titanium oxide, zirconium hydroxide, zirconium oxide, iron hydroxide, zinc hydroxide, aluminum hydroxide, aluminum oxide, silica gel, molecular sieves, zeolite, clay compound, hydrotalcite, ion-exchange resin, polyoxometalate, ammonia, pyridine, piperidine, N-substituted piperidine, pyrrole, pyrrolidine, N-substituted pyrrolidine, trimethylamine, triethylamine, tributylamine, aniline, N-substituted aniline, N-alkylidene-substituted amine, N-benzylidene-substituted amine, Schiff base, N-alkylidene-substituted amide, and N-benzylidene-substituted amide.

It is particularly preferable that the basic compound includes an alkali metal and/or an alkali earth metal.

If the above-mentioned basic compound includes an alkali metal and/or an alkali earth metal, the reaction rate and the yield of the cyclic unsaturated compound can be further improved.

It is preferable that substantially every basic compound contains an alkali metal and/or an alkali earth metal. According to the above-mentioned embodiment in which the catalyst is supported on the carrier, the above-mentioned basic compound may be supported on the carrier and used.

The above-mentioned basic compound is preferably 0.00001 mol % or more and 100000 mol % or less relative to 100 mol % of the $\alpha,\beta$-unsaturated carboxylic acid. The upper limit is more preferably 50000 mol %, and still more preferably 20000 mol %, and furthermore preferably 10000 mol %. The lower limit is more preferably 0.0001 mol %, and still more preferably 0.0005 mol %, and furthermore preferably 0.001 mol %.

The above-mentioned basic compound is preferably 0.000001 mol % or more and 1000000 mol % or less, relative to 100 mol % of the unsaturated organic compound. The upper limit is more preferably 500000 mol %, and still more preferably 200000 mol %, and furthermore preferably 100000mol %. The lower limit is more preferably 0.00001 mol %, and still more preferably 0.00005mol %, and furthermore preferably 0.0001 mol %.

The preferable embodiments of the present invention include a method for producing a cyclic unsaturated compound by reacting an $\alpha,\beta$-unsaturated carboxylic acid with an unsaturated organic compound, wherein the method includes a step of reacting the α,β-unsaturated carboxylic acid with the unsaturated organic compound in the presence of a solvent.

The above-mentioned preferable embodiments and the embodiment in which the reaction is performed in the presence of a solvent may be appropriately combined and employed. That is, it is preferable that the production method of the present invention includes a step of reacting the α,β-unsaturated carboxylic acid with the unsaturated organic compound in the presence of a solvent.

If the above-mentioned production method includes a step of reacting the α,β-unsaturated carboxylic acid with the unsaturated organic compound in the presence of a solvent, generation of acyclic unsaturated compounds can be sufficiently suppressed and the yield and the generation rate of the cyclic unsaturated compound can be increased. Such a method for producing the cyclic unsaturated compound according to the present invention can be effectively applied to industrial production. The reason of this may be mentioned as follows. The coordination environment or the electron state around the metal is changed. Such changes cause oxymetalation of the α,β-unsaturated carboxylic acid into a double bond or a triple bond of the unsaturated organic compound, and thereby the following β-hydride elimination is suppressed. As a result, coordination of unsaturated bond derived from the α,β-unsaturated carboxylic acid to the metal and the insertion reaction proceed with efficiency, which permits easier generation of cyclic unsaturated compounds. Some other functions of solvents are that assist for generation and stabilization of a catalytic active species effective for production of the cyclic unsaturated compounds (for example, mononuclear palladium species, heteronuclear palladium species, multi-nuclear palladium species, palladium cluster, palladium nanoparticle, palladium-containing metal nanoparticle, and the like); improvement of activity of the catalytic active species; permission to proceed easier reoxidation; and increase of an oxygen concentration in the solution. Thereby, the production method of the present invention has an advantage for increasing the oxidation number of the catalyst active species (refer to FIGS. 1 and 2).

The above-mentioned solvent is not especially limited unless the reaction is inhibited. Hydrocarbon, aromatic hydrocarbon, alcohol, aldehyde, ketone, carboxylic acid, ester, ether, nitrile, sulfide, sulfoxide, amine, amide, imide, a halogen-containing compound, carbonate, ionic liquid, and the like, may be used. If the α,β-unsaturated carboxylic acid and/or the unsaturated organic compound are/is liquid at a reaction temperature, these substrates can be used as a solvent. If an heterogeneous catalyst and/or a suspension system catalyst are/is used, the above-mentioned solvent may be used, or if the α,β-unsaturated carboxylic acid and/or the unsaturated organic compound are/is liquid at a reaction temperature, it is more preferable that these substrates are used as the solvent. If an heterogeneous catalyst and/or a suspension system catalyst are/is used, the desired cyclic unsaturated compound of the present invention can be obtained with yield even if these substrates are used as the solvent and operations of removing the solvent other than the above-mentioned substrates by distillation and the like are not needed, which is different from the case where a homogeneous catalyst and/or a pseudo-homogeneous catalyst are/is used. In such points, the use of these substrates as the solvent is preferable.

Preferable examples of the above-mentioned solvent include hydrocarbon, aromatic hydrocarbon, alcohol, aldehyde, ketone, carboxylic acid, ester, ether, nitrile, sulfoxide, amine, amide, a halogen-containing compound, carbonate, and ionic liquid. Examples of the solvent include pentane, cyclopentane, hexane, cyclohexane, heptane, octane, cyclooctane, nonane, decane, undecane, dodecane, benzene, toluene, xylene, trimethyl benzene, methanol, ethanol, n-propanol, isopropanol, butanol, t-butanol, pentanol, hexanol, cyclohexanol, heptanol, octanol, ethylene glycol, polyethylene glycol, acetaldehyde, propanal, butanal, isobutanal, pentanal, hexanal, heptanal, octanal, acetone, methyl ethyl ketone, formic acid, acetic acid, propionic acid, butanoic acid, pentanoic acid, hexanoic acid, heptanoic acid, octanoic acid, acrylic acid, methacrylic acid, methyl acetate, ethyl acetate, butyl acetate, methyl acrylate, ethyl acrylate, butyl acrylate, cyclohexyl acrylate, 2-ethylhexyl acrylate, 2-hydroxyethyl acrylate, methyl methacrylate, ethyl methacrylate, butyl methacrylate, cyclohexyl methacrylate, 2-ethylhexyl methacrylate, 2-hydroxyethyl methacrylate, lactone, dimethoxyethane, dioxane, tetrahydrofuran, polyethylene glycol ether, acetonitrile, benzonitrile, dimethyl sulfoxide, pyridine, lutidine, triethylamine, tributylamine, ethanolamine, diethanolamine, triethanolamine, dimethylethanolamine, tetramethyldiethanolamine, hexamethyltriethanolamine, formamide, acetamide, pyrrolidone, imidazolidinone, acrylamide, N,N-dimethylformamide, N,N-dimethylacetamide, N-methylpyrrolidone, N-vinylpyrrolidone, N-ethylpyrrolidone, N-cyclohexylpyrrolidone, 1,3-dimethyl-2-imidazolidinone, N,N-dimethylacrylamide, methylene chloride, chloroform, dichloroethane, carbon tetrachloride, carbonate, and ionic liquid. One or two or more species of them may be used. For example, if a solvent which can coordinate weakly to the catalyst, such as hydrocarbon and aromatic hydrocarbon, is used, the reoxidation step efficiently proceeds and an opportunity where the substrate, the promoter, the reoxidant agent and the like, are coordinated to the catalyst or an opportunity where the insertion reaction proceeds is significantly increased, and thereby the reaction rate is improved. Therefore, such a solvent is preferably used. In addition, if a solvent having a capability of being moderately coordinated to the catalyst metal or stabilizing the multinuclear compound that is a catalytic active site, such as amide, carbonate, ionic liquid, is used, the desired cyclic unsaturated compound is preferentially generated. Therefore, the use of such a solvent is more preferable. In order to suppress generation of byproducts such as unsaturated organic compound dimer, the solvent may be used to adjust the substrate concentration or increase the solubility of the substrate or the reoxidant agent in the reaction solution.

It is preferable that the above-mentioned solvent includes no sulfoxide compounds. That is, it is more preferable that no sulfoxide compounds exist in the solvent. If a sulfoxide solvent such as dimethylsulfoxide is used, the reaction activity may be greatly reduced depending on the substrate. Further, it is preferable that the above-mentioned solvent includes no amine compounds. That is, it is more preferable that no amine compounds exist in the solvent. If the amine compound excessively exits in the solvent, the amine compound is strongly coordinated to the catalytic active site, thereby reducing the reactivity, in some cases.

It is more preferable in the production method of the present invention that the above-mentioned solvent essentially includes any of hydrocarbon compounds, aromatic hydrocarbon compounds, and nitrogen-containing compounds. These compounds are used as the above-mentioned solvent. Pentane, cyclopentane, hexane, cyclohexane, heptane, octane, cyclooctane, nonane, decane, undecane, dodecane, and the like are particularly preferable as the hydrocarbon compounds. Benzene, toluene, xylene, trimethylbenzene, and the like, are preferable as the aromatic hydrocarbon compounds. Solvents including a nitrile group and/or an amide group in the molecule are still more preferable as the above-mentioned nitrogen-containing compounds. Particularly preferable are acetonitrile, benzonitrile, formamide, acetamide, pyrrolidone, imidazolidinone, acrylamide, N,N-dimethylformamide, N,N-dimethylacetamide, N-methylpyrrolidone, N-vinylpyrrolidone, N-ethylpyrrolidone, N-cyclohexylpyrrolidone, 1,3-dimethyl-2-imidazolidinone, and N,N-dimethyl acrylamide.

If such a solvent is used as the above-mentioned solvent, a value (A/B) of a cyclic unsaturated compound (A) to a acyclic unsaturated compound (B), that is, a selectivity of a desired cyclic unsaturated compound (for example, α-methylene-γ-butyrolactone) to a acyclic unsaturated compound, or the reaction rate and the yield are significantly improved.

Only one species may be used or two or more species may be appropriately combined and used as the above-mentioned solvent. The kind and the use amount thereof may be appropriately determined depending on the substrate or the catalyst.

The amount of the α,β-unsaturated carboxylic acid to the volume of the above-mentioned solvent is preferably 0.001 to 1000000 mol/l. The upper limit is more preferably 100000 mol/l, and still more preferably 10000 mol/l. The lower limit is more preferably 0.005 mol/l, and still more preferably 0.01 mol/l.

The amount of the unsaturated organic compound to the volume of the above-mentioned solvent is preferably 0.0001 to 1000000 mol/L. The upper limit is more preferably 500000 mol/L, and still more preferably 100000 mol/L. The lower limit is more preferably 0.0005 mol/L, and still more preferably 0.001 mol/L.

It is preferable in the production method of the present invention that the method comprises a step of reoxidizing the catalyst using a reoxidant agent. The preferable embodiments of the present invention include a method for producing a cyclic unsaturated compound by reacting an α,β-unsaturated carboxylic acid with an unsaturated organic compound in the presence of a catalyst, wherein the method comprises a step of reoxidizing the catalyst.

The preferable embodiments of the present invention include a method for producing a cyclic unsaturated compound by intermolecular reaction between an α,β-unsaturated carboxylic acid and an unsaturated organic compound in the presence of a catalyst, wherein the method comprises a step of reoxidizing the catalyst using a reoxidant agent.

The above-mentioned preferable embodiments and the embodiment in which the catalyst is reoxidized may be appropriately combined and employed. That is, it is preferable that the production method of the present invention includes a step of reoxidizing the catalyst using a reoxidant agent.

The above-mentioned reoxidation means that during or after the reaction, the reduced component of the catalyst is oxidized to be in a state before the reduction or an oxidation state similar to the state before the reduction. That is, it means that a catalytic active species with a low oxidation number, which were generated in the reaction steps by reducing a catalytic active species with a high oxidation number, preferably a catalytic active species with a high oxidation number contained in the compound including at least one element selected form the group consisting of elements of the Groups 8 to 12, is oxidized again to be a catalytic active species with a high oxidation number. If palladium is used as the catalyst, the above-mentioned reoxidation means that monovalent to tetravalent palladium species or slightly positively charged palladium species is reduced to have a lower valence in the reaction steps, and the reduced palladium species is oxidized again to be in the original state or have the original valence, or to be in a state similar to the original state or have a valence similar to the original valence. The above-mentioned reoxidant agent means an oxidizing agent for performing the reoxidation of the catalyst. A reaction pathway where the reaction proceeds while the catalyst maintains the high oxidation number and the high oxidation state without reducing the oxidation number or turning into the low oxidation state maybe mentioned in view of the reaction mechanism. Therefore, the reoxidant agent herein used includes agents having a function of maintaining the above-mentioned high oxidation number or high oxidation state.

The above-mentioned reoxidant agent is not especially limited as long as it has no harmful effects on the reaction. Organic reoxidant agents and/or inorganic reoxidant agents may be used, and one or two or more species of them may be used. The organic reoxidant agent means an oxidizing agent which contains no metal elements or semi-metal elements and is mainly composed of carbon, and the inorganic reoxidant agent means an oxidizing agent which is composed of elements other than carbon or an oxidizing agent which includes at least one metal element or semi-metal element. Organic ligand-containing metal compounds or semi-metal compounds are classified into the inorganic reoxidant agent in this description. Among them, quinones, peroxides, oxygen, oxides, transition metal-containing compounds, mineral acids, nitrogen monoxide, and the like are preferable. More preferable are benzoquinone, anthraquinone, 2-(cyclohexylsulfinyl)-benzoquinone, 2-(phenylsulfinyl)-benzoquinone, hydrogen peroxide, aqueous hydrogen peroxide, peracetic acid, t-butyl hydroperoxide, sodium periodate, sodium perchlorate, oxone, air, molecular oxygen, molecular oxygen-containing gas, atomic oxygen, ozone, ruthenium oxide, antimony oxide, bismuth oxide, selenium oxide, tellurium oxide, polyoxometalate, vanadium-containing compounds such as vanadium oxide and vanadyl acetylacetonate, manganese-containing compounds such as manganese dioxide and manganese acetate, iron-containing compounds such as iron oxide, iron nitrate and iron-containing phthalocyanine compounds, cobalt-containing compounds such as cobalt oxide, cobalt-containing porphyrin compounds and cobalt-containing salen compounds, copper-containing compounds such as copper oxide, copper acetate, copper trifluoroacetate, and copper acetylacetonates, hydrochloric acid, nitric acid, sulfuric acid, and nitrogen monoxide. The quinones may be generated in the reaction system, and hydroquinones may be used as a precursor. If a transition metal-containing compound is used, such a compound may exist independently in the reaction system or may form a multi-nuclear compound with the catalyst. The above-mentioned reoxidant agent may be appropriately selected depending on reaction conditions to be employed, and may be added in one portion at the start of the reaction or may be appropriately added during the reaction.

The above-mentioned molecular oxygen may be used also as a polymerization inhibitor in order to adjust the pressure or control the proportion in the gas phase.

In the present description, the molecular oxygen is also referred to as oxygen.

It is particularly preferable that at least oxygen is used as the above-mentioned reoxidant agent. That is, it is particularly preferable that the above-mentioned reoxidant agent includes oxygen as an essential component. The preferable embodiments of the present invention include the method for producing the cyclic unsaturated compound, wherein the method includes a step of reoxidizing the catalyst using at least oxygen as the reoxidant agent. That is, the embodiment in which the production method of the present invention includes a step of reoxidizing the catalyst using a reoxidant agent essentially including molecular oxygen is one of the preferable embodiments of the present invention.

In other words, it is preferable in the production method of the cyclic unsaturated compound of the present invention that molecular oxygen is used as one reoxidant agent in the step of reoxidizing the catalyst. The use of molecular oxygen as one reoxidant agent also includes an embodiment in which the reoxidant agent is composed of substantially only oxygen. It is preferable that the above-mentioned reoxidant agent includes no manganese dioxide except for the case where the reoxidant agent is used also as the carrier. If manganese dioxide is used, a step of removing the manganese dioxide through filtration after the reaction may be needed. The manganese dioxide is generally known as a reoxidant agent which needs no oxygen. According to the production method of the present invention, the reaction is performed in an heterogeneous and/or suspension system in the above-mentioned embodiment in which the catalyst supported on the carrier is used. Therefore, it is most preferable that oxygen is used as the reoxidant agent. If the reaction is performed in an heterogeneous system using oxygen as the reoxidant agent, no operations of removing the above-mentioned reoxidant agent by distillation and the like are needed and such a production method is preferable in terms of handleability, safety, and economical efficiency.

If the method for producing the cyclic unsaturated compound of the present invention includes the step of reoxidizing the catalyst using the reoxidant agent, the catalyst is preferably reoxidized, and thereby oxidation-reduction cycle of the catalyst is efficiently performed or the catalyst can be maintained to be in a high oxidation state. Therefore, generation of acyclic unsaturated compounds can be sufficiently suppressed and the yield of the desired cyclic unsaturated compound can be increased. Therefore, such a production method is effectively used to industrial production. Examples of preferable embodiments of the above-mentioned reoxidation step include an embodiment in which the compound including at least one element selected from the group consisting of elements of the Groups 8 to 12 is reoxidized.

The above-mentioned reoxidation may be performed during the reaction or the reoxidation treatment maybe performed after completion of the reaction. If oxygen is used as one reoxidant agent, it is preferable that one or more species of compounds including at least one element selected from the group consisting of vanadium, molybdenum, tungsten, manganese, iron, ruthenium, cobalt, copper, silver, gold, boron, aluminum, tin, lead, antimony, bismuth, selenium, and tellurium coexists in the system or the catalyst. In this case, the above-mentioned element-containing compound may exist independently in the reaction system or may form a multi-nuclear compound or an alloy with the catalyst. Thus, with respect to the multi-component catalyst, an assistant component having a function of reinforcing the catalytic reaction which a main component independently shows is called promoter. The above-mentioned element-containing compounds can be called promoter in this reaction. The promoter may be appropriately determined depending on the reaction conditions to be employed, and may contain an inorganic substance or an organic substance. More preferable are vanadium, molybdenum, tungsten, manganese, iron, cobalt, copper, silver, gold, antimony, bismuth, selenium, tellurium. That is, it is more preferable that one or more compounds including at least one element selected from the group consisting of vanadium, molybdenum, tungsten, manganese, iron, cobalt, copper, silver, gold, antimony, bismuth, selenium, and tellurium are coexistent in the system or the catalyst. Examples of the form of the above-mentioned compound include an oxide, a polyoxometalate compound, a hydroxide, a halide, an alloy compound, an organic group-containing compound, a salt, an alkali metal salt, and an alkali earth metal salt. More preferable are an oxide, a polyoxometalate compound, a halide, an alloy compound, an organic group-containing compound, and a salt. That is, with respect to the form of the above-mentioned compound, the compound is more preferably at least one selected from the group consisting of oxides, polyoxometalates, halides, alloy compounds, organic group-containing compounds, and salts. The polyoxometalate compound can arbitrarily adjust an oxidation-reduction potential or an electron state and an electron orbital energy level of the element by selection of a constitutional element or a counter cation. In addition, the organic group-containing compound can adjust them by selection of a ligand.

It is preferable that the use amount of the reoxidant agent in the reaction steps is 10000000 mol % or less relative to 100 mol % of the $\alpha,\beta$-unsaturated carboxylic acid, if the catalyst is reoxidized using the organic reoxidant agent, or if the catalyst is reoxidized using the inorganic reoxidant agent, in any reaction systems of a batch system, a semi-batch system, a circulation system (fixed bed and fluid bed), and a reaction system suitable for a diffusion controlled reaction, such as a loop reactor using a high-speed jet. The use amount is more preferably 5000000 mol % or less, and still more preferably 2500000 mol % or less, and still more preferably 1000000 mol % or less, and still more preferably 500000 mol % or less, and most preferably 100000 mol % or less. Further, the use amount is preferably 0.0000001 mol % or more relative to 100 mol % of the $\alpha,\beta$-unsaturatedcarboxylicacid, andmorepreferably 0.0000005 mol % or more, and still more preferably 0.000001 mol % or more and still more preferably 0.00001 mol % or more, and still more preferably 0.00005 mol % or more, and particularly preferably 0.0001 mol % or more. If the use amount is more than 10000000 mol % or less than 0.0000001 mol %, the yield or the selectivity of the desired cyclic unsaturated compound in the production method of the present invention may be reduced. The reoxidant agent may be appropriately added during the reaction depending on the progress of the reaction.

The above-mentioned organic reoxidant agent is not especially limited as long as it is an oxidizing agent which includes no metal elements or semi-metal elements and is mainly composed of carbon, and commonly used organic reoxidant agents may be appropriately used.

If the above-mentioned organic reoxidant agents are used, it is preferable that one of the organic reoxidant agents is benzoquinone.

If the benzoquinone is used, the benzoquinone is coordinated to the catalyst, and an effect of further improving the yield of the cyclic unsaturated compound also can be exhibited.

The present invention is also a method of reoxidizing a reduced catalyst in the presence of a nitrile solvent or a hydrocarbon solvent. This method can be preferably applied to the above-mentioned method for producing the cyclic unsaturated compound of the present invention. Accordingly, it is one of the preferable embodiments of the present invention that this reoxidation method of the catalyst is used in the method for producing the cyclic unsaturated compound of the present invention.

According to the above-mentioned reoxidation method of the catalyst, the solvent is appropriately selected and thereby the catalyst can be efficiently reoxidized substantially without using the organic reoxidant agent. If the catalytic reaction and the reoxidation reaction are simultaneously performed, the catalytic reaction can be efficiently performed at a smaller amount of the catalyst. In such a point, the reoxidation method is preferable and therefore industrially useful. The reoxidation is performed by a reoxidant agent such as oxygen if the catalyst is reoxidized substantially without using the organic reoxidant agent. Such a reoxidation method can applied to methods for producing various organic compounds such as cyclic unsaturated compounds, and can be preferably applied to the method for producing the cyclic unsaturated compound of the present invention. Therefore, such a reoxidation method is industrially effective.

The reason why the cyclic unsaturated compound can be efficiently produced at a smaller amount of the catalyst substantially without using the organic reoxidant agent is mentioned below with reference to one embodiment.

In a catalytic reaction, reduction of catalytic active species (for example, palladium species) takes place from a high oxidation state to a low oxidation state, as shown in FIGS. 1 and 2. In order to proceed the reaction, the catalytic active species needs to be reoxidized.

A catalyst reoxidation mechanism shown in FIG. 3 may be mentioned as a reoxidation reaction mechanism according to the method for reoxidizing the catalyst in the presence of a nitrile solvent.

In order to reoxidize the above-mentioned catalyst active species, organic reoxidant agents are used because oxidation-reduction reaction of the catalyst active species with the organic reoxidant agent easily occurs, generally. However, if a nitrile solvent is used, a nitrile solvent molecule is considered to be coordinated to the catalytic active species (for example, palladium species) via a nitrogen atom of the nitrile group, and thereby aggregation of the catalysts is suppressed. Furthermore, the electron orbital or the oxidation-reduction potential of the catalyst is influenced. As a result, the catalytic active species is easily reoxidized and therefore can be reoxidized without using the organic reoxidant agent. Therefore, the oxidation-reduction cycle can efficiently occur. In this case, as shown in FIG. 3, reoxidation of the catalytic active species can efficiently proceed using only a polyoxometalate as a promoter compound and oxygen as a reoxidant agent, without the oxidation-reduction reaction shown by the dotted line part in FIG. 3. Simultaneously, it is known that a halogen compound is also introduced into the catalyst or the reaction system in order to perform the reoxidation efficiently. However, in the above-mentioned oxidation method, the above-mentioned reoxidation proceeds without using such a halogen compound. Therefore, problems such as corrosion, isomerization of products, halide-containing byproducts, and environmental pollution can be eliminated.

According to the above-mentioned method for reoxidizing the catalyst in the presence of the hydrocarbon solvent, a solvent molecule is not strongly coordinated to the catalyst, and a component which accelerates reoxidation, such as an oxidizing agent, acts on the catalyst without being disturbed by the solvent molecule, and simultaneously the substrate is easily coordinated to the metal. As a result, the reoxidation and the main reaction proceeds efficiently. The following two reaction mechanisms may be mentioned. (1) A reaction mechanism in which a promoter (for example, copper species) functions as a reoxidant agent and reoxidation efficiently occurs (refer to FIG. 5) and (2) a reaction mechanism in which a catalyst forms a multi-nuclear compound (for example, the catalytic active species of the catalyst is a palladium species and the catalytic active species of the promoter is a copper species, that is, a palladium-copper complex), thereby being maintained to be in a state with a high oxidation number, without becoming a reduction state.

In the present description, the reoxidation includes that the above-mentioned catalyst forms a multi-nuclear complex, thereby being maintained to be in a state with a high oxidation number (in an oxidation state).

That is, the catalytic active species is easily reoxidized if the promoter (for example, copper species) functions as the reoxidant agent. If the promoter forms a multi-nuclear complex with the catalyst (for example, a palladium-copper catalyst) and thereby the state with a high oxidation number is maintained, the catalytic active species is not deactivated. In the both cases, the catalyst is sufficiently suppressed from being deactivated by the reduction and becoming zero-valent aggregated particles, and the oxidation-reduction cycle or maintenance of the catalytic active species with a high oxidation number efficiently occurs without using the organic reoxidant agent. Simultaneously, it is known that a halogen compound is also introduced into the catalyst or the reaction system in order to perform the reoxidation efficiently. However, in the above-mentioned oxidation method, the above-mentioned reoxidation proceeds without using such a halogen compound. Therefore, problems such as corrosion, isomerization of products, halide-containing byproducts, and environmental pollution can be eliminated.

Preferable catalysts, conditions and the like in the above-mentioned reoxidation method are the same as those in the production method of the cyclic unsaturated compound of the present invention. For example, it is preferable in the above-mentioned reoxidation method that the above-mentioned catalyst is a palladium-containing compound.

As mentioned above, the above-mentioned reoxidation method of the catalyst can be preferably applied to the production method of the cyclic unsaturated compound of the present invention. That is, it is preferable that the method for producing the cyclic unsaturated compound of the present invention includes a step of reacting the $\alpha,\beta$-unsaturated carboxylic acid with the unsaturated organic compound in the presence of a nitrile solvent or a hydrocarbon solvent.

It is preferable in the production method of the cyclic unsaturated compound of the present invention that the method comprises a step of reacting the $\alpha,\beta$-unsaturated carboxylic acid with the unsaturated organic compound in the presence of a nitrile solvent.

The above-mentioned nitrile solvent may be an organic solvent which can be used as a solvent in the production method of the present invention among nitrile group-containing compounds. Among them, benzonitrile is mentioned as a preferable typical nitrile solvent.

If the reaction is performed in the presence of the above-mentioned nitrile solvent, the cyclic unsaturated compound can be efficiently produced at a smaller amount of the catalyst without using the organic reoxidant agent. Therefore, such a production method is advantageous in terms of reduction in costs and environment.

If the production method of the cyclic unsaturated compound of the present invention includes the step of reacting the $\alpha,\beta$-unsaturated carboxylic acid with the unsaturated organic compound in the presence of a nitrile solvent, only one species may be used or two or more species of nitrile solvents may be appropriately mixed and used in the reaction steps. The kind and the use amount thereof may be appropriately determined depending on the substrate or the catalyst.

The amount of the $\alpha,\beta$-unsaturated carboxylic acid relative to the volume of the above-mentioned nitrile solvent is preferably 0.001 to 1000000 mol/l. The upper limit is more preferably 100000 mol/l, and still more preferably 10000 mol/l. The lower limit is more preferably 0.005 mol/l, and still more preferably 0.01 mol/l.

The amount of the unsaturated organic compound relative to the volume of the above-mentioned nitrile solvent is preferably 0.0001 to 1000000 mol/l. The upper limit is more preferably 500000 mol/l, and still more preferably 100000 mol/l. The lower limit is more preferably 0.0005 mol/l, and still more preferably 0.001 mol/l.

If the reaction is performed in the presence of the above-mentioned nitrile solvent, it is particularly preferable that a compound containing at least one element selected from the group consisting of vanadium, molybdenum, tungsten, and copper coexists as the promoter. More preferable are oxides such as vanadium oxide, molybdenum oxide, tungsten oxide, copper oxide, and a polyoxometalate compound; acetylacetonate compounds such as vanadyl acetylacetonate, and copper acetylacetonate; halogen compounds such as vanadium chloride, molybdenum chloride, tungsten chloride, and copper chloride; carboxylate compounds such as vanadium acetate, copper acetate, copper trifluoroacetate. If the promoter has a ligand, the ligand may be a monodentate ligand or may be a multidentate ligand such as bidentate or higher ligands. If a compound having an chiral ligand is used, α-methylene-γ-butyrolactones having an chirality at the β position and/or γ position may be produced via ligand exchange. The above-mentioned polyoxometalate compound means a polyoxometalate or a polyoxometalate-containing compound, and in the polyoxometalate, a polyatom may be substituted with a different element. A cation is not especially limited, and preferable are proton, alkali metal cation, alkali earth metal cation, zinc ion, lanthanide ion, aluminum ion, indium ion, tin ion, lead ion, iron ion, quarternary ammonium salts (ammonium salt, tetramethylammonium salt, tetraethylammonium salt, tetrapropylammonium salt, tetrabutylammonium (TBA) salt, tributylmethylammonium salt, trioctylmethylammonium salt, trilaurylmethylammonium salt, benzyltrimethylammonium salt, benzyltriethylammonium salt, benzyltributylammonium salt, and cetylpyridinium salt), and quarternary phosphonium salts (tetramethylphosphonium salt, tetraethylphosphonium salt, tetrabutylphosphonium salt, tetraphenylphosphonium salt, ethyltriphenylphosphonium salt, and benzyltriphenylphosphonium salt). Preferable embodiments include TBA-containing [$V_2PMo_{10}O_{40}$], TBA-containing [$V_3SiW_9O_{40}$], TBA-containing [$V_8PMo_4O_{40}$], $NH_4$-containing [$V_2PMo_{10}O_{40}$], and embodiments in which these are supported on carriers such as activated carbon and the like. If these are supported, the element of the Groups 8 to 12 may be supported on the same carrier. The above-mentioned promoter may exist independently in the reaction system or may form a multi-nuclear compound or an alloy with the catalyst. The above-mentioned promoter may be appropriately selected depending on reaction conditions to be employed, and one or two or more species of the promoter may be used. Such a promoter may be added in one portion at the start of the reaction or may be appropriately added during the reaction.

If the production method of the cyclic unsaturated compound of the present invention includes the step of reacting the α,β-unsaturated carboxylic acid with the unsaturated organic compound in the presence of the nitrile solvent, the use amount of the catalyst in the reaction steps is preferably 100 mol % or less relative to 100 mol % of the unsaturated organic compound. The use amount is more preferably 50 mol % or less, and still more preferably 20 mol % or less, and particularly preferably 10 mol % or less. The use amount is preferably 0.0000001 mol % or more. The use amount is more preferably 0.0000005 mol % or more and still more preferably 0.000001 mol % or more, and particularly preferably 0.000005 mol % or more. If the use amount of the catalyst is more than 100 mol %, the yield of the desired substance is no more improved, which may result in economic inefficiency. If the use amount of the catalyst is less than 0.0000001 mol %, the reaction may insufficiently proceed because the amount of the catalyst is small.

If the production method of the cyclic unsaturated compound of the present invention includes the step of reacting the α,β-unsaturated carboxylic acid with the unsaturated organic compound in the presence of the nitrile solvent, the use amount of the organic reoxidant agent in the reaction steps is preferably 100 mol % or less relative to 100 mol % of the α,β-unsaturated carboxylic acid. The use amount is more preferably 50 mol % or less, and still more preferably 10 mol % or less, and particularly preferably substantially 0 mol %. The use amount is preferably 100 mol % or less relative to 100 mol % of the unsaturated organic compound. The use amount is more preferably 50 mol % or less and still more preferably 40 mol % or less, and still more preferably 20 mol % or less, and particularly preferably substantially 0 mol %. If the use amount of the organic reoxidant agent is more than 100 mol % relative to 100 mol % of the α,β-unsaturated carboxylic acid or it is more than 100 mol % relative to 100 mol % of the unsaturated organic compound, the amount of the organic reoxidant agent is not sufficiently reduced, and therefore such a production method may not be advantageous in terms of cost, environment, and the like.

If the production method of the cyclic unsaturated compound of the present invention includes the step of reacting the α,β-unsaturated carboxylic acid with the unsaturated organic compound in the presence of the nitrile solvent, the use amount of the polyoxometalate compound in the reaction steps is preferably 0.00000001 mol % or more and 10000000 mol % or less relative to 100 mol % of the catalyst. The upper limit is more preferably 1000000 mol %, and still more preferably 100000 mol %, and still more preferably 10000 mol %, and particularly preferably 1000 mol %. The lower limit is more preferably 0.0000001 mol %, and still more preferably 0.0000005 mol %, still more preferably 0.000001 mol %, and particularly preferably 0.000005 mol %.

It is preferable in the production method of the cyclic unsaturated compound of the present invention that the method comprises a step of reacting the α,β-unsaturated carboxylic acid with the unsaturated organic compound in the presence of a hydrocarbon solvent. According to this, the cyclic unsaturated compound can be efficiently produced at a smaller amount of the catalyst substantially without using the above-mentioned organic reoxidant agent.

The reason why the cyclic unsaturated compound can be efficiently produced at a smaller amount of the catalyst may be because if the reaction is performed in the presence of a hydrocarbon solvent, the catalyst is easily reoxidized, for example. Therefore the catalytic reaction proceeds efficiently, as mentioned above.

Hexane, cyclohexane, octane, benzene, toluene, xylene, and trimethylbenzene are particularly preferable as the above-mentioned hydrocarbon solvent because it is easily removed by distillation. Only one species may be used or two or more species of hydrocarbon solvents may be appropriately mixed and used. The kind and the use amount thereof may be appropriately determined depending on the substrate or the catalyst.

The amount of the α,β-unsaturated carboxylic acid relative to the volume of the above-mentioned hydrocarbon solvent is preferably 0.0001 to 1000000 mol/l. The upper limit is more preferably 100000 mol/l, and still more preferably 10000 mol/l. The lower limit is more preferably 0.0005 mol/l, and still more preferably 0.001 mol/l.

The amount of the unsaturated organic compound relative to the volume of the above-mentioned hydrocarbon solvent is preferably 0.0001 to 1000000 mol/l. The upper limit is more preferably 500000 mol/l, and still more preferably 100000 mol/l. The lower limit is more preferably 0.0005 mol/l, and still more preferably 0.001 mol/l.

According to the embodiment in which the production method of the present invention includes the step of reacting the α,β-unsaturated carboxylic acid with the unsaturated organic compound in the presence of the hydrocarbon solvent, it is more preferable that the above-mentioned catalyst is a compound containing, as a ligand, a carboxylate, an acetylacetonate, a nitrogen-containing organic compound, a phosphorus-containing organic compound, an unsaturated organic compound, a carbene, a halogen, and the like. If such a compound is used, the production method of the cyclic unsaturated compound of the present invention can be more efficient.

The reason why the cyclic unsaturated compound can be efficiently produced at a smaller amount of the catalyst without using the organic reoxidant agent may be as follows. (1) Due to coordination of the above-mentioned ligand, the oxidation-reduction potential and the electron orbital energy level of the catalyst can be appropriate, and the catalyst is easily reoxidized. (2) The substrate or the reoxidant agent is easily coordinated to the metal, and thereby the main reaction and the reoxidation proceed efficiently. (3) The unsaturated organic compound is easily coordinated to the catalyst, and thereby the reaction with the α,β-unsaturated carboxylic acid proceeds smoothly. (4) A proper coordination site becomes unoccupied and the catalyst has a proper electron density, and thereby an insertion reaction or a β-hydride elimination reaction proceeds smoothly. (5) Aggregation of the catalysts in the reduction state is suppressed. (6) Side reactions such as isomerization reaction, and the like, are suppressed. (7) Ligand exchange may occur among the substrate, the catalyst, and the promoter. Carboxylates, acetylacetonates, and nitrogen-containing organic compounds are more preferable as the above-mentioned ligand, still more preferable are carboxylates and acetylacetonates, and still more preferable are carboxylates and acetylacetonates containing an electron-withdrawing substituent or an electron-donating substituent. If the catalyst has a ligand, the ligand may be a monodentate ligand or may be a multidentate ligand such as bidentate or higher ligands. If a catalyst having a chiral ligand is used, α-methylene-γ-butyrolactones having an chirality at the β position and/or γ position may be produced. The above-mentioned catalyst may exist independently in the reaction system or may form a multi-nuclear compound or an alloy with the promoter or the reoxidant agent. In addition, one or two or more species of the catalysts may be used and may be added in one portion at the start of the reaction or may be successively added during the reaction.

If the production method of the cyclic unsaturated compound of the present invention includes the step of reacting the α,β-unsaturated carboxylic acid with the unsaturated organic compound in the presence of the hydrocarbon solvent, the use amount of the catalyst in the reaction steps is preferably 100 mol % or less relative to the α,β-unsaturated carboxylic acid. The use amount is more preferably 60 mol % or less, and still more preferably 30 mol % or less, and particularly preferably 10 mol % or less. The use amount is preferably 0.00000001 mol % or more. The use amount is more preferably 0.00000005 mol % or more and still more preferably 0.0000001 mol % or more, and particularly preferably 0.0000005 mol % or more.

If the use amount of the catalyst is more than 100 mol %, the yield of the desired substance is no more improved and aggregation of inactive zero-valent catalysts may be deposited, which may result in economic inefficiency. If the use amount of the catalyst is less than 0.00000001 mol %, the reaction may insufficiently proceed because the amount of the catalyst is small.

It is preferable in the production method of the cyclic unsaturated compound of the present invention that the method comprises a step of reacting the α,β-unsaturated carboxylic acid with the unsaturated organic compound in the presence of a promoter.

The above-mentioned promoter means a catalyst that is an assistant component having a function of reinforcing the catalytic performance which the catalyst that is a main component independently shows. The promoter may be an inorganic substance or an organic substance, and may be appropriately selected depending on reaction conditions to be employed. In addition, such a promoter may be added in one portion at the start of the reaction or may be appropriately added during the reaction. Such a promoter may exist independently in the reaction system or may form a multi-nuclear compound or an alloy with the main or other component of catalyst.

The above-mentioned promoter may have a function as a reoxidant agent. With respect to reoxidation, it may be performed during the reaction or a reoxidation treatment may be performed after completion of the reaction. It is preferable that one or more compounds containing a promoter coexist in the reaction system or the catalyst if oxygen is used as one reoxidant agent. At this time, the above-mentioned compound may exist independently in the reaction system or may form a multi-nuclear compound or an alloy with the main or other component of catalyst.

Preferable embodiments of the above-mentioned compound that is a promoter are the same as in the above-mentioned reoxidant agent.

Among the above-mentioned production methods using the promoter, it is particularly preferable that the above-mentioned production method includes a step of reacting the α,β-unsaturated carboxylic acid with the unsaturated organic compound in the presence of the promoter, in the embodiment in which the production method of the present invention includes the step of reacting the α,β-unsaturated carboxylic acid with the unsaturated organic compound in the presence of the hydrocarbon solvent. As a result, the cyclic unsaturated compound can be efficiently produced at a smaller amount of the catalyst using oxygen as one reoxidant agent and substantially without using the organic reoxidant agent. Therefore, such a production method can be advantageous in terms of cost, environment, and the like.

Various publicly known promoters may be used as the above-mentioned promoter, and compounds including at least one element selected from the group consisting of vanadium, molybdenum, tungsten, manganese, iron, cobalt, copper, silver, gold, antimony, bismuth, selenium, and tellurium are particularly preferable as the promoters. Preferable examples of such compounds include oxides such as vanadium oxide, molybdenum oxide, tungsten oxide, manganese dioxide, iron oxide, copper oxide, anitimony oxide, bismuth oxide, selenium dioxide, tellurium dioxide, and polyoxometalate compounds, and compounds containing a carboxylate, an acetylacetonate, a nitrogen-containing organic compound, a phosphorus-containing organic compound, an unsaturated organic compound, a carbene, a halogen and the like, as a ligand. More preferable are compounds containing a carboxylate, an acetylacetonate, a nitrogen-containing organic compound, an unsaturated organic compound, or a halogen as a ligand, and still more preferable are copper compounds containing a carboxylate, an acetylacetonate, a nitrogen-containing organic compound, an unsaturated organic compound, or a halogen as a ligand. The use of such compounds makes it possible to perform the step of reoxidizing the catalyst smoothly and perform the production method of the cyclic unsaturated compound of the present invention more efficiently. Particularly if oxygen is used as one reoxidant agent, such effects extremely highly exhibited. This maybe due to the following reasons. (1) Due to coordination of the above-mentioned ligand, the oxidation-reduction potential or the electron state and the electron orbital energy level of the promoter can be appropriate, and the catalyst is easily reoxidized. (2) The reoxidant agent is easily coordinated to the metal, and thereby the main reaction and the reoxidation proceed efficiently. (3) Aggregation of the catalyst in the reduction state is suppressed. (4) Side reactions such as isomarization reaction are suppressed. (5) Ligand exchange may occur among the substrate, the catalyst, and the promoter. If the promoter has a ligand, the ligand may be a monodentate ligand or may be a multidentate ligand such as bidentate or higher ligands. If a catalyst having an chiral ligand is used, $\alpha$-methylene-$\gamma$-butyrolactones having an chirality at the $\beta$ position and/or $\gamma$ position may be produced. The above-mentioned promoter may exist independently in the reaction system or may form a multi-nuclear compound or an alloy with the catalyst. The above-mentioned reoxidant agent may be appropriately selected depending on reaction conditions to be performed and one or two or more species of the reoxidant agents may be used. In addition, such a reoxidant agent may be added in one portion at the start of the reaction or may be appropriately added during the reaction.

If the production method of the cyclic unsaturated compound of the present invention includes the step of reacting the $\alpha,\beta$-unsaturated carboxylic acid with the unsaturated organic compound in the presence of the hydrocarbon solvent, the use amount of the promoter in the reaction steps is preferably 0.00000001 mol % or more and 10000000 mol % or less relative to 100 mol % of the catalyst. The upper limit is more preferably 1000000 mol %, and still more preferably 100000 mol %, and still more preferably 10000 mol %, and particularly preferably 1000 mol %. The lower limit is more preferably 0.0000001 mol %, and still more preferably 0.0000005 mol %, and still more preferably 0.000001 mol %, and particularly preferably 0.000005 mol %. If the use amount of the promoter is more than 10000000 mol %, the yield of the desired substance is no more improved, which may result in economic inefficiency. If the use amount of the catalyst is less than 0.00000001 mol %, the reaction may insufficiently proceed because the amount of the promoter is small.

The preferable embodiments of the production method of the cyclic unsaturated compound of the present invention include an embodiment in which copper acetate or copper trifluoroacetate is used as the promoter, in addition to palladium trifluoroacetate as the catalyst, for example.

It is preferable that the above-mentioned embodiment in which includes the step of reacting the $\alpha,\beta$-unsaturated carboxylic acid with the unsaturated organic compound in the presence of the basic compound and the embodiment in which the reaction is performed in the presence of the solvent are employed in combination.

It is preferable that the above-mentioned embodiment in which the method includes the step of reacting the $\alpha,\beta$-unsaturated carboxylic acid with the unsaturated organic compound in the presence of the basic compound and the embodiment in which the method includes the step of reoxidizing the catalyst using the reoxidant agent are employed in combination.

It is preferable that the above-mentioned embodiment in which the method includes the step of reacting the $\alpha,\beta$-unsaturated carboxylic acid with the unsaturated organic compound in the presence of the solvent and the embodiment in which the method includes the step of reoxidizing the catalyst using the reoxidant agent are employed in combination.

It is particularly preferable that the above-mentioned embodiment in which the method includes the step of reacting the $\alpha,\beta$-unsaturated carboxylic acid with the unsaturated organic compound in the presence of the basic compound, the embodiment in which the method includes the step of reacting the $\alpha,\beta$-unsaturated carboxylic acid with the unsaturated organic compound in the presence of the solvent and the embodiment in which the method includes the step of reoxidizing the catalyst using the reoxidant agent are employed in combination.

According to the method for producing the cyclic unsaturated compound of the present invention, if "the method includes the step of reacting the $\alpha,\beta$-unsaturated carboxylic acid with the unsaturated organic compound in the presence of the solvent", "the method includes the step of reoxidizing the catalyst using the reoxidant agent" or "the method includes the step of reacting the $\alpha,\beta$-unsaturated carboxylic acid with the unsaturated organic compound in the presence of the basic compound", one or two or more species of the above-mentioned organic oxidizing agents and inorganic oxidizing agents may be used as the reoxidant agent for reoxidizing the catalyst in the reaction steps.

It is preferable in the production method of the present invention that the method comprises a step of inserting an unsaturated bond of the $\alpha,\beta$-unsaturated carboxylic acid into a metal-carbon bond.

The unsaturated organic compound is coordinated to the catalyst such as palladium, and then the $\alpha,\beta$-unsaturated carboxylic acid (ion) attacks the unsaturated bond of the unsaturated organic compound and is bonded thereto. Then, the unsaturated bond derived from the $\alpha,\beta$-unsaturated carboxylic acid inserts into the generated metal (for example, palladium)-carbon bond, and after $\beta$-hydride elimination, a desired cyclic unsaturated compound is obtained.

According to such a production method, the cyclic reaction can proceed efficiently and the yield of the cyclic unsaturated compound can be further improved.

With respect to reaction conditions in the above-mentioned reaction steps according to the method for producing the cyclic unsaturated compound of the present invention, for example, the reaction temperature is preferably 0° or more, and more preferably 20° C. or more. In addition, the reaction temperature is preferably 300° C. or less, and more preferably 200° C. or less. The reaction time is preferably 1 hour or more, and more preferably 4 hours or more. In addition, the reaction time is preferably 96 hours or less, and more preferably 90 hours or less.

The pressure inside a reactor at the early stage of the reaction is preferably a normal pressure or more and a gage pressure of 200 kg/cm$^2$ or less. The upper limit is more preferably 180 kg/cm$^2$, and still more preferably 150 kg/cm$^2$.

If the pressure adjustment or control of the proportion in the gas phase is needed, gas used for such adjustment or control is not especially limited as long as it has no harmful effects on the reaction. Nitrogen, oxygen, air, oxygen/nitrogen standard gas, helium, argon, and the like, are preferable. Only one species may be used or two or more species of the above-mentioned gas may be appropriately mixed and used.

The reaction formula in the above-mentioned production method of the cyclic unsaturated compound is represented by the following formula (1), for example.

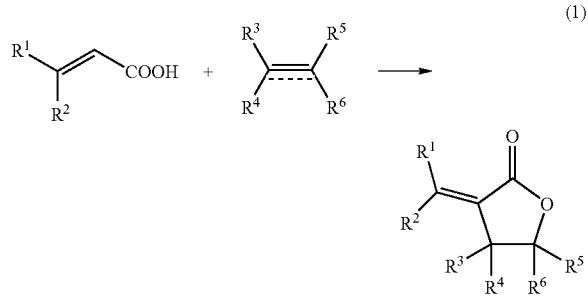

(1)

The above formula (1) is mentioned below.

In the formula, the above-mentioned $R^1$ and $R^2$ are not especially limited, and may be the same or different, and preferably represent a hydrogen atom, an alkyl group containing 1 to 12 carbon atoms, a cycloalkyl group containing 3 to 8 carbon atoms, or an aromatic part-containing group. Still more preferably, the $R^1$ and $R^2$ each represent a hydrogen atom, an alkyl group containing 1 to 8 carbon atoms, a cycloalkyl group containing 4 to 8 carbon atoms, a phenyl group, a nitrophenyl group, a methylphenyl group, a benzyl group, or a naphthyl group. Still more preferably, the $R^1$ and $R^2$ each represent a hydrogen atom, an alkyl group containing 1 to 6 carbon atoms, a cycloalkyl group containing 5 to 7 carbon atoms, a phenyl group, or a naphthyl group. Particularly preferably, the $R^1$ and $R^2$ each represent a hydrogen atom. That is, it is particularly preferable that the α,β-unsaturated carboxylic acid is acrylic acid.

The above-mentioned $R^1$ and $R^2$ may be bonded to each other to form a ring structure.

Preferable examples of the above-mentioned $R^3$, $R^4$, $R^5$, and $R^6$ include: a hydrogen atom; a hydroxyl group; the following organic groups containing 1 to 60 carbon atoms such as linear saturated alkyl groups, branched saturated alkyl groups, alicyclic saturated alkyl groups, aromatic part-containing groups, linear unsaturated alkyl groups, branched unsaturated alkyl groups, and alicyclic unsaturated alkyl groups; the following atomic groups containing 0 to 60 carbon atoms having the group such as ester group, nitrile group, carboxylic acid group, ether group, a hydroxyl group, a halogen group, an isonitrile group, a cyanate group, an isocyanate group, a thiocyanate group, an isothiocyanate group, a sulfide group, a disulfide group, a sulfoxide group, a sulfone group, a nitro group, a nitroso group, a sulfonic acid group, a carbonyl group (for example, ketone or aldehyde), an amino group, an amine oxide group, a nitrone group, an amide group, an azido group, an acetal group, an azo group, an azoxy group, an azine group, an imino group, an imide group, an enamine group, an enamide group, an ortho ester group, a diazo group, a diazonium group, a ketal group, an onium salt, a heterocyclic compound, a hetero aromatic compound, or a hetero element. More preferable examples thereof include: a hydrogen atom; a hydroxyl group; the following organic groups containing 1 to 30 carbon atoms such as linear saturated alkyl groups, branched saturated alkyl groups, alicyclic saturated alkyl groups, aromatic part-containing groups, linear unsaturated alkyl groups, branched unsaturated alkyl groups, and alicyclic unsaturated alkyl groups; the following atomic groups containing 0 to 30 carbon atoms having the group such as ester group, nitrile group, carboxylic acid group, ether group, a hydroxyl group, a sulfonic acid group, a carbonyl group, an amino group, an amide group, or an onium salt. Still more preferable examples thereof include: a hydrogen atom; a hydroxyl group; the following organic groups containing 1 to 18 carbon atoms such as linear saturated alkyl groups, branched saturated alkyl groups, and alicyclic saturated alkyl groups; and the following atomic groups containing 0 to 18 carbon atoms having the group such as ester group, carboxylic acid group, ether group, a hydroxyl group, a sulfonic acid group, a carbonyl group, or an amino group. The above-mentioned $R^3$, $R^4$, $R^5$, and $R^6$ may be bonded to one another to form a ring structure.

The α,β-unsaturated carboxylic acid used in the production method of the present invention is not especially limited, but α,β-unsaturated carboxylic acids represented by the following formula (2) is preferable.

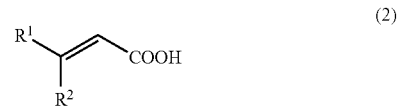

(2)

In the above formula (2), $R^1$ and $R^2$ are the same as those in the above formula (1).

Among the above-mentioned α,β-unsaturated carboxylic acids, acrylic acid is particularly preferable.

The unsaturated organic compound used in the production method of the present invention, that is, a double bond-containing compound or a triple bond-containing compound is not especially limited, but unsaturated organic compounds represented by the following formula (3) are preferable.

(3)

In the above formula (3), $R^3$, $R^4$, $R^5$, and $R^6$ are the same as those in the above formula (1).

It is preferable that the unsaturated organic compound is a double bond-containing compound having 2 to 20 carbon atoms.

Examples of the above-mentioned unsaturated organic compound include ethylene, fluorine-containing ethylene, propylene, fluorine-containing propylene, 1-butene, 2-butene, isobutene, butadiene, isoprene, 1-pentene, 2-pentene, cyclopentene, cyclopentadiene, 1-hexene, 2-hexene, 3-hexene, cyclohexene, 1-heptene, 1-octene, 1-decene, dicyclopentadiene, norbornene, vinyl acetate, ethyl vinyl ether, butyl vinyl ether, styrene, methyl styrene, and (meth)acrylates such as methyl(meth)acrylate, ethyl(meth)acrylate, butyl(meth)acrylate, 2-ethylhexyl(meth)acrylate, and 2-hydroxyethyl(meth)acrylate.

It is particularly preferable that the above-mentioned unsaturated organic compound contains 12 or less carbon atoms. In this case, according to the production method of the present invention, the yield of the cyclic unsaturated compound and the selectivity of the cyclic unsaturated compound to the acyclic unsaturated compound can be significantly improved, and thereby the productivity and the economical efficiency are dramatically improved. Particularly if the cyclic unsaturated compound is produced using the unsaturated organic compound containing 12 or less carbon atoms as a starting material, a reaction which produces the cyclic unsaturated compound is hard to proceed in some cases, but according to the present invention, this reaction sufficiently proceeds. The unsaturated organic compound more preferably contains 10 or less carbon atoms and still more preferably 8 or less carbon atoms. Among them, ethylene, propylene, 1-butene, isobutene, butadiene, cyclohexene, 1-octene, 1-decene, norbornene, vinylacetate, ethyl vinyl ether, butyl vinyl ether, styrene, methyl styrene, and (meth)acrylates are particularly preferable and still more preferable is at least one selected from the group consisting of ethylene, propylene, 1-butene, isobutene, butadiene, cyclohexene, 1-octene, 1-decene, norbornene, vinyl acetate, ethyl vinyl ether, butyl vinyl ether, styrene, and methyl styrene because advantageous effects of the present invention are remarkably exhibited. In order to increase the selectivity of the desired substance, propylene, 1-butene, butadiene, 1-octene, norbornene, vinyl acetate, butyl vinyl ether, and styrene are still more preferable. For example, if these compounds are used, the selectivity can be increased even in the system where the selectivity of the desired cyclic unsaturated compound is hard to improve when ethylene is used, for example.

The above-mentioned α,β-unsaturated carboxylic acid in the reaction steps is preferably 0.00001 mol % or more and 1000000 mol % or less relative to 100 mol % of the unsaturated organic compound. If the α,β-unsaturated carboxylic acid is less than 0.00001 mol % or more than 1000000 mol %, sufficient yield or selectivity may not be obtained. The above-mentioned lower limit is more preferably 0.0001 mol %, and still more preferably 0.001 mol %. The lower limit is still more preferably 0.01 mol %, and still more preferably 0.1 mol %, and particularly preferably 1 mol %. The above-mentioned upper limit is more preferably 500000 mol %, and still more preferably 250000 mol %, and still more preferably 100000 mol %, and still more preferably 50000 mol %, and particularly preferably 25000 mol %. With the above-mentioned α,β-unsaturated carboxylic acid and unsaturated organic compound, one or two or more species of them may be used, and they may be added in one portion at the start of the reaction or may be successively added during the reaction.

According to the production method of the present invention, a value (A/B) of a yield of a cyclic unsaturated compound (A) to a yield of a acyclic unsaturated compound (B), that is, a selectivity of a desired cyclic unsaturated compound (for example, methylene lactone) to a acyclic unsaturated compound (for example, vinyl acrylate) is preferably 0.05 or more, and more preferably 0.1 or more, and still more preferably 0.2 or more, and particularly preferably 0.4 or more. Such an embodiment in which the selectivity has such a value is preferable for the production method of the cyclic unsaturated compound of the present invention.

The cyclic unsaturated compound which can be produced by the production method of the present invention is not especially limited. Cyclic unsaturated compounds represented by the following formula (4) are mentioned as typical examples of the cyclic unsaturated compound preferably produced by the above-mentioned production method.

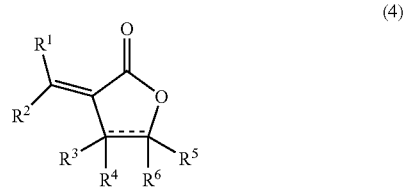

(4)

The above formula (4) is mentioned below. In the formula, $R^1$, $R^2$, $R^3$, $R^4$, $R^5$, and $R^6$ are the same as those in the above formula (1). Typical cyclic unsaturated compounds represented by the above formula (4) which can be more preferably produced by the above-mentioned production method include α-methylene-γ-butyrolactone produced from acrylic acid and ethylene, represented by the following formula (5);

(5)

a compound produced from acrylic acid and propylene, represented by the following formula (6);

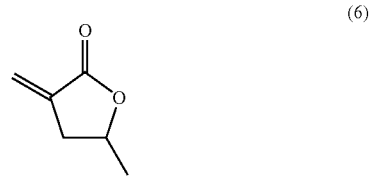

(6)

a compound produced from acrylic acid and isobutene, represented by the following formula (7);

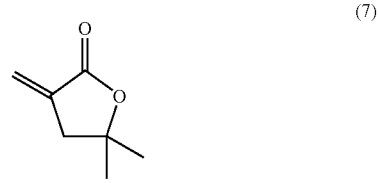

(7)

a compound produced from acrylic acid and 1-butene, represented by the following formula (8);

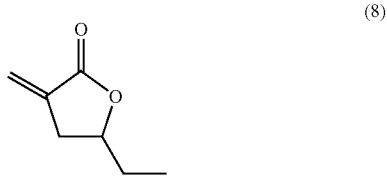

(8)

a compound produced from acrylic acid and 1-octene, represented by the following formula (9);

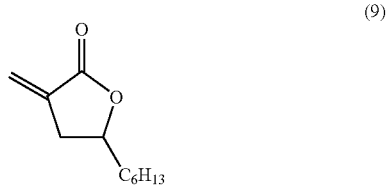

(9)

a compound produced from acrylic acid and cyclohexene, represented by the following formula (10);

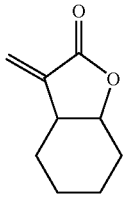
(10)

a compound produced from acrylic acid and norbornene, represented by the following formula (11);

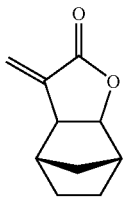
(11)

and a compound produced from acrylic acid and vinyl acetate, represented by the following formula (12).

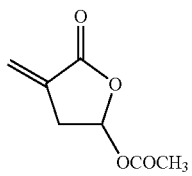
(12)

The above formulae (6) to (12) show compounds containing a substituent at the γ position, but the cyclic unsaturated compounds may be compounds containing the same substituent at the β position.

It is preferable that the cyclic unsaturated compound is a compound containing a double bond, and the double bond exists at an exo position and/or an endo position.

The exo position means a position outside the ring, and the endo position means a position inside the ring.

If acrylic acid is reacted with ethylene by the production method of the present invention, α-methylene-γ-butyrolactone represented by the above formula (5) is mentioned as a cyclic unsaturated compound containing a double bond at the exo position, that is, an exo-cyclic unsaturated compound, and compounds represented by the following formula (13) or (14) are mentioned as an unsaturated compound containing a double bond at the endo-position, that is, an endo-cyclic unsaturated compound.

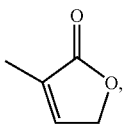
(13)

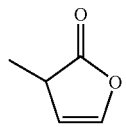
(14)

According to the production method of the present invention, in addition to the five-membered cyclic unsaturated compound which contains a double bond at the exo position and/or the endo position, six-membered cyclic unsaturated compounds represented by the following formula (15):

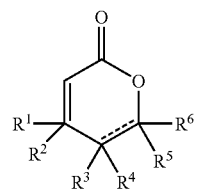
(15)

(in the formula, $R^1$, $R^2$, $R^3$, $R^4$, $R^5$, and $R^6$ are the same as those in the above formula (1)) are generated. For example, the case where palladium is used as the catalyst is mentioned. When carbopalladation of the α,β-unsaturated compound proceeds, a five-membered ring is generated if carbopalladation (insertion reaction) where carbon binds to the α position carbon and palladium binds to β position carbon proceeds, and a six-membered ring is generated if carbopalladation (insertion reaction) where palladium binds to the a position carbon and carbon binds to β position carbon proceeds.

According to the production method of the cyclic unsaturated compound of the present invention, it is preferable that the α,β-unsaturated carboxylic acid includes at least one hydrogen atom at carbon at a γ position. If the above-mentioned α,β-unsaturated carboxylic acid includes at least one hydrogen atom at carbon at the γ position, the cyclic unsaturated compound obtained by the production method of the present invention includes a cyclic unsaturated compound whose double bond exists in the side chain of the ring structure. In this case, it is preferable that the cyclic unsaturated compound is the above-mentioned double bond-containing compound and the double bond exists in the side chain of the cyclic structure as an alkene group. The "double bond exists in the side chain of the ring structure as an alkene group" means, for example, cyclic unsaturated compounds in which not a methylene group but a vinyl group is directly bonded to the ring and means compounds represented by the following formula (19), which are mentioned below. That is, according to the production method of the cyclic unsaturated compound of the present invention, it is preferable that the cyclic unsaturated compound is a compound containing a double bond, and the double bond exists in a side chain of a ring structure. It is more preferable that the double bond is a double bond of a vinyl group.

The reaction formula in the above-mentioned production method of the cyclic unsaturated compound of the present invention is represented by the following formula (16), for example. Not only the reaction represented by the above formula (1) but also a reaction represented by the following formula (16) selectively occurred.

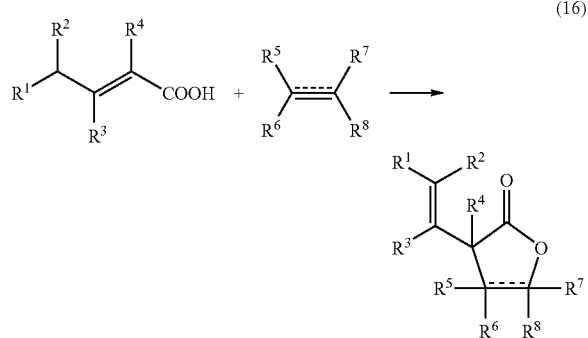

(16)

The above-mentioned formula (16) is mentioned below.

In the formula, it is more preferable that the above-mentioned $R^1$, $R^2$, $R^3$, and $R^4$ are not especially limited, and may be the same or different, and each represent a hydrogen atom, an alkyl group containing 1 to 12 carbon atoms, a cycloalkyl group containing 3 to 8 carbon atoms, or an aromatic part-containing group. Still more preferably, the $R^1$, $R^2$, $R^3$, and $R^4$ each represent a hydrogen atom, an alkyl group containing 1 to 8 carbon atoms, a cycloalkyl group containing 4 to 8 carbon atoms, a phenyl group, a nitrophenyl group, a methylphenyl group, a benzyl group, or a naphthyl group. Still more preferably, the $R^1$, $R^2$, $R^3$, and $R^4$ each represent a hydrogen atom, an alkyl group containing 1 to 6 carbon atoms, a cycloalkyl group containing 5 to 7 carbon atoms, a phenyl group, or a naphthyl group. Particularly preferably, the $R^1$, $R^2$, $R^3$, and $R^4$ each represent a hydrogen atom. The above-mentioned $R^1$ and $R^2$ may be bonded to each other to form a ring structure.

Preferable examples of the above-mentioned $R^5$, $R^6$, $R^7$, and $R^8$ include: a hydrogen atom; a hydroxyl group; the following organic groups containing 1 to 60 carbon atoms such as linear saturated alkyl groups, branched saturated alkyl groups, alicyclic saturated alkyl groups, aromatic part-containing groups, linear unsaturated alkyl groups, branched unsaturated alkyl groups, and alicyclic unsaturated alkyl groups; the following atomic groups containing 0 to 60 carbon atoms having the group such as ester group, nitrile group, carboxylic acid group, ether group, a hydroxyl group, a halogen group, an isonitrile group, a cyanate group, an isocyanate group, a thiocyanate group, an isothiocyanate group, a sulfide group, a disulfide group, a sulfoxide group, a sulfone group, a nitro group, a nitroso group, a sulfonic acid group, a carbonyl group (for example, ketone or aldehyde), an amino group, an amine oxide group, a nitrone group, an amide group, an azido group, an acetal group, an azo group, an azoxy group, an azine group, an imino group, an imide group, an enamine group, an enamide group, an ortho ester group, a diazo group, a diazonium group, a ketal group, an onium salt, a heterocyclic compound, a hetero aromatic compound, or a hetero element. More preferable examples thereof include: a hydrogen atom; a hydroxyl group; the following organic groups containing 1 to 30 carbon atoms such as linear saturated alkyl groups, branched saturated alkyl groups, alicyclic saturated alkyl groups, aromatic part-containing groups, linear unsaturated alkyl groups, branched unsaturated alkyl groups, and alicyclic unsaturated alkyl groups; the following atomic groups containing 0 to 30 carbon atoms having the group such as ester group, nitrile group, carboxylic acid group, ether group, a hydroxyl group, a sulfonic acid group, a carbonyl group, an amino group, an amide group, or an onium salt. Still more preferable examples thereof include: a hydrogen atom; a hydroxyl group; the following organic groups containing 1 to 18 carbon atoms such as linear saturated alkyl groups, branched saturated alkyl groups, alicyclic saturated alkyl groups, and aromatic part-containing groups; and the following atomic groups containing 0 to 18 carbon atoms having the group such as ester group, carboxylic acid group, ether group, a hydroxyl group, a sulfonic acid group, a carbonyl group, or an amino group. The above-mentioned $R^5$, $R^6$, $R^7$, and $R^8$ may be bonded to one another to form a ring structure.

According to the production method of the cyclic unsaturated compound of the present invention, it is more preferable that the above-mentioned α,β-unsaturated carboxylic acid is represented by the following formula (17).

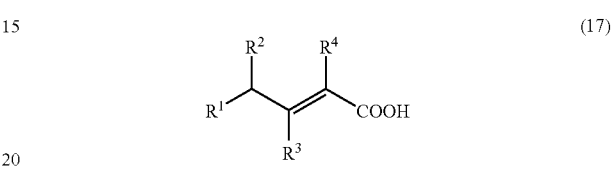

(17)

In the above formula (17), $R^1$, $R^2$, $R^3$, and $R^4$ are the same as those in the above formula (16).

Particularly preferably, the above-mentioned α,β-unsaturated carboxylic acid is crotonic acid, isocrotonic acid, or β,β-dimethylacrylic acid.

The above-mentioned preferable embodiments and the embodiment in which the α,β-unsaturated carboxylic acid is crotonic acid may be appropriately employed in combination. That is, it is preferable that the production method of the present invention has an embodiment in which the α,β-unsaturated carboxylic acid is crotonic acid.

The unsaturated organic compound used in the production method of the present invention, that is, the double bond-containing compound or the triple bond-containing compound is not especially limited, but compounds represented by the following formula (18) are preferable.

(18)

In the above formula (18), $R^5$, $R^6$, $R^7$, and $R^8$ are the same as those in the above formula (16). It is preferable that the above-mentioned unsaturated organic compound is a double bond-containing compound having 2 to 20 carbon atoms. Examples of the above-mentioned unsaturated organic compound include ethylene, fluorine-containing ethylene, propylene, fluorine-containing propylene, 1-butene, 2-butene, isobutene, butadiene, isoprene, 1-pentene, 2-pentene, cyclopentene, cyclopentadiene, 1-hexene, 2-hexene, 3-hexene, cyclohexene, 1-heptene, 1-octene, 1-decene, dicyclopentadiene, norbornene, vinyl acetate, ethyl vinyl ether, butyl vinyl ether, styrene, methyl styrene, and (meth)acrylates such as methyl(meth)acrylate, ethyl(meth)acrylate, butyl(meth)acrylate, 2-ethylhexyl(meth)acrylate, and 2-hydroxyethyl(meth)acrylate.

It is particularly preferable that the above-mentioned unsaturated organic compound contains 12 or less carbon atoms. In this case, according to the production method of the present invention, the yield of the cyclic unsaturated compound and the selectivity of the cyclic unsaturated compound to the acyclic unsaturated compound can be significantly improved, and thereby the productivity and the economical efficiency are dramatically improved. The unsaturated organic compound more preferably contains 10 or less carbon atoms and still more preferably contains 8 or less carbon atoms. Among them, ethylene, propylene, 1-butene, isobutene, butadiene, cyclohexene, 1-octene, 1-decene, norbornene, vinyl acetate, ethyl vinyl ether, butyl vinyl ether, styrene, methyl styrene, and (meth)acrylates are particularly preferable, and at least one selected from the group consisting of ethylene, propylene, 1-butene, isobutene, butadiene, cyclohexene, 1-octene, 1-decene, norbornene, vinyl acetate, ethyl vinyl ether, butyl vinyl ether, styrene, and methyl styrene is still more preferable, because advantageous effects of the present invention are significantly exhibited. In order to increase the selectivity of the desired cyclic unsaturated compound, propylene, 1-butene, butadiene, 1-octene, norbornene, vinyl acetate, butyl vinyl ether, and styrene are still more preferable. If these compounds are used, the selectivity can be increased even in the system where the selectivity is hard to improve if ethylene is used, for example.

The above-mentioned α,β-unsaturated carboxylic acid in the reaction steps is preferably 0.00001 mol % or more and 1000000 mol % or less relative to 100 mol % of the unsaturated organic compound. If the α,β-unsaturated carboxylic acid is less than 0.00001 mol % or more than 1000000 mol %, sufficient yield or selectivity may not be obtained. The above-mentioned lower limit is more preferably 0.0001 mol %, and still more preferably 0.001 mol %. The lower limit is still-more preferably 0.01 mol %, and still more preferably 0.1 mol %, and particularly preferably 1 mol %. The above-mentioned upper limit is more preferably 500000 mol %, and still more preferably 250000 mol %, and still more preferably 100000 mol %, and still more preferably 50000 mol %, and particularly preferably 25000 mol %. With the above-mentioned α,β-unsaturated carboxylic acid and unsaturated organic compound, one or two or more species of them may be used, and they may be added in one portion at the start of the reaction or may be successively added during the reaction.

According to the production method of the present invention, a value (A/B) of a yield of a cyclic unsaturated compound (A) to a yield of a acyclic unsaturated compound (B), that is, a selectivity of a desired cyclic unsaturated compound (for example, vinyl lactone) to a acyclic unsaturated compound (for example, vinyl crotonate) is preferably 0.05 or more, and more preferably 0.1 or more, and still more preferably 0.2 or more, and particularly preferably 0.4 or more. Such an embodiment in which the selectivity has such a value is preferable for the production method of the cyclic unsaturated compound of the present invention.

The cyclic unsaturated compound which can be produced by the production method of the present invention is not especially limited. Compounds represented by the following formula (19) are mentioned as typical examples of the cyclic unsaturated compound preferably produced by the above-mentioned production method.

(19)

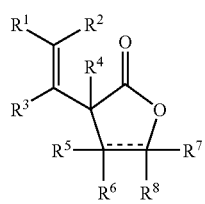

The above-mentioned formula (19) is mentioned below. In the formula, $R^1$, $R^2$, $R^3$, $R^4$, $R^5$, $R^6$, $R^7$, and $R^8$ are the same as those in the above formula (16). Typical cyclic unsaturated compounds represented by the above formula (19) which can be more preferably produced by the above-mentioned production method include α-vinyl-γ-butyrolactone produced from crotonic acid and ethylene, represented by the following formula (20):

(20)

a compound produced from crotonic acid and propylene, represented by the following formula (21);

(21)

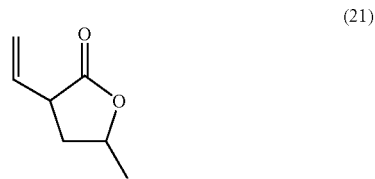

a compound produced from crotonic acid and isobutene, represented by the following formula (22);

(22)

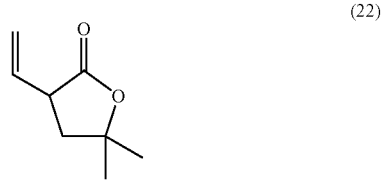

a compound produced from crotonic acid and 1-butene, represented by the following formula (23);

(23)

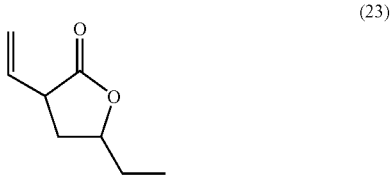

a compound produced from crotonic acid and 1-octene, represented by the following formula (24);

(24)

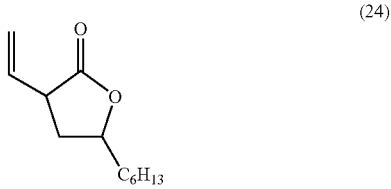

a compound produced from crotonic acid and norbornene, represented by the following formula (25);

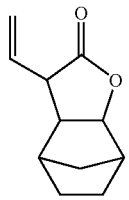

(25)

and a compound produced from crotonic acid and styrene, represented by the following formula (26).

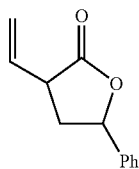

(26)

The above formulae (21) to (26) show compounds containing a substituent at the γ position, but maybe compounds containing the same substituent at the β position.

It is preferable that the cyclic unsaturated compound is a compound containing a double bond, and the double bond exists as an alkene group in a side chain of a ring structure. More preferably, the cyclic unsaturated compound contains a vinyl group at the a position of the ring structure. The vinyl group means a $CH_2=CH$-structure group.

The case where palladium is used as the catalyst in the production method of the present invention is mentioned, for example. When carbopalladation of the α,β-unsaturated carboxylic acid proceeds, a five-membered ring is generated if carbopalladation (insertion reaction) where carbon binds to the α position carbon and palladium binds to β position carbon proceeds, and a six-membered ring is generated as a byproduct if carbopalladation (insertion reaction) where palladium binds to the α position carbon and carbon binds to β position carbon proceeds. In addition, after the carbopalladation (insertion reaction) where carbon binds to the α position carbon and palladium binds to β position carbon proceeds, a five-membered methylene lactone containing an alkene group bonded to the ring structure maybe generated if $R^4$ is hydrogen, a carboxylate group, an alkoxyl group, and the like.

According to the production method of the present invention, an additive may be added to the reaction mixture in order to further accelerate the reaction, improve and stabilize the catalyst activity. The additive is not especially limited as long as it has no harmful effects on the reaction, but preferable examples thereof include Broensted acid, Lewis acid, and compounds containing an element of the Groups 15 to 17, organic compounds containing unsaturated bond, and salts. More preferably, examples of the Broensted acid include mineral acids, carboxylic acids, sulfonic acids, amino acids, compounds containing a hydroxyl group bonded to an aromatic ring, inorganic solid substances typified by zeolite, clay compound, and the like, and ion-exchange resin; examples of the Lewis acid include compounds containing an element of the Groups 3 to 14, metal-substituted inorganic solid substances, and metal-substituted clay compounds; examples of the compounds containing an element of the Groups 15 to 17 include pyridine, lutidine, triethylamine, tributylamine, sparteine, 2,2'-bipyridyl, 1,10-phenanthroline, 2,9-dimethyl-1,10-phenanthroline, 2,9-dimethyl-4,7-diphenyl-1,10-phenanthroline, nitrogen-containing carbene such as 1,3-diisopropyl imidazole-2-ylidene and 1,3-bis(2,6-diisopropylphenyl)imidazole-2-ylidene, triarylphosphine, and trialkylphosphine; examples of the organic compounds containing unsaturated bond include (meth)acrylic acids, electron-withdrawing group-containing alkene, benzoquinone, and cyclooctadiene; examples of the salts include lithium chloride, sodium chloride, potassium chloride, cesium chloride, magnesium chloride, calcium chloride, barium chloride, lithium bromide, sodium bromide, potassium bromide, cesium bromide, magnesium bromide, calcium bromide, barium bromide, lithium iodide, sodium iodide, potassium iodide, cesium iodide, magnesium iodide, calcium iodide, barium iodide, tetramethylammonium chloride, tetraethylammonium chloride, tetrapropylammonium chloride, tetrabutylammonium chloride, tetrahexylammonium chloride, tetraoctylammonium chloride, cetyltrimethylammonium chloride, pyridinium chloride, tetramethylammonium bromide, tetraethylammonium bromide, tetrapropylammonium bromide, tetrabutylammonium, bromide, tetrahexylammonium bromide, tetraoctylammonium bromide, cetyltrimethylammonium bromide, pyridinium bromide, tetramethylammonium iodide, tetraethylammonium iodide, tetrapropylammonium iodide, tetrabutylammonium iodide, tetrahexylammonium iodide, tetraoctylammonium iodide, cetyltrimethylammonium iodide, pyridinium iodide, a surfactant, an inorganic solid substance typified by zeolite, clay compound, and the like, alkali metal and/or alkali earth metal-containing neutral salts such as ion-exchange resin, and salts having a function of surface activity. Further, a small amount of the above-mentioned basic compound or solvent may be added to the system, as an additive or a ligand.

The above-mentioned additive may be previously coordinated and/or supported on the catalyst to be coexistent. Among the above-mentioned compounds, carboxylic acids, sulfonic acids, and organic compounds containing unsaturated bond are preferable. More preferably, examples of the above-mentioned carboxylic acids or sulfonic acids include electron-withdrawing group-containing carboxylic acids such as trifluoroacetic acid, trichloroacetic acid, benzoic acid, and pentafluoro benzoic acid, methansulfonic acid, trifluoromethansulfonic acid, and p-toluenesulfonic acid. More preferable examples of the above-mentioned organic compound containing unsaturated bond include (meth)acrylates such as metyl(meth)acrylate and ethyl(meth)acrylate, α-methylene-γ-butyrolactones, α-vinyl-γ-butyrolactones, and cyclic alkenes such as cyclooctadiene and benzoquinone. The above-mentioned carboxylic acids, sulfonic acids, organic compounds containing unsaturated bond contribute to stabilization of the catalyst, suppression of the catalyst aggregation, acceleration of the reoxidation, improvement in reactivity, and the like, because of coordination to the catalyst, and the like. The organic compound containing unsaturated bond can be expected to exhibit effects such as stabilization of the catalyst or improvement in the reactivity, as mentioned above, in addition to the functions as a substrate, a reoxidant agent, a product, and the like.

According to the production method of the present invention, the α,β-unsaturated carboxylic acid and the desired cyclic unsaturated compound easily polymerized with each other in some cases, and therefore it is preferable that a polymerization inhibitor is added to the reaction system to prevent the polymerization during the reaction.

The above-mentioned polymerization inhibitor is not especially limited, as long as it has a function as a polymerization inhibitor. Examples thereof include molecular oxygen, molecular oxygen-containing gas, air, and gas with unpaired electrons such as nitrogen monoxide; quinones, such as hydroquinone, methyl hydroquinone, methoxyphenol, t-butylhydroquinone, 2,4-di-t-butylhydroquinone, 2,4-dimethyl hydroquinone; amine compounds, such as phenothiazine; phenols, such as 2,4-dimethyl-6-t-butyl phenol, 2,4-di-t-butyl phenol, p-methoxyphenol; substituted catechols, such as a p-t-butyl catechol; substituted resorcins; stable free radical-containing compounds such as tetramethylpiperidine-N-oxide, and 4-hydroxy-tetramethyl piperidine-N-oxide; and metal-containing compounds such as copper dithiocarbamate. One or two or more species of them may be preferably used.

After completion of the reaction, if needed, separation and purification are performed through steps such as distillation, filtration, extraction, centrifugal separation, recrystallization, dryness, and column chromatography, and thereby a desired cyclic unsaturated compound can be obtained. According to such separation and purification steps, for example, the reaction mixture after the reaction, the reaction mixture from which the catalyst is separated, the extract after subjected to specific operations, such as extraction, are distilled (rectified) under normal pressure or reduced pressure. As a result, the cyclic unsaturated compound that is a product can be isolated and purified, and simultaneously unreacted $\alpha,\beta$-unsaturated carboxylic acid, unsaturated organic compound, or solvent can be separated and recovered. Such residual $\alpha,\beta$-unsaturated carboxylic acid, unsaturated organic compounds, and solvent can be used for the reaction again because they have high purity. Any of the above-mentioned polymerization inhibitors may be used as a polymerization inhibitor used for the distillation. Among them, more preferable are amine compounds such as phenothiazine; stable free radical-containing compounds such as tetramethylpiperidine-N-oxide, and 4-hydroxy-tetramethylpiperidine-N-oxide; and metal-containing compounds such as copper dithiocarbamate. One or two or more species of them may be used.

The present invention is a catalyst for producing a cyclic unsaturated compound by reacting an $\alpha,\beta$-unsaturated carboxylic acid with an unsaturated organic compound, wherein the catalyst essentially contains a multi-nuclear compound.

If the catalyst for producing the cyclic unsaturated compound according to the present invention is used, cyclic unsaturated compounds can be produced with sufficient high yield while generation of acyclic unsaturated compounds can be sufficiently suppressed.

The catalyst for producing the cyclic unsaturated compound according to the present invention can be preferably used for the method for producing the cyclic unsaturated compound of the present invention, and the above-mentioned embodiments of the catalyst in the production method of the present invention can be preferably applied to the catalyst. For example, it is preferable that the catalyst for producing the cyclic unsaturated compound of the present invention is supported on a carrier, and the catalyst comprises a compound including at least one element selected from the group consisting of elements of the Groups 8 to 12 and an element other than the elements of the Groups 8 to 12.

It is more preferable that the above-mentioned element other than the elements of the Groups 8 to 12 is at least one element selected from the group consisting of alkali metal elements, alkali earth metal elements, and elements of the Groups 13 to 17.

If such a catalyst is used as the catalyst for producing the cyclic unsaturated compound of the present invention, the yield of the desired cyclic unsaturated compound can be increased and generation of acyclic unsaturated compounds is further sufficiently suppressed.

The present invention is also an $\alpha$-methylene-$\gamma$-butyrolactone composition including a cyclic unsaturated compound containing a double bond at an endo position. The cyclic unsaturated compound containing a double bond at the endo position is considered to be generated as follows. For example, an $\alpha$-methylene-$\gamma$-butyrolactone is generated by $\beta$-hydride elimination and then the generated $\alpha$-methylene-$\gamma$-butyrolactone is inserted again into a palladium-hydride species, and the following $\beta$-hydride elimination causes isomerization. It is preferable that the above-mentioned cyclic unsaturated compound containing a double bond at the endo position is 0.00001 to 1000 mol % in 100 mol % of the $\alpha$-methylene-$\gamma$-butyrolactone that is the unsaturated compound containing a double bond at the exo position. The content is more preferably 0.0001 to 500 mol %, and still more preferably 0.001 to 100 mol %, and still more preferably 0.01 to 50 mol %. If the above-mentioned $\alpha$-methylene-$\gamma$-butyrolactone composition containing the cyclic unsaturated compound containing a double bond at the endo position is used as a monomer, a polymer excellent in heat resistance and optical characteristics can be formed.

The present invention is also an $\alpha$-methylene-$\gamma$-butyrolactone composition including a six-membered unsaturated compound, which may be produced through the above-mentioned reaction mechanism. The six-membered unsaturated compound means an unsaturated compound containing a six-membered ring, and is also referred to as six-membered cyclic unsaturated compound.

It is preferable that the content of the above-mentioned six-membered unsaturated compound is 0.00001 to 1000 mol % in 100 mol % of $\alpha$-methylene-$\gamma$-butyrolactone that is an unsaturated compound containing a double bond at the exo position. The content is more preferably 0.0001 to 500 mol %, and still more preferably 0.001 to 100 mol %, and still more preferably 0.01 to 50 mol %. If the above-mentioned $\alpha$-methylene-$\gamma$-butyrolactone composition containing a six-membered unsaturated compound is used as a monomer, a polymer excellent in heat resistance and optical characteristics can be formed.

The above-mentioned $\alpha$-methylene-$\gamma$-butyrolactone composition containing a six-membered unsaturated compound can be preferably produced by the above-mentioned production method of the present invention.

Effect of the Invention

The method for producing the cyclic unsaturated compound of the present invention has the above-mentioned configuration and the method is a useful production method which can be applied to industrial production because the method can reduce generation of acyclic unsaturated compounds in reaction steps and improve a reaction rate and a yield of the cyclic unsaturated compound.

Best Modes for Carrying out the Invention

The present invention is mentioned below in more detail with reference to Embodiments, but the present invention is not limited to only these Embodiments.

Example 1

Into a 10 mL autoclave, acrylic acid (0.43 g, 6.0 mmol) as the $\alpha,\beta$-unsaturated carboxylic acid, benzoquinone (0.22 g, 2.0 mmol), sodium acrylate (2.7 mg, 0.03 mmol) as the basic compound, palladium acetate (11.2 mg, 5 mol %) as the compound including at least one element selected from the group consisting of elements of the Groups 8 to 12, ethylene gas (28 mg, 1.0 mmol) as the unsaturated organic compound, and N-methylpyrrolidone (NMP) (3 mL) as the solvent were added. The gas phase was composed of 0.5 kg/cm$^2$ of nitrogen gas and 3.5 kg/cm$^2$ of oxygen gas and the mixture was stirred at 50° C. for 16 hours. After cooling, the reaction mixture was analyzed by gas chromatography. The desired product was obtained in a 25% yield. FIG. 1 schematically shows a possible reaction mechanism in Example 1.

Also in Examples 2 to 18, the reaction was performed by the same production method as in Example 1 except that the proportion and the reaction conditions shown in Table 1 were changed, and the reaction mechanisms were the same as in FIG. 1. Table 1 shows these results.

Example 19

A catalyst was prepared by flowing 2.75% oxygen/nitrogen standard gas (flow rate: 500 mL/min) into an egg shell type 5% Pd/activated carbon (5 g) (product of Johnson Matthey), at 400° C. for 8 hours. Into a 10 mL autoclave, acrylic acid (3.0 g, 42 mmol) as the α,β-unsaturated carboxylic acid, the above-mentioned catalyst (0.2g, 10 mol %) as at least one element selected from the group consisting of elements of the Groups 8 to 12, and p-methoxyphenol (3 mg) were added. Then, 0.5 kg/cm$^2$ of nitrogen gas, 3.5 kg/cm$^2$ of oxygen gas, and ethylene gas (28 mg, 1.0 mmol) as the unsaturated organic compound were added into the gas phase. The mixture was stirred at 80° C. for 16 hours. After cooling, the gas phase was purged and the reaction mixture was analyzed by gas chromatography. The yield of α-methylene-γ-butyrolactone was 15% and that of vinyl acrylate was 18%.

Example 20

A catalyst was prepared by flowing 2.75% oxygen/nitrogen standard gas (flow rate: 500 mL/min) into an egg shell type 5% Pd/activated carbon (5 g) (product of Johnson Matthey), at 300° C. for 8 hours. Into a 10 mL autoclave, acrylic acid (3.0 g, 42 mmol) as the above-mentioned α,β-unsaturated carboxylic acid and the above-mentioned catalyst (0.2g, 10mol %) as the at least one element selected from the group consisting of elements of the Groups 8 to 12, and p-methoxyphenol (3 mg) were added. Then, 0.5 kg/cm$^2$ of nitrogen gas, 3.5 kg/cm$^2$ of oxygen gas, and ethylene gas (28 mg, 1.0 mmol) as the unsaturated organic compound were added into the gas phase. The mixture was stirred at 80° C. for 16 hours. After cooling, the gas phase was purged and the reaction mixture was analyzed by gas chromatography. The yield of α-methylene-γ-butyrolactone was 10% and that of vinyl acrylate was 19%.

Example 21

Activated carbon (16 g) was added little by little into concentrated nitric acid (80 mL) and stirred at 90° C. for 5 hours. If the nitric acid was decreased with time, concentrated nitric acid was appropriately added. The solution was filtered and the obtained activated carbon (2 g) after sufficiently dried was added into a 35% aqueous solution of nitric acid (35 mL) into which palladium nitrate dihydrate (0.25 g) and tellurium dioxide (45 mg) were dissolved, and stirred at 100° C. for 4 hours. The solution was filtered and the obtained solid was dried. Then, a reduction treatment was performed by flowing nitrogen gas in which methanol was saturated at a room temperature (500 mL/min) into the obtained solid at 200° C. for 1 hour and further at 400° C. for 2 hours. Then, oxidation treatment was performed by flowing nitrogen gas containing 2.7% oxygen (500 mL/min) at 300° C. for 8 hours into the solid. Into a 10 mL autoclave, acrylic acid (3.0 g, 42 mmol) as the α,β-unsaturated carboxylic acid, the above-mentioned catalyst (0.2 g, 2 mol %) as the at least one element selected from the group consisting of elements of the Groups 8 to 12, p-methoxyphenol (3 mg) were added. The, 0.5 kg/cm$^2$ of nitrogen gas, 3.5 kg/cm$^2$ of oxygen gas, and ethylene gas (28 mg, 1.0 mmol) as the unsaturated organic compound were added into the gas phase. The mixture was stirred at 80° C. for 16 hours. After cooling, the gas phase was purged and the reaction mixture was analyzed by gas chromatography. The yield of α-methylene-γ-butyrolactone was 5.1% and that of vinyl acrylate was 3.2%

Example 22

Activated carbon (16 g) was added little by little in concentrated nitric acid (80 mL) and stirred at 90° C. for 5 hours. If the nitric acid was decreased with time, concentrated nitric acid was appropriately added. The solution was filtered, and the obtained activated carbon (2.5 g) after sufficiently dried and a 10% aqueous solution of nitric acid into which palladium nitrate dihydrate (0.37 g) was dissolved were added into 100 mL of water. Into this solution, a solution obtained by dissolving sodium borohydride (0.75 g) into water (75 mL) was added dropwise under stirring for 2 hours. The solution was filtered and the obtained solid was sufficiently dried. Into a 10 mL autoclave, acrylic acid (3.0 g, 42 mmol) as the α,β-unsaturated carboxylic acid, the above-mentioned catalyst (0.2 g, 10 mol %) as the at least one element selected from the group consisting of elements of the Groups 8 to 12, p-methoxyphenol (3 mg) were added. Then, 0.5 kg/cm$^2$ of nitrogen gas, 3.5 kg/cm$^2$ of oxygen gas, and ethylene gas (28 mg, 1.0 mmol) as the unsaturated organic compound were added into the gas phase. The mixture was stirred at 80° C. for 16 hours. After cooling, the gas phase was purged and the reaction mixture was analyzed by gas chromatography. The yield of α-methylene-γ-butyrolactone was 7.8% and that of vinyl acrylate was 6.6%.

Example 23

A catalyst was prepared by flowing 2.75% oxygen/nitrogen standard gas (flow rate: 500 mL/min) into an egg shell type 5% Pd/activated carbon (5 g) (product of Johnson Matthey), at 300° C. for 8 hours. Into a 10 mL autoclave, acrylic acid (3.0 g, 42 mmol) as the α,β-unsaturated carboxylic acid, the above-mentioned catalyst (0.2 g, 10 mol %) as the at least one element selected from the group consisting of elements of the Groups 8 to 12, and p-methoxyphenol (3 mg), norbornene (96 mg, 1.0 mmol) as the unsaturated organic compound were added. Then, 0.5 kg/cm$^2$ of nitrogen gas, 0.5 kg/cm$^2$ of oxygen gas were added into the gas phase. The mixture was stirred at 80° C. for 16 hours. After cooling, the gas phase was purged and the reaction mixture was analyzed by gas chromatography. The yield of a desired cyclic unsaturated compound was 8.3%.

Example 24

Carbon black (2.5 g) and a 10% aqueous solution of nitric acid (10 mL) into which palladium nitrate dihydrate (0.37 g) was dissolved were added into 100 mL of water. Into this solution, a solution obtained by dissolving sodium borohydride (0.75 g) into water (75 mL) was added dropwise under stirring for 2 hours. The solution was filtered and the obtained solid was sufficiently dried. Into a 10 mL autoclave, acrylic acid (3.0 g, 42 mmol) as the α,β-unsaturated carboxylic acid, the above-mentioned catalyst (0.2 g, 10 mol %) as the at least one element selected from the group consisting of elements of the Groups 8 to 12, and p-methoxyphenol (3 mg) were added. Then, 0.5 kg/cm$^2$ of nitrogen gas, 3.5 kg/cm$^2$ of oxygen gas, ethylene gas (28 mg, 1.0 mmol) as the unsaturated organic compound were added into the gas phase. The mixture was stirred at 80° C. for 16 hours. After cooling, the gas phase was purged and the reaction mixture was analyzed by gas chromatography. The yield of α-methylene-γ-butyrolactone was 4.9% and that of vinyl acrylate was 7.9%.

Example 25

A catalyst was prepared by flowing 2.75% oxygen/nitrogen standard gas (flow rate: 500 mL/min) into an egg shell type 5% Pd/activated carbon (5 g) (product of Johnson Matthey), at 400° C. for 8 hours. Into a 10 mL autoclave, acrylic acid (0.72 g, 10 mmol) as the α,β-unsaturated carboxylic acid, the above-mentioned catalyst (0.2 g, 10 mol %) as the at least one element selected from the group consisting of elements of the Groups 8 to 12, p-methoxyphenol (3 mg), and N-methylpyrrolidone (NMP) (3 mL) as the solvent were added. Then, 0.5 kg/cm$^2$ of nitrogen gas, 3.5 kg/cm$^2$ of oxygen gas, and ethylene gas (28 mg, 1.0 mmol) as the unsaturated organic compound were added into the gas phase. The mixture was stirred at 80° C. for 16 hours. After cooling, the gas phase was purged and the reaction mixture was analyzed by gas chromatography. The yield of α-methylene-γ-butyrolactone was 6.3%, and that of vinyl acrylate was 4.6%.

Example 26

A catalyst was prepared by flowing 2.75% oxygen/nitrogen standard gas (flow rate: 500 mL/min) into an egg shell type 5% Pd/activated carbon (5 g) (product of Johnson Matthey), at 400° C. for 8 hours. Into a 10 mL autoclave, acrylic acid (0.72 g, 10 mmol) as the α,β-unsaturated carboxylic acid, the above-mentioned catalyst (0.2 g, 10 mol %) as the at least one element selected from the group consisting of elements of the Groups 8 to 12, cyclohexane (3 mL) as the solvent, p-methoxyphenol (3 mg) were added. Then, 0.5 kg/cm$^2$ of nitrogen gas, 3.5 kg/cm$^2$ of oxygen gas, and ethylene gas (28 mg, 1.0 mmol) as the unsaturated organic compound were added into the gas phase. The mixture was stirred at 80° C. for 16 hours. After cooling, the gas phase was purged and the reaction mixture was analyzed by gas chromatography. The yield of α-methylene-γ-butyrolactone was 3.5% and that of vinyl acrylate was 2.3%.

Example 27

A catalyst was prepared by flowing 2.75% oxygen/nitrogen standard gas (flow rate: 500 mL/min) into an egg shell type 5% Pd/activated carbon (5 g) (product of Johnson Matthey), at 400° C. for 8 hours. Into a 10 mL autoclave, acrylic acid (3.0 g, 42 mmol) as the α,β-unsaturated carboxylic acid, the above-mentioned catalyst (0.2 g, 10 mol %) as the at least one element selected from the group consisting of elements of the Groups 8 to 12, p-methoxyphenol (3 mg) were added. Then, 3.5 kg/cm$^2$ of nitrogen gas, 0.4 kg/cm$^2$ of oxygen gas, and ethylene gas (28 mg, 1.0 mmol) as the unsaturated organic compound were added into the gas phase. The mixture was stirred at 80° C. for 16 hours. After cooling, the gas phase was purged and the reaction mixture was analyzed by gas chromatography. The yield of α-methylene-γ-butyrolactone was 6.0% and that of vinyl acrylate was 13.2%.

Example 28

A catalyst was prepared by flowing 2.75% oxygen/nitrogen standard gas (flow rate: 500 mL/min) into an egg shell type 5% Pd/activated carbon (5 g) (product of Johnson Matthey), at 400° C. for 8 hours. Into a 10 mL autoclave, acrylic acid (3.0 g, 42 mmol) as the α,β-unsaturated carboxylic acid, the above-mentioned catalyst (0.2 g, 10 mol %) as the at least one element selected from the group consisting of elements of the Groups 8 to 12, benzoquinone (0.22 g, 2.0mmol), p-methoxyphenol (3 mg) were added. Then, 3.5 kg/cm$^2$ of nitrogen gas and ethylene gas (28 mg, 1.0 mmol) as the unsaturated organic compound were added into the gas phase. The mixture was stirred at 80° C. for 16 hours. After cooling, the gas phase was purged and the reaction mixture was analyzed by gas chromatography. The α-methylene-γ-butyrolactone had a yield of 6.0% and the vinyl acrylate has a yield of 11.8%.

Example 29

Activated carbon (16 g) was added little by little in concentrated nitric acid (80 mL) and stirred at 90° C. for 5 hours. If the nitric acid was decreased with time, concentrated nitric acid was appropriately added. The solution was filtered, and the activated carbon (2.5 g) sufficiently dried and a 10% aqueous solution (10 mL) of nitric acid into which palladium nitrate dihydrate (0.37 g) was dissolved were added into 100 mL of water. Into this solution, a solution obtained by dissolving sodium borohydride (0.75 g) into water (75 mL) was added dropwise under stirring for 2 hours. Then, the pH of the solution was adjusted to 3.0 using a diluted nitric acid aqueous solution. The solution was filtered and the obtained solid was sufficiently dried. Into a 10 mL autoclave, acrylic acid (3.0 g, 42 mmol) as the α,β-unsaturated carboxylic acid, the above-mentioned catalyst (0.2 g, 10 mol %) as the at least one element selected from the group consisting of elements of the Groups 8 to 12, p-methoxyphenol (3 mg) were added. Then, 0.5 kg/cm$^2$ of nitrogen gas, 3.5 kg/cm$^2$ of oxygen gas, and ethylene gas (28 mg, 1.0 mmol) as the unsaturated organic compound were added into the gas phase. The mixture was stirred at 80° C. for 16 hours. After cooling, the gas phase was purged and the reaction mixture was analyzed by gas chromatography. The yield of α-methylene-γ-butyrolactone was 6.6% and that of vinyl acrylate was 6.6%.

Example 30

A catalyst was prepared by flowing 2.75% oxygen/nitrogen standard gas (flow rate: 500 mL/min) into 5% Pd/activated carbon (5 g) (product of N.E. CHEMCAT Corp.), at 400° C. for 8 hours. Into a 10 mL autoclave, acrylic acid (3.0 g, 42 mmol) as the α,β-unsaturated carboxylic acid, the above-mentioned catalyst (0.2 g, 10 mol %) as the at least one element selected from the group consisting of elements of the Groups 8 to 12, and p-methoxyphenol (3 mg) were added. Then, 0.5 kg/cm$^2$ of nitrogen gas, 3.5 kg/cm$^2$ of oxygen gas, and ethylene gas (28 mg, 1.0 mmol) as the unsaturated organic compound were added into the gas phase. The mixture was stirred at 80° C. for 16 hours. After cooling, the gas phase was purged and the reaction mixture was analyzed by gas chromatography. The yield of α-methylene-γ-butyrolactone was 11% and that of vinyl acrylate was 7%.

Example 31

A catalyst was prepared by flowing 2.75% oxygen/nitrogen standard gas (flow rate: 500 mL/min) into an egg shell type 5% Pd/activated carbon (5 g) (product of Johnson Matthey), at 400° C. for 8 hours. Into a 10 mL autoclave, acrylic acid (3.0 g, 42 mmol) as the α,β-unsaturated carboxylic acid, the above-mentioned catalyst (0.2 g, 10 mol %) as the at least one element selected from the group consisting of elements of the Groups 8 to 12, and p-methoxyphenol (3 mg) were added. Then, 0.5 kg/cm$^2$ of nitrogen gas, 3.5 kg/cm$^2$ of oxygen gas, and propylene gas (42 mg, 1.0 mmol) as the unsaturated organic compound were added into the gas phase. The mixture was stirred at 80° C. for 16 hours. After cooling, the gas phase was purged and the reaction mixture was analyzed by gas chromatography. The yield of γ-methyl-α-methylene-γ-butyrolactone was 13% and that of straight-chain unsaturated acrylic ester was less than 0.1%.

Example 32

A catalyst was prepared by flowing 2.75% oxygen/nitrogen standard gas (flow rate: 500 mL/min) into an egg shell type 5% Pd/activated carbon (5 g) (product of Johnson Matthey), at 400° C. for 8 hours. Into a 10 mL autoclave, acrylic acid (3.0 g, 42 mmol) as the α,β-unsaturated carboxylic acid, the above-mentioned catalyst (0.2 g, 10 mol %) as the at least one element selected from the group consisting of elements of the Groups 8 to 12, and p-methoxyphenol (3 mg) were added. Then, 0.5 kg/cm$^2$ of nitrogen gas, 3.5 kg/cm$^2$ of oxygen gas, and 1-butene gas (56 mg, 1.0 mmol) as the unsaturated organic compound were added into the gas phase. The mixture was stirred at 80° C. for 16 hours. After cooling, the gas phase was purged and the reaction mixture was analyzed by gas chromatography. The yield of γ-ethyl-α-methylene-γ-butyrolactone was 15% and that of straight-chain unsaturated acrylic ester was less than 0.1%.

The reaction mechanisms in Examples 19 to 22 and 24 to 30 are also the same as in FIG. 1. The reaction mechanisms in Examples 23, 31, and 32 are the same as in FIG. 1, except that norbornene, propylene, and 1-butene were used as the unsaturated organic compound respectively, instead of ethylene. Table 2 shows the results in Examples 19 to 32.

Example 33

(A method for producing a cyclic unsaturated compound by reacting an α,β-unsaturated carboxylic acid with an unsaturated organic compound, the method including a step of reoxidizing a compound including at least one element selected from the group consisting of elements of the Groups 8 to 12 using a reoxidant agent in the presence of the compound including at least one element selected from the group consisting of elements of the Groups 8 to 12, a basic compound and a solvent)

A cyclic unsaturated compound was produced under the following conditions.

Into a 10 mL autoclave, acrylic acid (0.43 g, 6.0 mmol) as the α,β-unsaturated carboxylic acid, benzoquinone (0.11 g, 1.0 mmol), sodium acrylate (9.0 mg, 0.10 mmol) as the basic compound, palladium acetate (11 mg, 5 mol %) as the compound including at least one element selected from the group consisting of elements of the Groups 8 to 12, and N-methylpyrrolidone (NMP) (3 mL) as the solvent were added. Then, 0.5 kg/cm$^2$ of nitrogen gas, 2 kg/cm$^2$ of oxygen gas, and ethylene gas (28 mg, 1.0 mmol) as the unsaturated organic compound were added into the gas phase. The mixture was stirred at 50° C. for 36 hours.

After cooling, the gas phase was purged and the reaction mixture was analyzed by gas chromatography. The yield of α-methylene-γ-butyrolactone was 5.7% and that of vinyl acetate was 5.5%.

Also in Examples 34 to 64, the production methods were the same as in Example 33, except that the proportion and the reaction conditions shown in Table 3 were changed. The reaction mechanisms in Examples 33 to 64 were also the same as in FIG. 1. Table 3 shows these results.

Example 65

Into a test tube, acrylic acid (0.62 g, 8.6 mmol) as the α,β-unsaturated carboxylic acid, benzoquinone (43 mg, 0.40 mmol), sodium acrylate (9.0 mg, 0.10 mmol) as the basic compound, palladium acetate (56 mg, 25 mol %) as the compound including at least one element selected from the group consisting of elements of the Groups 8 to 12, norbornene (94 mg, 1.0 mmol) as the unsaturated organic compound, and dimethylacetoamide (DMA) (6 mL) as the solvent were added. The gas phase was composed of atmospheric pressure air. The mixture was stirred at 70° C. for 24 hours. After cooling, the gas phase was purged, and the reaction mixture was analyzed by gas chromatography. The desired product was obtained in a 38% yield.

Also in Examples 66 and 67, the production methods were the same as in Example 65, except that the proportion and the reaction conditions shown in Table 4 were changed. The reaction mechanisms in Examples 65 to 67 were the same as in FIG. 1, except that norbornene was used as the unsaturated organic compound instead of ethylene. Table 4 shows these results.

Example 68

Into a test tube, acrylic acid (0.43 g, 6.0 mmol) as the α,β-unsaturated carboxylic acid, benzoquinone (0.11 g, 1.0 mmol), sodium acrylate (9.0 mg, 0.10 mmol) as the basic compound, palladium acetate (56 mg, 25 mol %) as the compound including at least one element selected from the group consisting of elements of the Groups 8 to 12, 1-octene (0.11 g, 1.0 mmol) as the unsaturated organic compound, and N-methylpyrrolidone (NMP) (3 mL) as the solvent were added. The gas phase was composed of atmospheric pressure air. The mixture was stirred at 70° C. for 24 hours. After cooling, the gas phase was purged, and then the reaction mixture was analyzed by gas chromatography. The desired product was obtained in a 25% yield. Also in Example 69, the production method was the same as in Example 68, except that the proportion and the reaction conditions shown in Table 5 were changed. The reaction mechanisms in Examples 68 and 69 were the same as in FIG. 1, except that 1-octene was used as the unsaturated organic compound instead of ethylene. Table 5 shows these results.

Example 70

Into a 10 mL autoclave, acrylic acid (0.72 g, 10 mmol) as the α,β-unsaturated carboxylic acid, benzoquinone (0.22 g, 2.0 mmol), sodium acrylate (9.0 mg, 0.10 mmol) as the basic compound, palladium acetate (56 mg, 25 mol %) as the compound including at least one element selected from the group consisting of elements of the Groups 8 to 12, N-cyclohexylpyrrolidone (NCP) (3 mL) as the solvent, and p-methoxyphenol (3 mg) were added. Then, 0.5 kg/cm² of nitrogen gas, 0.5 kg/cm² of oxygen gas, and propylene gas (42 mg, 1.0 mmol) as the unsaturated organic compound were added into the gas phase. The mixture was stirred at 50° C. for 16 hours. After cooling, the gas phase was purged and the reaction mixture was analyzed by gas chromatography. The yield of γ-methyl-α-methylene-γ-butyrolactone was 55% and that of linear unsaturated acrylic ester was 1.9%.

Example 71

Into a 10 mL autoclave, acrylic acid (0.72 g, 10 mmol) as the α,β-unsaturated carboxylic acid, benzoquinone (0.22 g, 2.0 mmol), sodium acrylate (9.0 mg, 0.10 mmol) as the basic compound, palladium acetate (56 mg, 25 mol %) as the compound including at least one element selected from the group consisting of elements of the Groups 8 to 12, N-methylpyrrolidone (NMP) (3 mL) as the solvent, and p-methoxyphenol (3 mg) were added. Then, 0.5 kg/cm² of nitrogen gas, 0.5 kg/cm² of oxygen gas, and 1-butene gas (56 mg, 1.0 mmol) as the unsaturated organic compound were added into the gas phase. The mixture was stirred at 50° C. for 16 hours. After cooling, the gas phase was purged and the reaction mixture was analyzed by gas chromatography. The yield of γ-ethyl-α-methylene-γ-butyrolactone was 52% and that of linear unsaturated acrylic ester was 0.2%.

Example 72

Into a 10 mL autoclave, acrylic acid (0.72 g, 10 mmol) as the α,β-unsaturated carboxylic acid, benzoquinone (0.22 g, 2.0 mmol), sodium acrylate (9.0 mg, 0.10 mmol) as the basic compound, tetrakis(acetonitrile)palladium tetrafluoroborate (89 mg, 25 mol %) as the compound including at least one element selected from the group consisting of elements of the Groups 8 to 12, N-cyclohexylpyrrolidone (NCP) (3 mL) as the solvent, and p-methoxyphenol (3 mg) were added. Then, 0.5 kg/cm² of nitrogen gas, 0.5 kg/cm² of oxygen gas, and propylene gas (42 mg, 1.0 mmol) as the unsaturated organic compound were added into the gas phase. The mixture was stirred at 50° C. for 16 hours. After cooling, the gas phase was purged and the reaction mixture was analyzed by gas chromatography. The yield of γ-methyl-α-methylene-γ-butyrolactone was 34% and that of linear unsaturated acrylic ester was 0.1%.

Example 73

Into a 10 mL autoclave, acrylic acid (0.72 g, 10 mmol) as the α,β-unsaturated carboxylic acid, benzoquinone (0.22 g, 2.0 mmol), sodium acrylate (9.0 mg, 0.10 mmol) as the basic compound, palladium acetate (22 mg, 10 mol %) as the compound including at least one element selected from the group consisting of elements of the Groups 8 to 12, vinyl acetate (0.17 g, 2.0 mmol) as the unsaturated organic compound, N-methylpyrrolidone (NMP) (3 mL) as the solvent, and p-methoxyphenol (3 mg) were added. Then, 0.5 kg/cm² of nitrogen gas, 0.5 kg/cm² of oxygen gas were added into the gas phase. The mixture was stirred at 50° C. for 16 hours. After cooling, the gas phase was purged and the reaction mixture was analyzed by gas chromatography. The yield of γ-acetoxy-α-methylene-γ-butyrolactone was 23% and that of vinyl acrylate was 2.0%.

Example 74

Into a 10 mL autoclave, acrylic acid (0.43 g, 6 mmol) as the α,β-unsaturated carboxylic acid, benzoquinone (0.033 g, 0.3 mmol), palladium acetate (4.7 mg, 0.4 mol %) as a compound including an element of the Groups 8 to 12, [V$_2$PMo$_{10}$O$_{40}$] polyoxometalate containing tetrabutylammonium (TBA) as some of cations (TBA) [V$_2$PMo$_{10}$O$_{40}$] (30mg) as the promoter, and benzonitrile (1.5 mL) as the solvent were added. Then, 0.5 kg/cm² of nitrogen gas, 3.5 kg/cm² of oxygen gas, and 1-butene gas (290 mg, 5.2 mmol) as the unsaturated organic compound were added into the gas phase. The mixture was stirred at 50° C. for 16 hours. After cooling, the gas phase was purged and the reaction mixture was analyzed by gas chromatography. The yield of γ-ethyl-α-methylene-γ-butyrolactone was 10%. Also in Examples 75 to 96, the production methods were same as in Example 74, except that the proportion and the reaction conditions shown in Table 7 were changed. The reaction mechanisms in Examples 74 to 96 were also the same as in FIG. 1. Table 7 shows these results. The polyoxometalates containing tetrabutylammonium (TBA) as some of cations were prepared by dissolving H$_5$[V$_2$PMo$_{10}$O$_{40}$], (NH$_4$)$_8$H$_3$[V$_8$PMo$_4$O$_{40}$], Na$_6$H[V$_3$SiW$_9$O$_{40}$] into ion-exchanged waters, respectively then adding tetrabutylammonium bromide corresponding to the molar of cation into the solution, and then stirring and filtering the solution, washing the filtrate with ion-exchanged water, and then drying the obtained substance. 10 wt % (NH$_4$)[V$_2$PMo$_{10}$O$_{40}$]/C was prepared by dissolving (NH$_4$)$_5$[V$_2$PMoO$_{40}$] into ion-exchanged water, and adding a weighted quantity of activated carbon (C) into the solution, stirring and filtering the solution, washing the filtrate with ion-exchanged water, and then drying the obtained substance.

Example 97

Into a 10 mL autoclave, acrylic acid (0.10 g, 1.4 mmol) as the α,β-unsaturated carboxylic acid, palladium trifluoroacetate (6.1 mg, 1.3 mol %) as the compound including an element of the Groups 8 to 12, copper acetate (3.3 mg, 1.3 mol %) as the promoter, and toluene (2.5 mL) as the solvent were added. Then, 1 kg/cm² of nitrogen gas, 3.5 kg/cm² of oxygen gas, 1-butene gas (300 mg, 5.4 mmol) as the unsaturated organic compound were added into the gas phase. The mixture was stirred at 50° C. for 16 hours. After cooling, the gas phase was purged and the reaction mixture was analyzed by gas chromatography. The yield of γ-ethyl-α-methylene-γ-butyrolactone was 25%. Also in Examples 98 to 120, the production methods were the same as in Example 97, except that the proportion and the reaction conditions shown in Table 8 were changed. The reaction mechanisms in Examples 98 to 120 were the same as in FIG. 1. Table 8 shows these results.

Example 121

Into a 10 mL autoclave, crotonic acid (43 mg, 0.5 mmol) as the α,β-unsaturated carboxylic acid, palladium trifluoroacetate (6.6 mg, 4 mol %) as the compound including an element of the Groups 8 to 12, copper acetate (5.4 mg, 6 mol %) as the promoter, and toluene (4 mL) as the solvent were added. Then, 1 kg/cm² of nitrogen gas, 2 kg/cm² of oxygen gas, 1-butene gas (390 mg, 7.0 mmol) as the unsaturated organic compound were added into the gas phase. The mixture was stirred at 50° C. for 16 hours. After cooling, the gas phase was purged and the reaction mixture was analyzed by gas chromatography. The yield of a desired γ-ethyl-α-vinyl-γ-butyrolactone was 70% and that of acyclic unsaturated ester was less than 0.1%.

Comparative Example 1

Into a 10 mL autoclave, crotonic acid (43 mg, 0.5 mmol) as the α,β-unsaturated carboxylic acid and toluene (4 mL) as the solvent were added. Then, 1 kg/cm$^2$ of nitrogen gas, 2 kg/cm$^2$ of oxygen gas, 1-butene gas (390 mg, 7.0 mmol) as the unsaturated organic compound were added into the gas phase. The mixture was stirred at 50° C. for 16 hours. After cooling, the gas phase was purged and the reaction mixture was analyzed by gas chromatography. The yield of a desired γ-ethyl-α-vinyl-γ-butyrolactone was 0%.

The above-mentioned Examples show the followings. That is, it is shown that the desired cyclic unsaturated compound is obtained by reacting the α,β-unsaturated carboxylic acid with the unsaturated organic compound in the presence of the above-mentioned catalyst. Particularly, it is shown that if the catalyst essentially includes at least one element selected from the group consisting of elements of the Groups 8 to 12, the advantageous effect in which the yield of the cyclic unsaturated compound can be sufficiently increased is remarkably exhibited.

Thus, it is shown that if the above-mentioned production method includes the step of reacting the α,β-unsaturated carboxylic acid with the unsaturated organic compound in the presence of the catalyst, the advantageous effects in which generation of acyclic unsaturated compounds can be sufficiently suppressed and the reaction rate and the yield can be increased are remarkably exhibited.

TABLE 1

| | Catalyst (mol %) | Solvent (mL) | Acrylic acid (mmol) | Ethylene (mmol) | Reoxidant agent and promoter (mmol) | Basic compound (mmol) |
|---|---|---|---|---|---|---|
| Example 1 | Pd(OAc)$_2$ (5) | NMP (3) | 6 | 1 | Benzoquinone (2) + Molecular oxygen | AANa (0.03) |
| Example 2 | Pd(OAc)$_2$ (25) | BN (3) | 6 | 1 | Benzoquinone (1) + Molecular oxygen | AANa (0.1) |
| Example 3 | PdCl$_2$ (5) | DMA (2) | 2 | 1 | Molecular oxygen | AANa (0.2) |
| Example 4 | Pd(OAc)$_2$ (25) | None | 40 | 1 | Benzoquinone (2) + Molecular oxygen | AANa (0.1) |
| Example 5 | Pd(OAc)$_2$ (25) | NMP (3) | 6 | 1 | Benzoquinone (2) + Molecular oxygen | AANa (0.1) |
| Example 6 | Pd(OAc)$_2$ (25) | NMP (3) | 10 | 1 | Benzoquinone (2) + Molecular oxygen | AANa (0.1) |
| Example 7 | Pd(OAc)$_2$ (25) | NMP (3) | 10 | 1 | Benzoquinone (2) + Molecular oxygen | AANa (0.1) |
| Example 8 | Pd(OAc)$_2$ (25) | NMP (3) | 10 | 1 | Benzoquinone (2) + Molecular oxygen | AANa (0.1) |
| Example 9 | Pd(OAc)$_2$ (25) | NMP (3) | 10 | 2 | Benzoquinone (2) + Molecular oxygen | AANa (0.1) |
| Example 10 | Pd(OAc)$_2$ (25) | NMP (6) | 10 | 1 | Benzoquinone (2) + Molecular oxygen | AANa (0.1) |
| Example 11 | Pd(OAc)$_2$ (25) | NMP (3) | 10 | 1 | Benzoquinone (2) + Molecular oxygen | None |
| Example 12 | Pd(OAc)$_2$ (5) | NMP (3) | 6 | 1 | Cu(OAc)$_2$ (0.06) + Catechol (0.06) + Molecular oxygen | None |
| Example 13 | Pd(MeCN)$_4$(BF$_4$)$_2$ (25) | NMP (3) | 6 | 1 | Benzoquinone (2) + Molecular oxygen | AANa (0.1) |
| Example 14 | Pd(OAc)$_2$ (5) | DMSO (3) | 10 | 1 | Molecular oxygen | AANa (0.1) |
| Example 15 | Pd(OAc)$_2$ (5) | None | 40 | 1 | Benzoquinone (0.3) + MnO$_2$ (1) + Molecular oxygen | None |
| Example 16 | Pd(OAc)$_2$ (5) | NMP (3) | 10 | 1 | Benzoquinone (0.3) + MnO$_2$ (1) + Molecular oxygen | AANa (0.05) |
| Example 17 | Pd(OAc)$_2$ (5) | NMP (3) | 10 | 1 | Benzoquinone (0.3) + MnO$_2$ (1) + Molecular oxygen | None |
| Example 18 | Pd(OAc)$_2$ (5) | None | 40 | 1 | Molecular oxygen | None |

| | N$_2$ (kg/cm$^2$) | O$_2$ (kg/cm$^2$) | Temperature (° C.) | Time (h) | Yield (A) of exo-cyclic unsaturated compound (%) | Yield (B) of acyclic unsaturated compound (%) | (A/B) | Maximum distribution diameter of multi-nuclear compound (nm) |
|---|---|---|---|---|---|---|---|---|
| Example 1 | 0.5 | 3.5 | 50 | 16 | 25 | 18 | 1.4 | 5.5 |
| Example 2 | 0.5 | 3.5 | 50 | 16 | 18 | 42 | 0.4 | 6.2 (+Pd black) |
| Example 3 | 0.5 | 3.5 | 50 | 16 | 2.2 | 15 | 0.1 | 5.8 |
| Example 4 | 0.5 | 3.5 | 50 | 16 | 11 | 35 | 0.3 | 9.5 (+Pd black) |
| Example 5 | 0.5 | 3.5 | 50 | 16 | 54 | 6.8 | 7.9 | 3.2 |
| Example 6 | 0.5 | 3.5 | 50 | 4 | 44 | 7.4 | 5.9 | 3.1 |
| Example 7 | 0.5 | 3.5 | 50 | 16 | 60 | 8.0 | 7.5 | 2.3 |
| Example 8 | 0.5 | 3.5 | 60 | 16 | 49 | 8.7 | 5.6 | 3.7 |
| Example 9 | 0.5 | 3.5 | 50 | 16 | 42 | 15 | 2.8 | 3.3 |
| Example 10 | 0.5 | 3.5 | 50 | 16 | 65 | 8.7 | 7.5 | 2.4 |
| Example 11 | 0.5 | 3.5 | 50 | 16 | 26 | 10 | 2.6 | 8.3 |
| Example 12 | 0.5 | 3.5 | 50 | 16 | 23 | 12 | 1.9 | 4.8 |
| Example 13 | 0.5 | 3.5 | 50 | 16 | 5.6 | 42 | 0.1 | 59 |
| Example 14 | 0.5 | 3.5 | 50 | 16 | 0.2 | 0.1 | 2.0 | mononuclear complex (not detected) |
| Example 15 | 0.5 | 3.5 | 50 | 16 | 3.8 | 30 | 0.1 | 9.8 (+Pd black) |
| Example 16 | 0.5 | 3.5 | 50 | 16 | 4.5 | 3.1 | 1.5 | — |

TABLE 1-continued

| | | | | | | | | |
|---|---|---|---|---|---|---|---|---|
| Example 17 | 0.5 | 3.5 | 50 | 16 | 2.4 | 2.7 | 0.9 | — |
| Example 18 | 0.5 | 3.5 | 50 | 16 | 0.4 | 2.4 | 0.2 | — |

TABLE 2

| | Catalyst (mol %) | Solvent (mL) | Acrylic acid (mmol) | Unsaturated organic compound (mmol) | Reoxidant agent (mmol) | N₂ (kg/cm²) |
|---|---|---|---|---|---|---|
| Example 19 | Pd/C (10) | None | 42 | Ethylene (1) | Molecular oxygen | 0.5 |
| Example 20 | Pd/C (10) | None | 42 | Ethylene (1) | Molecular oxygen | 0.5 |
| Example 21 | Pd/Te/C (2) | None | 42 | Ethylene (1) | Molecular oxygen | 0.5 |
| Example 22 | Pd/C (10) | None | 42 | Ethylene (1) | Molecular oxygen | 0.5 |
| Example 23 | Pd/C (10) | None | 42 | Norbornene (1) | Molecular oxygen | 0.5 |
| Example 24 | Pd/C (10) | None | 42 | Ethylene (1) | Molecular oxygen | 0.5 |
| Example 25 | Pd/C (10) | NMP (3) | 10 | Ethylene (1) | Molecular oxygen | 0.5 |
| Example 26 | Pd/C (10) | Cyclohexane (3) | 10 | Ethylene (1) | Molecular oxygen | 0.5 |
| Example 27 | Pd/C (10) | None | 42 | Ethylene (1) | Molecular oxygen | 3.5 |
| Example 28 | Pd/C (10) | None | 42 | Ethylene (1) | Benzoquinone (2) | 3.5 |
| Example 29 | Pd/C (10) | None | 42 | Ethylene (1) | Molecular oxygen | 0.5 |
| Example 30 | Pd/C (10) | None | 42 | Ethylene (1) | Molecular oxygen | 0.5 |
| Example 31 | Pd/C (10) | None | 42 | Propylene (1) | Molecular oxygen | 0.5 |
| Example 32 | Pd/C (10) | None | 42 | 1-butene (1) | Molecular oxygen | 0.5 |

| | O₂ (kg/cm²) | Temperature (° C.) | Time (h) | Yield (A) of exo-cyclic unsaturated compound (%) | Yield (A) of acyclic unsaturated compound (%) | (A/B) |
|---|---|---|---|---|---|---|
| Example 19 | 3.5 | 80 | 16 | 15 | 18 | 0.8 |
| Example 20 | 3.5 | 80 | 16 | 10 | 19 | 0.5 |
| Example 21 | 3.5 | 80 | 16 | 5.1 | 3.2 | 1.6 |
| Example 22 | 3.5 | 80 | 16 | 7.8 | 6.6 | 1.2 |
| Example 23 | 0.5 | 80 | 16 | 8.3 | 0 | — |
| Example 24 | 3.5 | 80 | 16 | 4.9 | 7.9 | 0.6 |
| Example 25 | 3.5 | 80 | 16 | 6.3 | 4.6 | 1.4 |
| Example 26 | 3.5 | 80 | 16 | 3.5 | 2.3 | 1.5 |
| Example 27 | 0.4 | 80 | 16 | 6.0 | 13.2 | 0.5 |
| Example 28 | 0 | 80 | 16 | 6.0 | 11.8 | 0.5 |
| Example 29 | 3.5 | 80 | 16 | 6.6 | 6.6 | 1.0 |
| Example 30 | 3.5 | 80 | 16 | 11 | 7 | 1.6 |
| Example 31 | 3.5 | 80 | 16 | 13 | Less than 0.1 | >130 |
| Example 32 | 3.5 | 80 | 16 | 15 | Less than 0.1 | >150 |

TABLE 3

| | Catalyst (mol %) | Solvent (mL) | Acrylic acid (mmol) | Ethylene (mmol) | Reoxidant agent and promoter (mmol) | Basic compound (mmol) |
|---|---|---|---|---|---|---|
| Example 33 | Pd(OAc)₂ (5) | NMP (3) | 6 | 1 | Benzoquinone (1) + Molecular oxygen | AANa (0.1) |
| Example 34 | Pd(OAc)₂ (5) | DMF (3) | 6 | 1 | Benzoquinone (1) + Molecular oxygen | AANa (0.1) |
| Example 35 | Pd(OAc)₂ (5) | MeCN (3) | 6 | 1 | Benzoquinone (1) + Molecular oxygen | AANa (0.1) |
| Example 36 | Pd(OAc)₂ (5) | DMA (3) | 6 | 1 | Benzoquinone (1) + Molecular oxygen | AANa (0.1) |
| Example 37 | Pd(OAc)₂ (5) | BN (3) | 6 | 1 | Benzoquinone (1) + Molecular oxygen | AANa (0.1) |
| Example 38 | Pd(OAc)₂ (5) | DME (3) | 6 | 1 | Benzoquinone (1) + Molecular oxygen | AANa (0.1) |
| Example 39 | Pd(OAc)₂ (5) | CH₂Cl₂ (3) | 6 | 1 | Benzoquinone (1) + Molecular oxygen | AANa (0.1) |
| Example 40 | Pd(OAc)₂ (5) | AcOBu (3) | 6 | 1 | Benzoquinone (1) + Molecular oxygen | AANa (0.1) |
| Example 41 | Pd(OAc)₂ (5) | DMA (1) | 15 | 1 | Benzoquinone (1) + Molecular oxygen | AANa (0.1) |
| Example 42 | Pd(OAc)₂ (5) | DMSO (1) | 15 | 1 | Molecular oxygen | AANa (0.1) |
| Example 43 | PdCl₂ (5) | DMA (2) | 6 | 1 | Molecular oxygen | AANa (0.1) |
| Example 44 | Pd(OAc)₂ (25) | None | 45 | 1 | Benzoquinone (0.4) + Molecular oxygen | AANa (0.2) |
| Example 45 | Pd(OAc)₂ (25) | NMP (3) | 6 | 1 | Molecular oxygen | AANa (0.1) |
| Example 46 | Pd(OAc)₂ (25) | NMP (3) | 6 | 1 | Benzoquinone (0.3) + Molecular oxygen | AANa (0.1) |
| Example 47 | Pd(OAc)₂ (25) | NMP (3) | 6 | 1 | Benzoquinone (0.3) + MnO₂ (1) + Molecular oxygen | AANa (0.1) |
| Example 48 | Pd(OAc)₂ (25) | NMP (3) | 6 | 1 | Benzoquinone (0.7) + Molecular oxygen | AANa (0.1) |
| Example 49 | Pd(OAc)₂ (25) | NMP (3) | 6 | 1 | Benzoquinone (0.7) + Molecular oxygen | AANa (0.3) |

TABLE 3-continued

| | | | | | | |
|---|---|---|---|---|---|---|
| Example 50 | Pd(OAc)$_2$ (25) | NMP (3) | 6 | 1 | Benzoquinone (2.2) + Molecular oxygen | AANa (0.1) |
| Example 51 | Pd(OAc)$_2$ (25) | NMP (3) | 10 | 1 | Benzoquinone (2.2) + Molecular oxygen | AANa (0.1) |
| Example 52 | Pd(OAc)$_2$ (25) | DMA (3) | 6 | 1 | Benzoquinone (2.2) + Molecular oxygen | AANa (0.1) |
| Example 53 | Pd(OAc)$_2$ (25) | DMI (3) | 6 | 1 | Benzoquinone (2.2) + Molecular oxygen | AANa (0.1) |
| Example 54 | Pd(OAc)$_2$ (25) | DMF (3) | 6 | 1 | Benzoquinone (2.2) + Molecular oxygen | AANa (0.1) |
| Example 55 | Pd(OAc)$_2$ (25) | NCP (3) | 6 | 1 | Benzoquinone (3.0) + Molecular oxygen | AANa (0.1) |
| Example 56 | Pd(OAc)$_2$ (25) | BMI (3) | 6 | 1 | Benzoquinone (2.2) + Molecular oxygen | AANa (0.1) |
| Example 57 | Pd(OAc)$_2$ (25) | NMP (3) | 6 | 1 | Benzoquinone (2.2) | AANa (0.1) |
| Example 58 | Pd(OAc)$_2$ (25) | NMP (3) | 6 | 1 | Benzoquinone (2.2) + Molecular oxygen | Li$_2$CO$_3$ (0.1) |
| Example 59 | Pd(OAc)$_2$ (25) | NMP (3) | 10 | 1 | Benzoquinone (2.2) + Molecular oxygen | CaCO$_3$ (0.1) |
| Example 60 | Pd(OAc)$_2$ (12) | NMP (3) | 6 | 1 | Benzoquinone (2.2) + Molecular oxygen | AANa (0.1) |
| Example 61 | Pd(OAc)$_2$ (10) | NMP (1) | 2 | 1 | Benzoquinone (0.1) + H$_5$PV$_2$Mo$_{10}$O$_{40}$ (0.005) + Molecular oxygen | AANa (0.05) |
| Example 62 | Pd(OAc)$_2$ (25) | NMP (3) | 6 | 1 | None | None |
| Example 63 | Pd(OAc)$_2$ (25) | NMP (3) | 6 | 1 | Benzoquinone (0.3) + Molecular oxygen | None |
| Example 64 | Pd(OAc)$_2$ (25) | NMP (3) | 6 | 1 | Benzoquinone (0.3) + MnO$_2$ (1) + Molecular oxygen | None |

| | N$_2$ (kg/cm$^2$) | O$_2$ (kg/cm$^2$) | Temperature (° C.) | Time (h) | Yield (A) of exo-cyclic unsaturated compound (%) | Yield of endo-cyclic unsaturated compound (%) | Yield (B) of acyclic unsaturated compound (%) | (A/B) |
|---|---|---|---|---|---|---|---|---|
| Example 33 | 0.5 | 2 | 50 | 36 | 5.7 | <0.1 | 5.5 | 1.0 |
| Example 34 | 0.5 | 2 | 50 | 36 | 2.2 | <0.1 | 3.7 | 0.6 |
| Example 35 | 0.5 | 2 | 50 | 36 | 1.0 | <0.1 | 10 | 0.1 |
| Example 36 | 0.5 | 2 | 50 | 36 | 3.1 | <0.1 | 3.9 | 0.8 |
| Example 37 | 0.5 | 2 | 50 | 36 | 5.8 | <0.1 | 29 | 0.2 |
| Example 38 | 0.5 | 2 | 50 | 36 | 1.7 | <0.1 | 5.3 | 0.3 |
| Example 39 | 0.5 | 2 | 50 | 36 | 0.5 | <0.1 | 8.3 | 0.1 |
| Example 40 | 0.5 | 2 | 50 | 36 | 2.0 | <0.1 | 12 | 0.2 |
| Example 41 | 0.5 | 2 | 50 | 36 | 5.9 | <0.1 | 18 | 0.3 |
| Example 42 | 0.5 | 6 | 50 | 16 | 0.7 | <0.1 | 0.5 | 1.4 |
| Example 43 | 0.5 | 3.5 | 50 | 16 | 1.4 | <0.1 | 12 | 0.1 |
| Example 44 | 0.5 | 3.5 | 50 | 16 | 11 | 1.1 | 36 | 0.3 |
| Example 45 | 0.5 | 3.5 | 50 | 16 | 16 | 1.3 | 5.1 | 3.1 |
| Example 46 | 0.5 | 3.5 | 50 | 16 | 33 | 4.8 | 6.3 | 5.2 |
| Example 47 | 0.5 | 3.5 | 50 | 16 | 29 | 3.5 | 6.6 | 4.4 |
| Example 48 | 0.5 | 3.5 | 50 | 16 | 37 | 4.5 | 4.8 | 7.7 |
| Example 49 | 0.5 | 3.5 | 50 | 16 | 31 | 3.9 | 5.8 | 5.3 |
| Example 50 | 0.5 | 3.5 | 50 | 16 | 54 | 4.8 | 6.8 | 7.9 |
| Example 51 | 0.5 | 3.5 | 50 | 16 | 60 | 5.0 | 8.0 | 7.5 |
| Example 52 | 0.5 | 3.5 | 50 | 16 | 47 | 5.2 | 7.7 | 6.1 |
| Example 53 | 0.5 | 3.5 | 50 | 16 | 48 | 4.9 | 8.6 | 5.5 |
| Example 54 | 0.5 | 3.5 | 50 | 16 | 24 | 2.0 | 5.9 | 4.1 |
| Example 55 | 0.5 | 3.5 | 50 | 16 | 50 | 5.8 | 5.5 | 9.1 |
| Example 56 | 0.5 | 3.5 | 50 | 16 | 33 | 3.1 | 2.2 | 15 |
| Example 57 | 0.5 | 0 | 50 | 16 | 36 | 5.5 | 5.2 | 6.9 |
| Example 58 | 0.5 | 3.5 | 50 | 16 | 37 | 5.6 | 5.1 | 7.3 |
| Example 59 | 0.5 | 3.5 | 50 | 16 | 44 | 5.1 | 8.3 | 5.3 |
| Example 60 | 0.5 | 3.5 | 50 | 16 | 44 | 4.9 | 15 | 3.0 |
| Example 61 | 0.5 | 3.5 | 50 | 16 | 7.1 | 0.8 | 1.7 | 4.2 |
| Example 62 | 0.5 | 0 | 50 | 16 | 0.5 | <0.1 | 1.3 | 0.4 |
| Example 63 | 0.5 | 3.5 | 50 | 16 | 3.6 | <0.1 | 3.9 | 0.9 |
| Example 64 | 0.5 | 3.5 | 50 | 16 | 6.8 | <0.1 | 3.0 | 2.3 |

TABLE 4

| | Catalyst (mol %) | Solvent (mL) | Acrylic acid (mmol) | Norbornene (mmol) | Reoxidant agent (mmol) | Basic compound (mmol) | Temperature (° C.) | Time (h) | Yield of exo-cyclic unsaturated compound (%) |
|---|---|---|---|---|---|---|---|---|---|
| Example 65 | Pd(OAc)$_2$ (25) | DMA (6) | 8.6 | 1 | Benzoquinone (0.4) + air | AANa (0.1) | 70 | 24 | 38 |
| Example 66 | Pd(OAc)$_2$ (25) | NMP (6) | 14 | 1 | Benzoquinone (2.5) + air | AANa (0.1) | 70 | 24 | 54 |
| Example 67 | Pd(OAc)$_2$ (25) | NMP (6) | 14 | 1 | Benzoqiunone (2.5) + air | None | 70 | 24 | 29 |

TABLE 5

| | Catalyst (mol %) | Solvent (mL) | Acrylic acid (mmol) | 1-octene (mmol) | Reoxidant agent (mmol) | Basic compound (mmol) | Temperature (° C.) | Time (h) | Yield of exo-cyclic unsaturated compound (%) |
|---|---|---|---|---|---|---|---|---|---|
| Example 68 | Pd(OAc)$_2$ (25) | NMP (3) | 6 | 1 | Benzoquinone (1.0) + air | AANa (0.1) | 70 | 24 | 25 |
| Example 69 | Pd(OAc)$_2$ (25) | NMP (3) | 6 | 1 | Benzoquinone (1.0) + air | None | 70 | 24 | 9 |

TABLE 6

| | Catalyst (mol %) | Solvent (mL) | Acrylic acid (mmol) | Unsaturated organic compound (mmol) | Reoxidant agent (mmol) | Basic compound (mmol) |
|---|---|---|---|---|---|---|
| Example 70 | Pd(OAc)$_2$ (25) | NCP (3) | 10 | Propylene (1) | Benzoquinone (2) + Molecular oxygen | AANa (0.1) |
| Example 71 | Pd(OAc)$_2$ (25) | NMP (3) | 10 | 1-butene (1) | Benzoquinone (2) + Molecular oxygen | AANa (0.1) |
| Example 72 | Pd(MeCN)$_4$(BF$_4$)$_2$ (25) | NCP (3) | 10 | Propylene (1) | Benzoquinone (2) + Molecular oxygen | AANa (0.1) |
| Example 73 | Pd(OAc)$_2$ (10) | NMP (3) | 10 | Vinyl acetate (2) | Benzoquinone (2) + Molecular oxygen | AANa (0.1) |

| | N$_2$ (kg/cm$^2$) | O$_2$ (kg/cm$^2$) | Temperature (° C.) | Time (h) | Yield (A) of exo-cyclic unsaturated compound (%) | Yield (B) of acyclic unsaturated compound (%) | (A/B) |
|---|---|---|---|---|---|---|---|
| Example 70 | 0.5 | 0.5 | 50 | 16 | 55 | 1.9 | 28.9 |
| Example 71 | 0.5 | 0.5 | 50 | 16 | 52 | 0.2 | 260 |
| Example 72 | 0.5 | 0.5 | 50 | 16 | 34 | 0.1 | 340 |
| Example 73 | 0.5 | 0.5 | 50 | 16 | 23 | 2.0 | 11.5 |

TABLE 7

| | Catalyst (mol %) | Promoter (mg) | Solvent (mL) | Acrylic acid (mmol) | 1-butene (mmol) | Reoxidant agent (mmol) |
|---|---|---|---|---|---|---|
| Example 74 | Pd(OAc)$_2$ (0.4) | (TBA)[V$_2$PMo$_{10}$O$_{40}$] (30) | BN (1.5) | 6 | 5.2 | Benzoquinone (0.3) + Molecular oxygen |
| Example 75 | Pd(OAc)$_2$ (0.6) | (TBA)[V$_2$PMo$_{10}$O$_{40}$] (30) | BN (1.5) | 21 | 3.5 | Benzoquinone (0.3) + Molecular oxygen |
| Example 76 | Pd(OAc)$_2$ (0.5) | (TBA)[V$_2$PMo$_{10}$O$_{40}$] (30) | BN (1.5) | 21 | 3.9 | Benzoquinone (0.3) + Molecular oxygen |
| Example 77 | Pd(OAc)$_2$ (0.5) | (TBA)[V$_2$PMo$_{10}$O$_{40}$] (60) | BN (1.5) | 21 | 3.8 | Benzoquinone (0.3) + Molecular oxygen |
| Example 78 | Pd(OAc)$_2$ (0.7) | (TBA)[V$_2$PMo$_{10}$O$_{40}$] (30) | BN (1.5) | 21 | 3.4 | Tetrachlorohydroquinone (0.3) + Molecular oxygen |
| Example 79 | Pd(OAc)$_2$ (0.5) | (TBA)[V$_2$PMo$_{10}$O$_{40}$] (30) | BN (1.5) | 21 | 3.8 | Naphthoquinone (0.45) + Molecular oxygen |
| Example 80 | Pd(OAc)$_2$ (0.5) | (TBA)[V$_2$PMo$_{10}$O$_{40}$] (30) | BN (1.5) | 21 | 3.8 | Anthraquinone (0.45) + Molecular oxygen |
| Example 81 | Pd(OAc)$_2$ (0.5) | (TBA)[V$_2$PMo$_{10}$O$_{40}$] (30) | BN (1.5) | 21 | 3.8 | Benzoquinone (0.3) + Molecular oxygen |
| Example 82 | Pd(OAc)$_2$ (0.6) | (TBA)[V$_3$SiW$_9$O$_{40}$] (30) | BN (1.5) | 21 | 3.9 | Benzoquinone (0.3) + Molecular oxygen |
| Example 83 | Pd(OAc)$_2$ (0.5) | 10 wt % (NH$_4$)[V$_2$PMo$_{10}$O$_{40}$]/C (200) | BN (1.5) | 21 | 3.6 | Benzoquinone (0.3) + Molecular oxygen |
| Example 84 | PdCl$_2$ (5) | (TBA)[V$_2$PMo$_{10}$O$_{40}$] (30) | BN (1.5) | 21 | 1 | Benzoquinone (0.3) + Molecular oxygen |
| Example 85 | Pd(OAc)$_2$ (0.5) | (TBA)[V$_2$PMo$_{10}$O$_{40}$] (30) | BN (1.5) | 21 | 3.6 | Benzoquinone (0.3) + Molecular oxygen |
| Example 86 | Pd(OAc)$_2$ (0.5) | (TBA)[V$_2$PMo$_{10}$O$_{40}$] (30) | BN (1.5) | 21 | 4.2 | Molecular oxygen |
| Example 87 | Pd(OAc)$_2$ (0.5) | (TBA)[V$_8$PMo$_4$O$_{40}$] (30) | BN (1.5) | 21 | 3.6 | Molecular oxygen |
| Example 88 | Pd(OCOCF$_3$)$_2$ (0.5) | (TBA)[V$_8$PMo$_4$O$_{40}$] (30) | BN (1.5) | 21 | 3.6 | Molecular oxygen |
| Example 89 | Pd(OAc)$_2$ (0.2) | (TBA)[V$_2$PMo$_{10}$O$_{40}$] (30) | BN (1.5) | 21 | 3.7 | Molecular oxygen |
| Example 90 | Pd(OCOCF$_3$)$_2$ (0.2) | (TBA)[V$_8$PMo$_4$O$_{40}$] (30) | BN (1.5) | 21 | 3.7 | Molecular oxygen |
| Example 91 | PdSO$_4$ (0.8) | (TBA)[V$_2$PMo$_{10}$O$_{40}$] (30) | BN (1.5) | 21 | 3.8 | Benzoquinone (0.3) + Molecular oxygen |

TABLE 7-continued

| | | | | | | |
|---|---|---|---|---|---|---|
| Example 92 | [Pd$_4$(CO)$_4$(OAc)$_4$]•2AcOH (0.1) | (TBA)[V$_2$PMo$_{10}$O$_{40}$] (30) | BN (1.5) | 21 | 3.5 | Benzoquinone(0.3) + Molecular oxygen |
| Example 93 | Pd(acac)$_2$ (0.3) | (TBA)[V$_2$PMo$_{10}$O$_{40}$] (30) | BN (1.5) | 21 | 4.1 | Molecular oxygen |
| Example 94 | Pd(OAc)$_2$ (0.2) | (TBA)[V$_8$PMo$_4$O$_{40}$] (30) | BN (1.5) | 21 | 3.7 | Benzoquinone (0.3) + Molecular oxygen |
| Example 95 | Pd(OAc)$_2$ (0.2) | (TBA)[V$_8$PMo$_4$O$_{40}$] (30) | BN (1.5) | 21 | 3.7 | Molecular oxygen |
| Example 96 | Pd(OAc)$_2$ (0.6) | VO(acac)$_2$ (10) | BN (1.5) | 21 | 3.8 | Benzoquinone (0.3) + Molecular oxygen |

| | N$_2$ (kg/cm$^2$) | O$_2$ (kg/cm$^2$) | Temperature (° C.) | Time (h) | Yield of exo-cyclic unsaturated compound (%) |
|---|---|---|---|---|---|
| Example 74 | 0.5 | 3.5 | 50 | 16 | 10 |
| Example 75 | 0.5 | 3.5 | 50 | 16 | 17 |
| Example 76 | 1 | 3.5 | 50 | 16 | 18 |
| Example 77 | 1 | 3.5 | 50 | 16 | 18 |
| Example 78 | 1 | 3.5 | 50 | 16 | 13 |
| Example 79 | 1 | 3.5 | 50 | 16 | 16 |
| Example 80 | 1 | 3.5 | 50 | 16 | 19 |
| Example 81 | 1 | 3.5 | 50 | 24 | 22 |
| Example 82 | 1 | 3.5 | 50 | 16 | 13 |
| Example 83 | 1 | 3.5 | 50 | 16 | 16 |
| Example 84 | 1 | 3.5 | 50 | 16 | 44 |
| Example 85 | 1 | 3.5 (Successive addition: Total pressure 4.5 kg/cm$^2$) | 50 | 16 | 24 |
| Example 86 | 1 | 3.5 | 50 | 16 | 20 |
| Example 87 | 1 | 3.5 | 50 | 16 | 22 |
| Example 88 | 1 | 3.5 | 50 | 16 | 20 |
| Example 89 | 1 | 3.5 (Successive addition: Total pressure 4.5 kg/cm$^2$) | 50 | 65 | 14 |
| Example 90 | 1 | 3.5 (Successive addition: Total pressure 4.5 kg/cm$^2$) | 50 | 65 | 19 |
| Example 91 | 1 | 3.5 | 50 | 16 | 12 |
| Example 92 | 1 | 3.5 | 50 | 16 | 12 |
| Example 93 | 1 | 3.5 | 50 | 16 | 9 |
| Example 94 | 1 | 3.5 | 65 | 64 | 25 |
| Example 95 | 1 | 3.5 | 65 | 64 | 23 |
| Example 96 | 0.5 | 3.5 | 50 | 16 | 18 |

TABLE 8

| | Catalyst (mol %) | Promoter (mol %) | Solvent (mL) | Acrylic acid (mmol) | 1-butene (mmol) | Reoxidant agent (mmol) |
|---|---|---|---|---|---|---|
| Example 97 | Pd(OCOCF$_3$)$_2$ (1.3) | Cu(OAc)$_2$ (1.3) | Toluene (2.5) | 1.4 | 5.4 | Molecular oxygen |
| Example 98 | Pd(OCOCF$_3$)$_2$ (1.3) | Cu(OAc)$_2$ (1.3) | Toluene (2.5) | 1.4 | 5.4 | Molecular oxygen |
| Example 99 | Pd(OCOCF$_3$)$_2$ (1.3) | Cu(OAc)$_2$ (1.3) | Toluene (5) | 1.4 | 9.6 | Molecular oxygen |
| Example 100 | Pd(OCOCF$_3$)$_2$ (4) | Cu(OAc)$_2$ (4) | Toluene (2.5) | 0.55 | 5.4 | Molecular oxygen |
| Example 101 | Pd(OCOCF$_3$)$_2$ (0.8) | Cu(OAc)$_2$ (1.5) | Toluene (4) | 1.4 | 7.7 | Molecular oxygen |
| Example 102 | Pd(OCOCF$_3$)$_2$ (1.3) | None | Toluene (3) | 1 | 5.8 | Molecular oxygen |
| Example 103 | Pd(OCOCF$_3$)$_2$ (1.3) | Cu(OAc)$_2$ (2.6) | Toluene (3) | 1 | 6.2 | Molecular oxygen |
| Example 104 | Pd(OCOCF$_3$)$_2$ (1.3) | Cu(OCOCF$_3$)$_2$ (1.7) | Toluene (3) | 1 | 6.1 | Molecular oxygen |
| Example 105 | Pd(OCOCF$_3$)$_2$ (1.3) | Cu(OCOCF$_3$)$_2$ (1.7) | Toluene (3) | 1 | 9.1 | Molecular oxygen |
| Example 106 | Pd(OCOCF$_3$)$_2$ (1.3) | Cu(OCOCF$_3$)$_2$ (1.7) | Toluene (3) | 1 | 5.8 | Molecular oxygen |
| Example 107 | Pd(OCOCF$_3$)$_2$ (1.3) | Cu(OCOCF$_3$)$_2$ (1.9) | Toluene (3) | 1 | 5.7 | Molecular oxygen |
| Example 108 | Pd(OCOCF$_3$)$_2$ (0.7) | Cu(OCOCF$_3$)$_2$ (0.7) | Toluene (3) | 1.4 | 5.7 | Molecular oxygen |
| Example 109 | Pd(OCOCF$_3$)$_2$ (0.1) | Cu(OCOCF$_3$)$_2$ (0.6) | Toluene (2.5) | 1.5 | 5.9 | Molecular oxygen |
| Example 110 | Pd(OCOCF$_3$)$_2$ (1) | Cu(OAc)$_2$ (2) | Toluene (5) | 1 | 9.2 | Molecular oxygen |
| Example 111 | Pd(OCOCF$_3$)$_2$ (1) | Cu(OCOCF$_3$)$_2$ (1.3) | Toluene (5) | 1 | 9.4 | Molecular oxygen |
| Example 112 | Pd(OCOPh)$_2$ (1) | Cu(OCOCF$_3$)$_2$ (1.3) | Toluene (5) | 1 | 9.5 | Molecular oxygen |
| Example 113 | Pd(OCOPh)$_2$ (1) | Cu(OAc)$_2$ (2.5) | Toluene (5) | 1 | 9.1 | Molecular oxygen |
| Example 114 | Pd(acac)$_2$ (1.2) | Cu(OAc)$_2$ (1.5) | Toluene (3) | 1 | 5.7 | Molecular oxygen |
| Example 115 | Pd(acac)$_2$ (1) | Cu(OCOCF$_3$)$_2$ (1.4) | Toluene (5) | 1 | 9.1 | Molecular oxygen |
| Example 116 | Pd(hfa)$_2$ (1) | Cu(OAc)$_2$ (1.4) | Toluene (5) | 1 | 9.1 | Molecular oxygen |
| Example 117 | Pd(mpp) (1) | Cu(OCOCF$_3$)$_2$ (1.4) | Toluene (5) | 1 | 8.9 | Molecular oxygen |
| Example 118 | Pd(OCOCF$_3$)$_2$ (0.2) | Cu(OCOCF$_3$)$_2$ (1) | Toluene (3) | 1 | 5.2 | Molecular oxygen |
| Example 119 | RhCl(PPh$_3$)$_3$ (2) | Cu(OCOCF$_3$)$_2$ (2.5) | Toluene (5) | 1 | 8.9 | Molecular oxygen |
| Example 120 | Pd(OCOCF$_3$)$_2$ (1) | Cu(OCOCF$_3$)$_2$ (1) | Tetrahydrofuran (3) | 1 | 3.9 | Molecular oxygen |

TABLE 8-continued

|  | Additive (mg) | $N_2$ (kg/cm$^2$) | $O_2$ (kg/cm$^2$) | Temperature (° C.) | Time (h) | Yield of exo-cyclic unsaturated compound (%) |
|---|---|---|---|---|---|---|
| Example 97 | None | 1 | 3.5 | 50 | 16 | 25 |
| Example 98 | Methyl acrylate (55) | 1 | 3.5 | 50 | 16 | 31 |
| Example 99 | Methyl acrylate (55) | 1 | 3.5 | 50 | 16 | 41 |
| Example 100 | Methyl acrylate (55) | 1 | 3.5 | 50 | 16 | 64 |
| Example 101 | None | 1 | 3.5 | 50 | 16 | 21 |
| Example 102 | None | 1 | 3.5 | 50 | 8 | 11 |
| Example 103 | None | 1 | 3.5 | 50 | 8 | 28 |
| Example 104 | None | 1 | 3.5 | 50 | 8 | 32 |
| Example 105 | None | 1 | 3.5 | 50 | 8 | 34 |
| Example 106 | None | 1 | 3.5 | 60 | 8 | 43 |
| Example 107 | None | 1 | 3.5 | 70 | 8 | 58 |
| Example 108 | None | 1 | 3.5 | 70 | 8 | 27 |
| Example 109 | None | 1 | 3.5 | 70 | 6 | 22 |
| Example 110 | None | 1 | 3.5 | 70 | 8 | 66 |
| Example 111 | None | 1 | 3.5 | 70 | 8 | 63 |
| Example 112 | None | 1 | 3.5 | 70 | 8 | 51 |
| Example 113 | None | 1 | 3.5 | 70 | 8 | 45 |
| Example 114 | None | 1 | 3.5 | 50 | 8 | 19 |
| Example 115 | None | 1 | 3.5 | 70 | 8 | 61 |
| Example 116 | None | 1 | 3.5 | 70 | 8 | 64 |
| Example 117 | None | 1 | 3.5 | 70 | 8 | 61 |
| Example 118 | None | 1 | 3.5 | 80 | 65 | 50 |
| Example 119 | None | 1 | 3.5 | 70 | 8 | 0.2 |
| Example 120 | None | 1 | 3.5 | 50 | 6 | 4 |

Tables 1 to 8 are mentioned below. OAc represents $OCOCH_3$. NMP represents N-methylpyrrolidone; DMF represents N,N-dimethylformamide; MeCN represents acetonitrile; DMA represents N,N-dimethylacetamide; BN represents benzonitrile; DME represents dimethoxyethane; AcOBu represents butyl acetate; DMSO represents dimethyl sulfoxide; DMI represents 1,3-dimethyl-2-imidazolidinone; NCP represents N-cyclohexylpyrrolidone; BMI represents 1-butyl-3-methylimidazolium tetrafluoroborate; and AANa represents sodium acrylate; 10 wt % $(NH_4)$ $[V_2PMo_{10}O_{40}]$/C is a promoter having an embodiment in which $(NH_4)_5[V_2PMo_{10}O_{40}]$ is supported on activated carbon, and the proportion of the $(NH_4)_5[V_2PMo_{10}O_{40}]$ is 10% by weight relative to 100% by weight of the entire promoter; TBA represents tetrabutylammonium; acac represents acetylacetonate; hfa represents hexafluoroacetylacetonate; and mpp represents 1,3-bis(4-methoxyphenyl)-1,3-propanedionate. The symbol "-" in the column of maximum distribution diameter of multi-nuclear compound means that it was not measured. The amount of the catalyst or the promoter (mol %) represents an amount relative to the unsaturated organic compound in Examples 1 to 96 and represents an amount relative to the α,β-unsaturated carboxylic acid in Examples 97 to 121. The yield is calculated on the basis of the unsaturated organic compound in Examples 1 to 96 and it is calculated on the basis of the α,β-unsaturated carboxylic acid in Examples 97 to 121 and Comparative Example 1.

In Examples 1 to 15 in Table 1, the multi-nuclear compound of the catalyst was measured for maximum distribution diameter after completion of the reaction by small angle X-ray scattering analysis using an X-ray diffraction apparatus (product of Rigaku-Corp., RINT2400).

In Example 14, no multi-nuclear compounds were observed.

In Examples 1 to 84, 86 to 88, 91 to 121, and Comparative Example 1, the nitrogen gas and the oxygen gas were added at the proportions mentioned in the above Tables 1 to 8 and the like, at the beginning of the reaction, and then heated. The pressure which was once increased was decreased with consumption of oxygen or the substrate by the reaction, but in Examples 85, 89, 90, oxygen was newly added to maintain the total pressure to 4.5 kg/cm$^2$ even if oxygen or the substrate was consumed by the reaction.

In Table 1, (+Pd black) means that black precipitation of palladium black was visually observed.

The above-mentioned Examples show the followings. That is, it is shown that the desired cyclic unsaturated compound is obtained by reacting the α,β-unsaturated carboxylic acid with the unsaturated organic compound in the presence of the above-mentioned catalyst. Particularly, it is shown that if the catalyst essentially includes at least one element selected from the group consisting of elements of the Groups 8 to 12, the yield of the cyclic unsaturated compound is increased. Further, it is shown that if the above-mentioned catalyst is supported on the carrier, the advantageous effects in which the reaction rate and the yield of the cyclic unsaturated compound can be sufficiently increased are remarkably exhibited. Specifically, if the above-mentioned catalyst was carried on the carrier, the yield of the exo-cyclic unsaturated compound was increased from 0.2% up to 15% (Example 19). Further, when the catalyst supported on the carrier was used instead of palladium acetate, the selectivity can be improved even in the acrylic acid solvent.

It is shown that if the above-mentioned production method includes the step of reacting the α,β-unsaturated carboxylic acid with the unsaturated organic compound in the presence of the basic compound, the advantageous effects in which generation of acyclic unsaturated compounds can be sufficiently suppressed and the reaction rate and the yield of the cyclic unsaturated compound can be sufficiently increased are remarkably exhibited. Specifically, according to the above-mentioned production method including the step of reacting the α,β-unsaturated carboxylic acid with the unsaturated organic compound in the presence of the basic compound, if acrylic acid as the α,β-unsaturated carboxylic acid, ethylene as the unsaturated organic compound, benzoquinone and molecular oxygen as the reoxidant agent were used, the yield of the exo-cyclic unsaturated compound was increased from 3.6% to 33%, and the value (A/B) of the yield of the exo-cyclic unsaturated compound (A) to the yield of the acyclic unsaturated compound (B), that is, the selectivity of α-methylene-γ-butyrolactone to vinyl acrylate was increased from 0.9 to 5.2 (Examples 46 and 63). In addition, if acrylic acid as the α,β-unsaturated carboxylic acid and ethylene as the unsaturated organic compound, and benzoquinone, manganese dioxide and molecular oxygen as the reoxidant agent were used, the yield of the exo-cyclic unsaturated compound was increased from 6.8% to 29% and the above-mentioned (A/B) was increased from 2.3 to 4.4 (Examples 47 and 64). Further if norbornene was used as the unsaturated organic compound, the yield of the exo-cyclic unsaturated compound was increased from 29% to 54% (Examples 66 and 67). If 1-octene was used as the unsaturated organic compound, the yield of the exo-cyclic unsaturated compound was increased from 9% to 25% (Examples 68 and 69).

According to the above-mentioned Examples, sodium acrylate, lithium carbonate, or calcium carbonate was used as the basic compound. As long as the basic compound was used, the mechanism in which the carboxyl group of the α,β-unsaturated carboxylic acid was converted to a carboxylate anion and the reactivity with the unsaturated organic compound is improved, thereby increasing the reaction rate and the yield is common to those Examples. Accordingly, the above-mentioned production method can surely exhibit the advantageous effects of the present invention. At least in the case where the above-mentioned production method includes the step of reacting the α,β-unsaturated carboxylic acid with the unsaturated organic compound in the presence of sodium acrylate, lithium carbonate or calcium carbonate, the above-mentioned Examples sufficiently prove the advantageous effects of the present invention and support the technical meanings of the present invention.

Further, it is shown that if the above-mentioned production method includes the step of reacting the α,β-unsaturated carboxylic acid with the unsaturated organic compound in the presence of the solvent different from the substrate, the advantageous effects in which generation of acyclic unsaturated compounds can be sufficiently suppressed and the reaction rate and the yield of the cyclic unsaturated compound can be sufficiently increased are remarkably exhibited. In the case where the reaction was performed in the presence of the basic compound using ethylene as the unsaturated organic compound, if the above-mentioned production method includes the step of reacting the α,β-unsaturated carboxylic acid with the unsaturated organic compound in the presence of the solvent, the yield of the acyclic unsaturated compound was reduced from 36% to 0.5-29% (Examples 33 to 43, 45 to 61, and 44). Further, if the solvent essentially includes the nitrogen-containing compound having an amide group in the molecule, the value (A/B) of the yield of the cyclic unsaturated compound (A) to the yield of the acyclic unsaturated compound (B), that is, the selectivity of methylene lactone to vinyl acrylate was improved. Specifically, comparison among Examples 33 to 40 where the conditions other than the kind of the solvent were the same shows that if the nitrogen-containing compound having an amide group in the molecule was essentially included as the solvent, the selectivity was improved from 0.1-0.3 to 0.6-1.0 . In these Examples, the effects of the present invention were further remarkably exhibited.

In Examples 74 to 81, 84 to 86, 89, and 91 to 93 where the reaction was performed in the presence of the nitrile solvent (benzonitrile), (TBA) [$V_2PMo_{10}O_{40}$] was used as a promoter. If Examples 78 to 81 where the reoxidant agent (tetrachlorohydroquinone, naphthoquinone, anthraquinone, benzoquinone, or molecular oxygen) was used is compared with Example 86 where quinones were not used as the reoxidant agent, the yield of methylene lactone was 13 to 22% in Examples 78 to 81 but it was 20% in Example 86 . Therefore, it is shown that sufficiently high yield of methylene lactone can be obtained without using quinones.

In Examples 97 to 118 where the reaction was performed in the presence of a non-coordinating solvent, that is, hydrocarbon solvent (toluene) as the solvent, using the palladium-containing catalyst, the use of the promoter (copper acetate or copper trifluoroacetate) increases the yield of the methylene lactone from 11% (Example 102) to 19-66% (Examples 97 to 101 and 103 to 118).

Further, in Example 121 where crotonic acid was used as the α,β-unsaturated carboxylic acid, γ-ethyl-α-vinyl-γ-butyrolactone was selectively generated.

In Comparative Example 1 where no catalysts were used, the yield of the cyclic unsaturated compound was 0%.

According to the above-mentioned Examples, N-methylpyrrolidone, N,N-dimethylformamide, acetonitrile, N,N-dimethylacetamide, benzonitrile, dimethoxyethane, dichloromethane, butyl acetate, dimethyl sulfoxide, 1,3-dimethyl-2-imidazolidinone, N-cyclohexylpyrrolidone, 1-butyl-3-methylimidazolium tetrafluoroborate, cyclohexane, and toluene were used as the solvent, but the mechanism in which generation of acyclic unsaturated compounds is suppressed is common to those Examples. Accordingly, the above-mentioned production method can surely exhibit the advantageous effects of the present invention. At least in the case where the cyclic unsaturated compound is produced by the production method of the present invention in the presence of the above-mentioned various solvents, the above-mentioned Examples prove the advantageous effects of the present invention and support the technical meanings of the present invention.

The above-mentioned Examples show that if the above-mentioned production method includes the step of reacting the α,β-unsaturated carboxylic acid with the unsaturated organic compound in the presence of the catalyst, the advantageous effects in which generation of acyclic unsaturated compounds can be sufficiently suppressed and the reaction rate and the yield can be sufficiently increased are remarkably exhibited.

Further if alkene having a substituent, such as propylene, 1-butene, and the like, instead of ethylene, is used as the unsaturated organic compound, the value A/B (selectivity) is further improved due to the steric effect (Tables 2 and 6).

In industrial production of cyclic unsaturated compounds, for example, the production can be performed at low costs and with high efficiency if a proportion of byproducts is reduced as much as possible and a proportion of a desired substance is increased. Such effects, that is, effects in which a yield of a desired substance is increased; a proportion of byproducts is reduced; and industrial production at low costs and with high efficiency is permitted are outstandingly observed in the production method of the present invention.

BRIEF DESCRIPTION OF DRAWINGS

FIG. 1 is a schematic view showing a possible reaction step in Example 1. Pd (oxidation state) represents palladium in the oxidation state (for example, monovalent to tetravalent palladium, and positively charged palladium) and Pd (reduction state) represents palladium in the reduction state (for example, zero-valent palladium). For example, in Example 1, the α,β-unsaturated carboxylic acid is acrylic acid, the unsaturated organic compound is ethylene, and the cyclic unsaturated compound is α-methylene-γ-butyrolactone. After the unsaturated organic compound is coordinated to palladium, the α,β-unsaturated carboxylic acid (ion) attacks the unsaturated bond of the unsaturated organic compound (or ethylene is inserted into the palladium-acrylate species) and bonded thereto. Then, the unsaturated bond of the α,β-unsaturated carboxylic acid causes an insertion reaction into the generated palladium-carbon bond, and after β-hydride elimination, a desired cyclic unsaturated compound is obtained. At this time, one or more palladiums are involved in the reaction. In addition, the basic path is not different, but a case where the reaction proceeds while the oxidation state (for example, divalent) of the palladium is maintained and the reaction proceeds, and a case where the palladium species in the reduction state serves as an active species and the reaction proceeds, may be mentioned.

FIG. 2 is a view schematically showing a possible reaction step in Example 121. Pd (oxidation state) represents palladium in the oxidation state (for example, monovalent to tetravalent palladium, and positively charged palladium) and Pd (reduction state) represents palladium in the reduction state (for example, zero-valent palladium). For example, in Example 121, the α,β-unsaturated carboxylic acid is crotonic acid and the unsaturated organic compound is 1-butene, and the cyclic unsaturated compound is γ-ethyl-α-vinyl-γ-butyrolactone. After the unsaturated organic compound is coordinated to palladium, the α,β-unsaturated carboxylic acid (ion) attacks the unsaturated bond of the unsaturated organic compound (or ethylene is inserted into the palladium-crotylate species) and bonded thereto. Then, the unsaturated bond of the α,β-unsaturated carboxylic acid causes an insertion reaction into the generated palladium-carbon bond, and after β-hydride elimination, a desired cyclic unsaturated compound is obtained. At this time, one or more palladiums are involved in the reaction. In addition, the basic path is not different, but a case where the reaction proceeds while the oxidation state (for example, divalent) of the palladium is maintained and the reaction proceeds, and a case where the palladium species in the reduction state serves as an active species and the reaction proceeds, may be mentioned.

FIG. 3 is a view schematically showing a possible oxidation reduction mechanism of a catalytic active species (palladium species).

FIG. 4 is a view schematically showing a possible oxidation reduction mechanism of a catalytic active species (palladium species).

Figure 1:
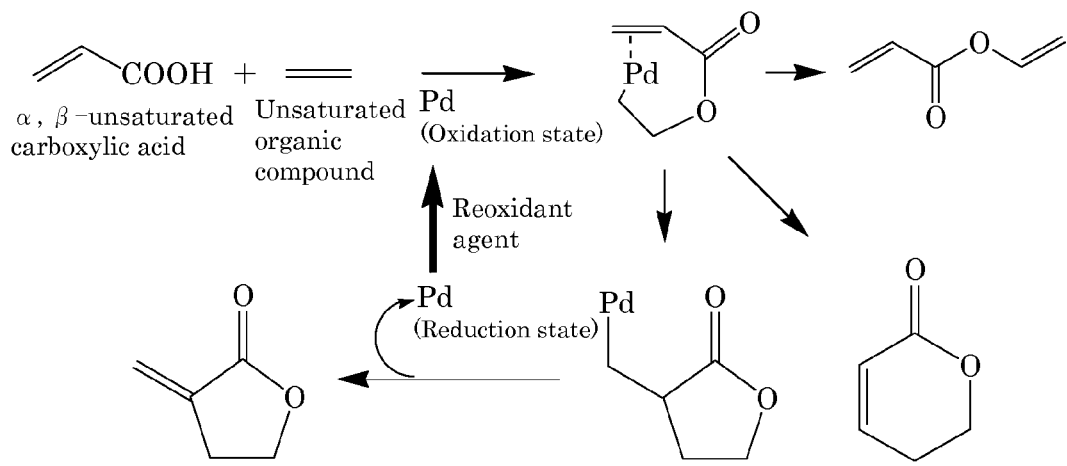
[FIG. 1]
Figure 2:
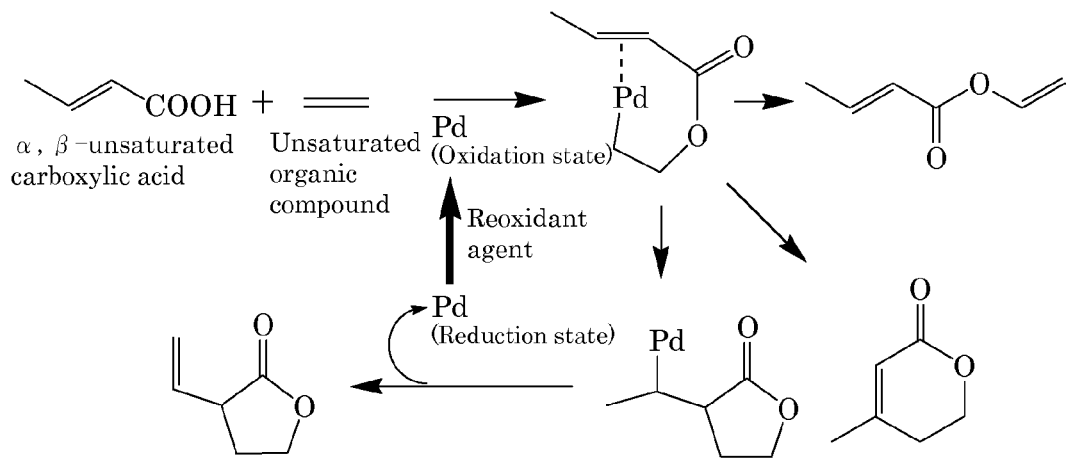
[FIG. 2]
Figure 3:
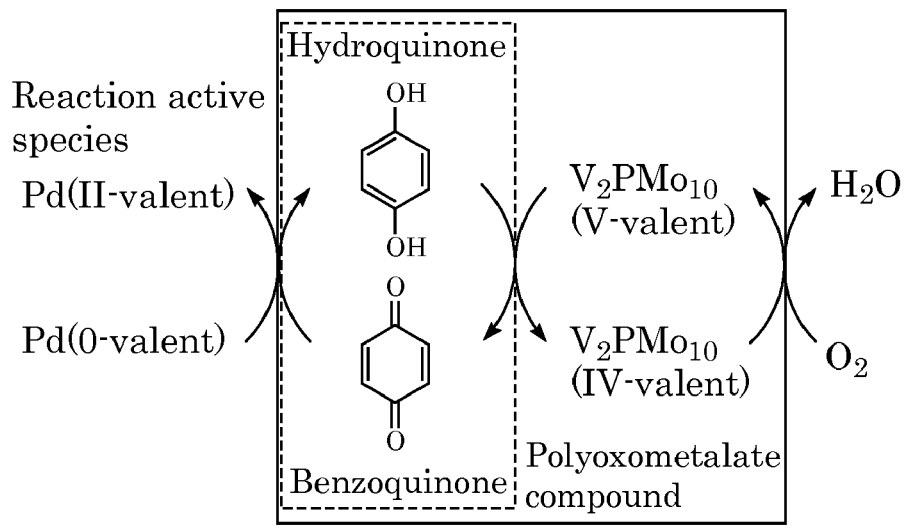
[FIG. 3]
Figure 4:
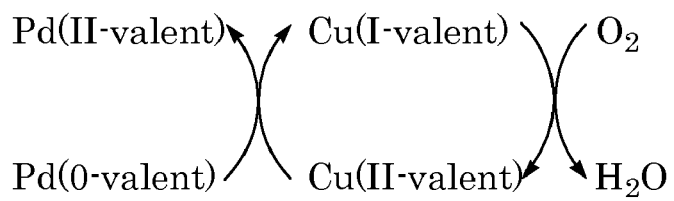
[FIG. 4]
Figure 5:
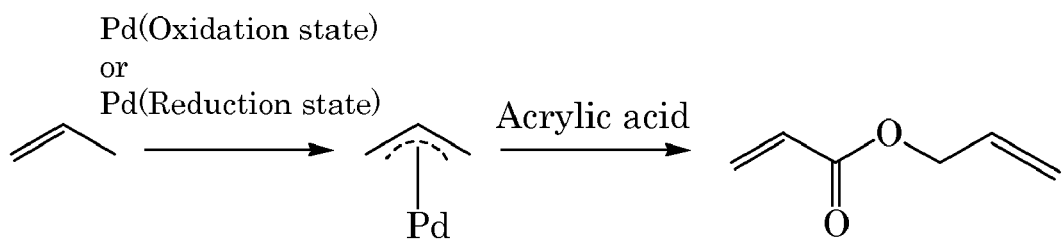
[FIG. 5]

If the unsaturated organic compound includes at least one hydrogen atom at the allylic position, like propylene, the unsaturated organic compound once becomes a π-allyl intermediate in the reaction steps according to the production method of the present invention, and then the α,β-unsaturated carboxylic acid (ion) attacks the π-allyl intermediate, and thereby a acyclic unsaturated compound may be produced as a by product. For example, the α,β-unsaturated carboxylic acid is acrylic acid, the unsaturated organic compound is propylene, and the acyclic unsaturated compound is propenyl acrylate. This reaction is applied to both cases in FIGS. 1 and 2.

INDUSTRIAL APPLICABILITY

The method for producing the cyclic unsaturated compound of the present invention has the above-mentioned configuration and the method is a useful production method which can be applied to industrial production because the method can reduce generation of acyclic unsaturated compounds in reaction steps and improve a reaction rate and a yield of the cyclic unsaturated compound.

The invention claimed is:

1. A method for producing a cyclic unsaturated compound represented by the formula (4):

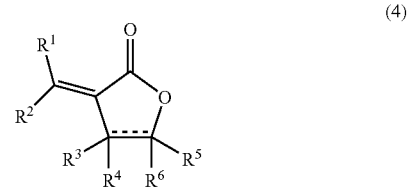

(4)

wherein $R^1$ and $R^2$ are the same as defined below for formula (2) and $R^3$, $R^4$, $R^5$, and $R^6$ are the same as defined below for formula (3), the method comprising reacting an α, β-unsaturated carboxylic acid with an unsaturated organic compound, wherein the α, β-unsaturated carboxylic acid is represented by the following formula (2):

(2)

in the formula, $R^1$ and $R^2$ may be the same or different, and represent a hydrogen atom, an alkyl group containing 1 to 12 carbon atoms, a cycloalkyl group containing 3 to 8 carbon atoms, or an aromatic part-containing group, the $R^1$ and $R^2$ may be bonded to one another to form a ring structure, the method comprises: a step of reacting the α, β-unsaturated carboxylic acid with the unsaturated organic compound in the presence of a catalyst; and a step of reoxidizing the catalyst using a reoxidant agent, and molecular oxygen is used as one reoxidant agent in the step of reoxidizing the catalyst, the catalyst comprises at least one member selected from the group consisting of mono-, di-, tri-, and tetra-valent palladium and positively charged palladium, the unsaturated organic compound is represented by the following formula (3):

(3)

in the formula (3), each one of $R^3$, $R^4$, $R^5$, and $R^6$ individually represents a hydrogen atom; a member having 1 to 60 carbon atoms selected from the group consisting of linear saturated alkyl groups, branched saturated alkyl groups, alicyclic saturated alkyl groups, unsubstituted aryl groups and a member having up to 60 carbon atoms and an ester group, and $R^3$, $R^4$, $R^5$, and $R^6$ may be bonded to one another to form a ring structure.

2. The method for producing the cyclic unsaturated compound according to any of claim 1, wherein the method comprises a step of reacting the α, β-unsaturated carboxylic acid with the unsaturated organic compound in the presence of a promoter.

3. The method for producing the cyclic unsaturated compound according to claim 2, wherein the promoter is one or more compounds including at least one element selected from the group consisting of vanadium, molybdenum, tungsten, manganese, iron, cobalt, copper, silver, gold, antimony, bismuth, selenium, and tellurium.

4. The method for producing the cyclic unsaturated compound according to claim 1, wherein the method comprises a step of reacting the α, β-unsaturated carboxylic acid with the unsaturated organic compound in the presence of a hydrocarbon solvent.

5. The method for producing the cyclic unsaturated compound according to claim 1, wherein the method comprises a step of reacting the α, β-unsaturated carboxylic acid with the unsaturated organic compound in the presence of a nitrile solvent.

6. The method for producing the cyclic unsaturated compound according to claim 1, wherein the method comprises a step of reacting the α, β-unsaturated carboxylic acid with the unsaturated organic compound in the presence of an ester solvent.

7. The method for producing the cyclic unsaturated compound according to claim 1, wherein the method comprises a step of inserting an unsaturated bond of the α, β-unsaturated. carboxylic acid into a metal-carbon bond.

8. The method for producing the cyclic unsaturated compound according to claim 1, wherein the α, β-unsaturated carboxylic acid includes at least one hydrogen atom at carbon at a gamma-position.

9. The method for producing the cyclic unsaturated compound according to claim 1, wherein the unsaturated organic compound is a double bond-containing compound having 2 to 20 carbon atoms.

10. The method for producing the cyclic unsaturated compound according to claim 1,
wherein the cyclic unsaturated compound comprises an α-methylene-γ-butyrolactone,
which comprises producing an α-methylene-γ-butyrolactone composition including the α-methylene-γ-butyrolactone and a cyclic unsaturated compound containing a double bond at an endo position, wherein the cyclic unsaturated compound containing a double bond at the endo position is 0.01 to 50 mol % in 100 mol % of the α-methylene-γ-butyrolactone, and
wherein the α-methylene-γ-butyrolactone composition is used for forming a heat resistant polymer or an optical polymer.

11. The method for producing the cyclic unsaturated compound according to claim 1,
wherein the cyclic unsaturated compound comprises an α-methylene-γ-butyrolactone, which comprises producing an α-methylene-γ-butyrolactone composition including the α-methylene-γ-butyrolactone, and a six-membered unsaturated compound,
wherein the six-membered unsaturated compound is 0.01 to 50 mol % in 100 mol % of the α-methylene-γ-butyrolactone, and
wherein the α-methylene-γ-butyrolactone composition is used for forming a heat resistant polymer or an optical polymer.

12. The method for producing the cyclic unsaturated compound according to claim 2, wherein the method comprises a step of reacting the α, β-unsaturated carboxylic acid with the unsaturated organic compound in the presence of a hydrocarbon solvent.

13. The method for producing the cyclic unsaturated compound according to claim 1, wherein, the catalyst is at least one member selected from the group consisting of palladium carboxylates, palladium nitrate, palladium sulfate, palladium chloride, palladium bromide, palladium iodide, palladium hydroxide, and tetrakis(acetonitrile)palladium tetrafluoroborate, palladiums containing an organic ligand coordinated to the palladium via oxygen, bis(acetonitrile)palladium chloride, bis(benzonitrile)palladium chloride, palladiums containing an organic ligand coordinated to the palladium by an unsaturated bond, sodium tetrachloropalladium, potassium tetrachloropalladium, nitrogen atom-containing organic compound-coordinated palladium, nitro group-coordinated palladium, nitroso group-coordinated palladium, palladium oxide; and monovalent palladium.

14. The method for producing the cyclic unsaturated compound according to claim 13, wherein, the palladium carboxylate is at least one member selected from the group consisting palladium acetate and palladium trifluoroacetate.

15. The method for producing the cyclic unsaturated compound according to claim 13, wherein, the palladium containing an organic ligand coordinated to the palladium via oxygen is bis(acetylacetonato)palladium.

16. The method for producing the cyclic unsaturated compound according to claim 13, wherein, the palladium containing an organic ligand coordinated to the palladium by an unsaturated bond is dichloro(octadiene) palladium.

17. The method for producing the cyclic unsaturated compound according to claim 13, wherein, the monovalent palladium is $[Pd_4(CO)_4(OAc)_4] \cdot 2AcOH$.

18. The method for producing the cyclic unsaturated compound according to claim 1, wherein the reoxidant agent used in the step of reoxidizing the catalyst is molecular oxygen.

19. The method for producing the cyclic unsaturated compound according to claim 1, wherein the amount of the reoxidant agent is 0.0000001 mol % or more and 10000000 mol % or less relative to 100 mol % of the α, β-unsaturated carboxylic acid.

20. The method for producing the cyclic unsaturated compound according to claim 1, wherein manganese dioxide is not used in the reaction system.

* * * * *

UNITED STATES PATENT AND TRADEMARK OFFICE
CERTIFICATE OF CORRECTION

| | |
|---|---|
| PATENT NO. | : 8,093,409 B2 |
| APPLICATION NO. | : 12/438183 |
| DATED | : January 10, 2012 |
| INVENTOR(S) | : Koji Yonehara |

It is certified that error appears in the above-identified patent and that said Letters Patent is hereby corrected as shown below:

Claim 1, column 66, line 49, please amend "a" (second occurrence) to read "α".

Signed and Sealed this
Thirteenth Day of March, 2012

David J. Kappos
*Director of the United States Patent and Trademark Office*